(12) United States Patent
Brunner et al.

(10) Patent No.: US 9,221,816 B2
(45) Date of Patent: Dec. 29, 2015

(54) 2-OXO-2,3-DIHYDRO-INDOLES FOR THE TREATMENT OF CNS DISORDERS

(71) Applicant: Hoffmann-La Roche Inc., Little Falls, NJ (US)

(72) Inventors: Daniela Brunner, Tarrytown, NY (US); Jessica Malberg, Tarrytown, NY (US); Bavani G. Shankar, Tarrytown, NY (US); Sabine Kolczewski, Loerrach (DE); Anja Limberg, Basel (CH); Eric Prinssen, Guebwiller (FR); Claus Riemer, Freiburg (DE); Theodor Stoll, Binningen (CH)

(73) Assignee: Hoffmann La-Roche Inc., Little Falls, NJ (US)

( * ) Notice: Subject to any disclaimer, the term of this patent is extended or adjusted under 35 U.S.C. 154(b) by 0 days.

(21) Appl. No.: 14/645,033

(22) Filed: Mar. 11, 2015

(65) Prior Publication Data

US 2015/0284386 A1    Oct. 8, 2015

Related U.S. Application Data

(63) Continuation of application No. PCT/EP2012/068668, filed on Sep. 10, 2013.

(30) Foreign Application Priority Data

Sep. 13, 2012   (EP) .................................... 12184249

(51) Int. Cl.
| | |
|---|---|
| C07D 471/04 | (2006.01) |
| C07D 401/12 | (2006.01) |
| C07D 403/12 | (2006.01) |
| C07D 405/14 | (2006.01) |
| A61K 31/506 | (2006.01) |
| A61K 31/4439 | (2006.01) |
| A61K 31/444 | (2006.01) |
| A61K 45/06 | (2006.01) |

(52) U.S. Cl.
CPC ............ *C07D 471/04* (2013.01); *A61K 31/444* (2013.01); *A61K 31/4439* (2013.01); *A61K 31/506* (2013.01); *A61K 45/06* (2013.01); *C07D 401/12* (2013.01); *C07D 403/12* (2013.01); *C07D 405/14* (2013.01)

(58) Field of Classification Search
None
See application file for complete search history.

(56) References Cited

FOREIGN PATENT DOCUMENTS

JP    WO2010123139 A1 * 10/2010 ........... A61K 31/167

* cited by examiner

*Primary Examiner* — Michael Barker
(74) *Attorney, Agent, or Firm* — Brian Buckwalter

(57) ABSTRACT

The present invention is concerned with 2-oxo-2,3-dihydro-indoles of general formula

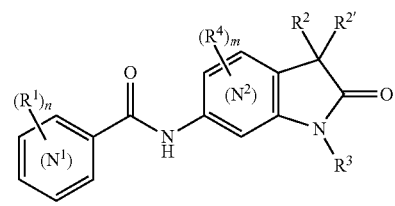

wherein

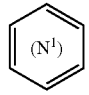

is phenyl or a heteroaryl group, selected from pyridinyl, pyrimidinyl, imidazolyl, isoxazolyl or pyrazolyl;

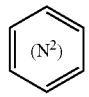

is phenyl or pyridinyl, wherein the N atom in the pyridinyl group may be on all free positions;

$R^1$ is hydrogen, lower alkyl, lower alkyl substituted by halogen, lower alkoxy or halogen;

n is 1 or 2; if n is 2, $R^1$ may be the same or not;

$R^2/R^{2'}$ are independently from each other lower alkyl, or form together with the carbon atom to which they are attached a $C_{3-6}$-cycloalkyl ring;

$R^3$ is lower alkyl, $C_{3-6}$-cycloalkyl, $CH_2$—$C_{3-6}$-cycloalkyl, $C_{3-6}$-cycloalkyl wherein one ring-carbon atom is replaced by —O—, $(CH_2)_3$—O—$C_{3-6}$-cycloalkyl, lower alkyl substituted by hydroxy, lower alkyl substituted by halogen, $(CH_2)_3$—$S(O)_2$—$C_{3-6}$-cycloalkyl or $(CH_2)_2$—$S(O)_2$-lower alkyl;

$R^4$ is hydrogen, halogen or lower alkyl;

m is 1 or 2; if m is 2, $R^4$ may be the same or not;

as well as with a pharmaceutically acceptable salts thereof, with a racemic mixture, or with its corresponding enantiomer and/or optical isomer and/or stereoisomer thereof.

18 Claims, No Drawings

2-OXO-2,3-DIHYDRO-INDOLES FOR THE TREATMENT OF CNS DISORDERS

CROSS REFERENCE TO RELATED APPLICATIONS

This Application is a Continuation of International Application No. PCT/EP2013/068668 filed on Sep. 10, 2013, which is entitled to the priority of EP Application No. 12184249.6 filed on Sep. 13, 2012, the disclosures of which are incorporated herein by reference in their entirety.

BACKGROUND OF THE INVENTION

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements prior to antipsychotic treatment. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone, olanzapine, however, fail to significantly ameliorate the negative symptoms and cognitive dysfunction.

Antipsychotic drugs have shown clinical efficacy for the treatment of the following diseases:
Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs*, 2012, 26(2): 135-53).

Schizoaffective disorders: includes psychotic and affective symptoms, this disorder falls on a spectrum between bipolar disorders (with depressive and manic episodes, alcohol and drug #651987 addiction, substance abuse) and schizophrenia, *J. Clin. Psychiatry*, 2010, 71, Suppl. 2, 14-9, *Pediatr. Drugs* 2011, 13 (5), 291-302; Major depression: *BMC Psychiatry* 2011, 11, 86; Treatment resistant depression: *Journal of Psychopharmacology*, 0(0) 1-1: Anxiety: *European Neuropsychopharmacology*, 2011, 21, 429-449: Bipolar disorders: *Encephale, International J. of Neuropsychopharmacology*, 2011, 14, 1029-1049: *International J. of Neuropsychopharmacology*, 2012, pages 1-12: *J. of Neuropsychopharmacology*, 2011, 0(0), 1-15: Mood disorders: *J. Psychopharmacol.* 2012 Jan. 11: *CNS Drugs*, 2010 Feb. 24(2), 131-61: Autism: *Current opinion in pediatrics*, 2011, 23:621-627; *J. Clin. Psychiatry*, 2011, 72(9), 1270-1276: Alzheimer's disease: *J. Clin. Psychiatry*, 2012, 73(1), 121-128: Parkinson's disease: *Movement Disorders*, Vol. 26, No. 6, 2011: Chronic fatigue syndrome: *European* Neuropsychopharmacology, 2011, 21, 282-286: Borderline Personality disorder: *J. Clin. Psychiatry*, 2011, 72 (10), 1363-1365: *J. Clin. Psychiatry*, 2011, 72 (10), 1353-1362: Antiinflammatory effects in arthritis: *European J. of Pharmacology*, 678, 2012, 55-60.

Compounds structurally similar to those described herein are shown in WO2007063925 (Astellas Pharma/Japan), wherein the described active compounds have a NHR-substitution on the left phenyl or heteroaryl group, for the treatment of pain; WO0056709 and WO0008202 (Sugen, Inc./USA) describe compounds without substitution on the 2-oxo-2,3-dihydro-indol ring for the treatment of cancer, hepatitis, ocular diseases and cardiovascular diseases; DE 3925584, EP0344634, DE 3803775, U.S. Pat. No. 4,835,280, U.S. Pat. No. 4,810,801, DE 3501497, EP0161632 and DE 3417643 (Boehringer Mannheim/DE) describe 2-oxo-2,3-dihydro-indol derivatives without substitution in 1-position (N-atom) for use as intermediates or for the treatment of heart and circulatory diseases, for influencing thrombocyte function and for the treatment of cardiovascular diseases.

SUMMARY OF THE INVENTION

The present invention is concerned with 2-oxo-2,3-dihydro-indoles of general formula

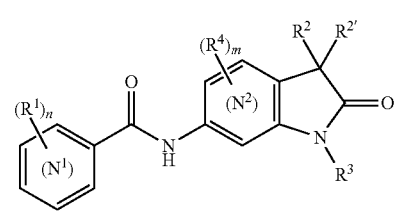

wherein

is phenyl or a heteroaryl group, selected from pyridinyl, pyrimidinyl, imidazolyl, isoxazolyl or pyrazolyl;

is phenyl or pyridinyl, wherein the N atom in the pyridinyl group may be on all free positions;
$R^1$ is hydrogen, lower alkyl, lower alkyl substituted by halogen, lower alkoxy or halogen;
n is 1 or 2; if n is 2, $R^1$ may be the same or not;
$R^2/R^{2'}$ are independently from each other lower alkyl, or form together with the carbon atom to which they are attached a $C_{3-6}$-cycloalkyl ring;
$R^3$ is lower alkyl, $C_{3-6}$-cycloalkyl, $CH_2$—$C_{3-6}$-cycloalkyl, $C_{3-6}$-cycloalkyl wherein one ring-carbon atom is replaced by —O—, $(CH_2)_3$—O—$C_{3-6}$-cycloalkyl, lower alkyl substituted by hydroxy, lower alkyl substituted by halogen, (CH$_2$)$_3$—S(O)$_2$—C$_{3-6}$-cycloalkyl or (CH$_2$)$_2$—S(O)$_2$-lower alkyl;
R$^4$ is hydrogen, halogen or lower alkyl;
m is 1 or 2; if m is 2, R$^4$ may be the same or not;
as well as with a pharmaceutically acceptable salts thereof, with a racemic mixture, or with its corresponding enantiomer and/or optical isomer and/or stereoisomer thereof,
and
with the use of compounds of formula I-1

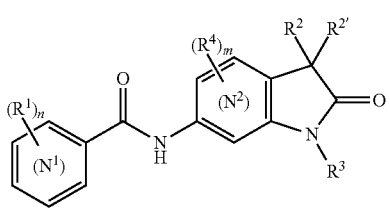

wherein

is phenyl or a heteroaryl group, selected from pyridinyl, pyrimidinyl, imidazolyl, isoxazolyl or pyrazolyl;

is phenyl or pyridinyl, wherein the N atom in the pyridinyl group may be on all free positions;
R$^1$ is hydrogen, lower alkyl, lower alkyl substituted by halogen, lower alkoxy or halogen;
n is 1 or 2; if n is 2, R$^1$ may be the same or not;
R$^2$/R$^{2'}$ are independently from each other lower alkyl, or form together with the carbon atom to which they are attached a C$_{3-6}$-cycloalkyl ring;
R$^3$ is hydrogen, lower alkyl, C$_{3-6}$-cycloalkyl, CH$_2$—C$_{3-6}$-cycloalkyl, C$_{3-6}$-cycloalkyl wherein one ring-carbon atom is replaced by —O—, (CH$_2$)$_3$—O—C$_{3-6}$-cycloalkyl, lower alkyl substituted by hydroxy, lower alkyl substituted by halogen, (CH$_2$)$_3$—S(O)$_2$—C$_{3-6}$-cycloalkyl or (CH$_2$)$_2$—S(O)$_2$-lower alkyl;
R$^4$ is hydrogen, halogen or lower alkyl;
m is 1 or 2; if m is 2, R$^4$ may be the same or not;
as well as with a pharmaceutically acceptable salts thereof, with a racemic mixture, or with its corresponding enantiomer and/or optical isomer and/or stereoisomer thereof, for the treatment of certain central nervous system disorders which are positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems.

Now it has been found that the compounds of formula I and I-1 may be used for the treatment of CNS diseases. The described compounds have been shown to reverse the L-687, 414 ((3R,4R)-3-amino-1-hydroxy-4-methyl-pyrrolidin-2-one, a NMDA glycine site antagonist) induced hyperlocomotion, a behavioral pharmacodynamic mouse model for schizophrenia predictive of efficacy in human patients, described by D. Alberati et al. in *Pharmacology, Biochemistry and Behavior*, 97 (2010), 185-191. The authors described that hyperlocomotion induced by L-687,414 was inhibited by a series of known antipsychotic drugs. The compounds of formula I and I-1 demonstrate marked activity in this model. These findings predict antipsychotic activity for the present compounds, making them useful for the treatment of schizophrenia and other disorders as described above. The results are shown in Table 1.

In addition to the reversal of L-687,414 induced hyperlocomotion experiment as described above, some compounds of the present invention have been tested in SmartCube®, an automated system in which the behaviors of compound-treated mice in response to multiple challenges are captured by digital video and analyzed with computer algorithms (Roberds et al., Frontiers in Neuroscience, 2011, Vol. 5, Art. 103, 1-4). In this way, the neuro-pharmacological effects of a test compound can be predicted by similarity to major classes of compounds, such as antipsychotics, anxiolytics and antidepressants. Examples 29 and 30 showed similarity to atypical antipsychotics thereby predicting efficacy similar to atypical antipsychotics in human patients. The results are shown in Table 2.

DETAILED DESCRIPTION OF THE INVENTION

Objects of the present invention are novel compounds of formula I and the use of compounds of formula I and I-1 and their pharmaceutically acceptable salts for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems. Further objects of the present invention are medicaments containing such novel compounds as well as methods for preparation of compounds of formula I, a combination of compounds of formula I or I-1 with marketed antipsychotics, antidepressants, anxiolytics or mood stabilizers, and methods for the treatment of CNS disorders as mentioned above.

Encompassed by the present invention are corresponding prodrugs of compounds of formulas I and I-1.

A common antipsychotic drug for the treatment of schizophrenia is olanzapine. Olanzapine (Zyprexa) belongs to a drug class known as atypical antipsychotics. Other members of this class include for example clozapine (Clozaril), risperidone (Risperdal), aripiprazole (Abilify) and ziprasidone (Geodon).

Olanzapine is approved for the treatment of psychotic disorders, long term treatment of bipolar disorders and in combination with fluoxetine for the treatment of depressive episodes associated with bipolar disorders and for the treatment of resistant depression. The compounds of the present invention may be combined with antipsychotic drugs like olanzapine (Zyprexa), clozapine (Clozaril), risperidone (Risperdal), aripiprazole (Abilify), amisulpride (Solian), asenapine (Saphris), blonanserin (Lonasen), clotiapine (Entumine), iloperidone (Fanapt), lurasidone (Latuda), mosapramine (Cremin), paliperidone (Invega), perospirone (Lullan), quetiapine (Seroquel), remoxipride (Roxiam), sertindole (Serdolect), sulpiride (Sulpirid, Eglonyl), ziprasidone (Geodon, Zeldox), zotepine (Nipolept), haloperidol (Haldol, Serenace), droperidol (Droleptan), chlorpromazine (Thorazine, Largactil), fluphenazine (Prolixin), perphenazine (Trilafon), prochlorperazine (Compazine), thioridazine (Mellaril, Melleril), trifluoperazine (Stelazine), triflupromazine (Vesprin), levomepromazine (Nozinan), promethazine (Phenergan), pimozide (Orap) and cyamemazine (Tercian).

One preferred embodiment of the invention is a combination, wherein the marketed antipsychotic drug is olanzapine (Zyprexa), clozapine (Clozaril), risperidone (Risperdal), aripiprazole (Abilify) or ziprasidone.

Furthermore, the compounds of the present invention can be combined with antidepressants such as selective serotonin reuptake inhibitors [Citalopram (Celexa), Escitalopram (Lexapro, Cipralex), Paroxetine (Paxil, Seroxat), Fluoxetine (Prozac), Fluvoxamine (Luvox), Sertraline (Zoloft, Lustral)], serotonin-norepinephrine reuptake inhibitors [Duloxetine (Cymbalta), Milnacipran (Ixel, Savella), Venlafaxine (Effexor), Desvenlafaxine (Pristiq), Tramadol (Tramal, Ultram), Sibutramine (Meridia, Reductil)], serotonin antagonist and reuptake inhibitors [Etoperidone (Axiomin, Etonin), Lubazodone (YM-992, YM-35,995), Nefazodone (Serzone, Nefadar), Trazodone (Desyrel)], norepinephrine reuptake inhibitors [Reboxetine (Edronax), Viloxazine (Vivalan), Atomoxetine (Strattera)], norepinephrine-dopamine reuptake inhibitors [Bupropion (Wellbutrin, Zyban), Dexmethylphenidate (Focalin), Methylphenidate (Ritalin, Concerta)], norepinephrine-dopamine releasing agents [Amphetamine (Adderall), Dextroamphetamine (Dexedrine), Dextromethamphetamine (Desoxyn), Lisdexamfetamine (Vyvanse)], tricyclic antidepressants [Amitriptyline (Elavil, Endep), Clomipramine (Anafranil), Desipramine (Norpramin, Pertofrane), Dosulepin [Dothiepin] (Prothiaden), Doxepin (Adapin, Sinequan), Imipramine (Tofranil), Lofepramine (Feprapax, Gamanil, Lomont), Nortriptyline (Pamelor), Protriptyline (Vivactil), Trimipramine (Surmontil)], tetracyclic antidepressants [Amoxapine (Asendin), Maprotiline (Ludiomil), Mianserin (Bolvidon, Norval, Tolvon), Mirtazapine (Remeron)], monoamine oxidase inhibitors [Isocarboxazid (Marplan), Moclobemide (Aurorix, Manerix), Phenelzine (Nardil), Selegiline [L-Deprenyl] (Eldepryl, Zelapar, Emsam), Tranylcypromine (Parnate), Pirlindole (Pirazidol)], 5-HT1A Receptor Agonists [Buspirone (Buspar), Tandospirone (Sediel), Vilazodone (Viibryd)], 5-HT2 Receptor Antagonists [Agomelatine (Valdoxan), Nefazodone (Nefadar, Serzone), selective Serotonin Reuptake Enhancers [Tianeptine].

A preferred embodiment of this invention is a combination, wherein the marketed anti-depressive drug is citalopram (Celexa), escitalopram (Lexapro, Cipralex), paroxetine (Paxil, Seroxat), fluoxetine (Prozac), sertraline (Zoloft, Lustral) duloxetine (Cymbalta), milnacipran (Ixel, Savella), venlafaxine (Effexor), or mirtazapine (Remeron).

Compounds can also be combined with anxiolytics such as Alprazolam (Helex, Xanax, Xanor, Onax, Alprox, Restyl, Tafil, Paxal), Bretazenil, Bromazepam (Lectopam, Lexotanil, Lexotan, Bromam), Brotizolam (Lendormin, Dormex, Sintonal, Noctilan), Chlordiazepoxide (Librium, Risolid, Elenium), Cinolazepam (Gerodorm), Clonazepam (Rivotril, Klonopin, Iktorivil, Paxam), Clorazepate (Tranxene, Tranxilium), Clotiazepam (Veratran, Clozan, Rize), Cloxazolam (Sepazon, Olcadil), Delorazepam (Dadumir), Diazepam (Antenex, Apaurin, Apzepam, Apozepam, Hexalid, Pax, Stesolid, Stedon, Valium, Vival, Valaxona), Estazolam (ProSom), Etizolam (Etilaam, Pasaden, Depas), Flunitrazepam (Rohypnol, Fluscand, Flunipam, Ronal, Rohydorm), Flurazepam (Dalmadorm, Dalmane), Flutoprazepam (Restas), Halazepam (Paxipam), Ketazolam (Anxon), Loprazolam (Dormonoct), Lorazepam (Ativan, Temesta, Tavor, Lorabenz), Lormetazepam (Loramet, Noctamid, Pronoctan), Medazepam (Nobrium), Midazolam (Dormicum, Versed, Hypnovel, Dormonid), Nimetazepam (Erimin), Nitrazepam (Mogadon, Alodorm, Pacisyn, Dumolid, Nitrazadon), Nordazepam (Madar, Stilny), Oxazepam (Seresta, Serax, Serenid, Serepax, Sobril, Oxabenz, Oxapax), Phenazepam (Phenazepam), Pinazepam (Domar), Prazepam (Lysanxia, Centrax), Premazepam, Quazepam (Doral), Temazepam (Restoril, Normison, Euhypnos, Temaze, Tenox), Tetrazepam (Mylostan), Triazolam (Halcion, Rilamir), Clobazam (Frisium, Urbanol), Eszopiclone (Lunesta), Zaleplon (Sonata, Starnoc), Zolpidem (Ambien, Nytamel, Stilnoct, Stilnox, Zoldem, Zolnod), Zopiclone (Imovane, Rhovane, Ximovan; Zileze; Zimoclone; Zimovane; Zopitan; Zorclone), Pregabalin (Lyrica) and Gabapentin (Fanatrex, Gabarone, Gralise, Neurontin, Nupentin).

One preferred embodiment of the invention is a combination, wherein the marketed anxiolytic drug is alprazolam (Helex, Xanax, Xanor, Onax, Alprox, Restyl, Tafil, Paxal), chlordiazepoxide (Librium, Risolid, Elenium), clonazepam (Rivotril, Klonopin, Iktorivil, Paxam), diazepam (Antenex, Apaurin, Apzepam, Apozepam, Hexalid, Pax, Stesolid, Stedon, Valium, Vival, Valaxona), Estazolam (ProSom), eszopiclone (Lunesta), zaleplon (Sonata, Starnoc), zolpidem (Ambien, Nytamel, Stilnoct, Stilnox, Zoldem, Zolnod), pregabalin (Lyrica) or gabapentin (Fanatrex, Gabarone, Gralise, Neurontin, Nupentin).

A further object of the invention is a combination with mood stabilizers such as Carbamazepine (Tegretol), Lamotrigine (Lamictal), Lithium (Eskalith, Lithane, Lithobid), and Valproic Acid (Depakote).

Compounds can also be combined with procognitive compounds such as donepezil (Aricept), galantamine (Razadyne), rivastigmine (Exelon) and memantine (Namenda).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

A preferred embodiment of the invention relates to compounds of formula I, wherein

is pyridinyl and

is phenyl, for example the following compounds:
N-(3,3-dimethyl-2-oxo-2,3-dihydro-1H-indol-6-yl)-2-methyl-isonicotinamide (known)
N-(1,3,3-trimethyl-2-oxo-2,3-dihydro-1H-indol-6-yl)-isonicotinamide
N-(1'-methyl-2'-oxospiro[cyclopentane-1,3'-indoline]-6'-yl)isonicotinamide
N-(1,3,3-trimethyl-2-oxoindolin-6-yl)nicotinamide
2-methyl-N-(1,3,3-trimethyl-2-oxoindolin-6-yl)isonicotinamide
N-(1-ethyl-3,3-dimethyl-2-oxoindolin-6-yl)isonicotinamide
4-methyl-N-(1,3,3-trimethyl-2-oxoindolin-6-yl)nicotinamide
6-methoxy-N-(1,3,3-trimethyl-2-oxoindolin-6-yl)nicotinamide
N-(7-fluoro-1,3,3-trimethyl-2-oxoindolin-6-yl)isonicotinamide
N-(1-cyclopropyl-3,3-dimethyl-2-oxoindolin-6-yl)isonicotinamide
3-methoxy-N-(1,3,3-trimethyl-2-oxoindolin-6-yl)isonicotinamide
N-(1-cyclopropyl-3,3-dimethyl-2-oxoindolin-6-yl)-2-methylisonicotinamide
N-(1-cyclopropyl-3,3-dimethyl-2-oxoindolin-6-yl)nicotinamide
4-chloro-N-(1,3,3-trimethyl-2-oxoindolin-6-yl)nicotinamide
N-(5-fluoro-1,3,3-trimethyl-2-oxoindolin-6-yl)isonicotinamide
N-(1-ethyl-3,3-dimethyl-2-oxoindolin-6-yl)nicotinamide
N-(5-fluoro-1,3,3-trimethyl-2-oxoindolin-6-yl)-2-methyl-isonicotinamide
N-(7-fluoro-1,3,3-trimethyl-2-oxoindolin-6-yl)nicotinamide
N-(5-fluoro-1,3,3-trimethyl-2-oxoindolin-6-yl)nicotinamide
2-chloro-N-(1,3,3,7-tetramethyl-2-oxoindolin-6-yl)isonicotinamide
2-chloro-6-methyl-N-(1,3,3-trimethyl-2-oxoindolin-6-yl)nicotinamide
3-chloro-N-(1,3,3-trimethyl-2-oxoindolin-6-yl)isonicotinamide
N-(7-fluoro-1,3,3-trimethyl-2-oxoindolin-6-yl)-2-methyl-isonicotinamide
3-fluoro-N-(1,3,3-trimethyl-2-oxoindolin-6-yl)isonicotinamide
3-chloro-N-(1-cyclopropyl-3,3-dimethyl-2-oxoindolin-6-yl)isonicotinamide
N-(1-cyclopropyl-3,3-dimethyl-2-oxoindolin-6-yl)-3-fluoroisonicotinamide
N-(7-fluoro-1,3,3-trimethyl-2-oxoindolin-6-yl)-6-methylnicotinamide
5-fluoro-2-methyl-N-(1,3,3-trimethyl-2-oxoindolin-6-yl)isonicotinamide
N-(5-chloro-1,3,3-trimethyl-2-oxoindolin-6-yl)isonicotinamide
N-(5-chloro-1,3,3-trimethyl-2-oxoindolin-6-yl)-2-methyl-isonicotinamide
N-(1-cyclopropyl-5-fluoro-3,3-dimethyl-2-oxoindolin-6-yl)isonicotinamide
N-(1-isopropyl-3,3-dimethyl-2-oxoindolin-6-yl)nicotinamide
N-(1-cyclopropyl-5-fluoro-3,3-dimethyl-2-oxoindolin-6-yl)nicotinamide
N-(1-ethyl-3,3-dimethyl-2-oxoindolin-6-yl)-2-methylisonicotinamide
3-chloro-N-(1-ethyl-3,3-dimethyl-2-oxoindolin-6-yl)isonicotinamide
N-(1-ethyl-3,3-dimethyl-2-oxoindolin-6-yl)-3-fluoroisonicotinamide
N-(1-isopropyl-3,3-dimethyl-2-oxo-2,3-dihydro-1H-indol-6-yl)-2-methyl-isonicotinamide
4-fluoro-N-(1,3,3-trimethyl-2-oxoindolin-6-yl)benzamide
3-chloro-N-(1,3,3-trimethyl-2-oxoindolin-6-yl)picolinamide
N-(1-cyclopentyl-3,3-dimethyl-2-oxoindolin-6-yl)-3-fluoroisonicotinamide
N-(1-cyclopropyl-5-fluoro-3,3-dimethyl-2-oxoindolin-6-yl)-2-methylisonicotinamide
N-(5,7-difluoro-1,3,3-trimethyl-2-oxo-2,3-dihydro-1H-indol-6-yl)-isonicotinamide
3-fluoro-N-(5-fluoro-1,3,3-trimethyl-2-oxoindolin-6-yl)isonicotinamide
N-(5,7-difluoro-1,3,3-trimethyl-2-oxo-2,3-dihydro-1H-indol-6-yl)-2-methyl-isonicotinamide
N-(5,7-difluoro-1,3,3-trimethyl-2-oxo-2,3-dihydro-1H-indol-6-yl)-2-methyl-isonicotinamide
3-chloro-N-(5-fluoro-1,3,3-trimethyl-2-oxoindolin-6-yl)isonicotinamide
N-(1-(cyclopropylmethyl)-3,3-dimethyl-2-oxoindolin-6-yl)isonicotinamide
N-(1-(cyclopropylmethyl)-3,3-dimethyl-2-oxoindolin-6-yl)-3-fluoroisonicotinamide
N-(1-cyclopropyl-3,3-dimethyl-2-oxoindolin-6-yl)-5-fluoro-2-methylisonicotinamide
N-(1'-cyclopropyl-2'-oxospiro[cyclopropane-1,3'-indoline]-6'-yl)isonicotinamide
3-chloro-N-(1'-cyclopropyl-2'-oxospiro[cyclopropane-1,3'-indoline]-6'-yl)isonicotinamide
N-(1'-cyclopropyl-2'-oxospiro[cyclopropane-1,3'-indoline]-6'-yl)-3-fluoroisonicotinamide
N-(3,3-dimethyl-1-(oxetan-3-yl)-2-oxoindolin-6-yl)isonicotinamide
N-(3,3-dimethyl-1-(oxetan-3-yl)-2-oxoindolin-6-yl)isonicotinamide
N-(1'-Cyclopropyl-2'-oxospiro[cyclopropane-1,3'-indoline]-6'-yl)-2-methylisonicotinamide
3-Chloro-N-(7-fluoro-1,3,3-trimethyl-2-oxoindolin-6-yl)isonicotinamide
3-Chloro-N-(3,3-dimethyl-1-(oxetan-3-yl)-2-oxoindolin-6-yl)isonicotinamide
N-(3,3-Dimethyl-1-(oxetan-3-yl)-2-oxoindolin-6-yl)-2-methylisonicotinamide
N-(3,3-Dimethyl-1-(oxetan-3-yl)-2-oxoindolin-6-yl)nicotinamide
N-(1-(3-Cyclopropoxypropyl)-3,3-dimethyl-2-oxoindolin-6-yl)-3-fluoroisonicotinamide
N-(1-(3-Cyclopropoxypropyl)-3,3-dimethyl-2-oxoindolin-6-yl)isonicotinamide
3-Fluoro-N-(1-(hydroxymethyl)-3,3-dimethyl-2-oxoindolin-6-yl)isonicotinamide
3-Fluoro-N-(1-(2-hydroxyethyl)-3,3-dimethyl-2-oxoindolin-6-yl)isonicotinamide
3-Fluoro-N-(1-(3-hydroxypropyl)-3,3-dimethyl-2-oxoindolin-6-yl)isonicotinamide
N-(1-(3-(Cyclopropylsulfonyl)propyl)-3,3-dimethyl-2-oxoindolin-6-yl)isonicotinamide N-(1-(3-(Cyclopropylsulfonyl)propyl)-3,3-dimethyl-2-oxoindolin-6-yl)isonicotinamide N-(3,3-Dimethyl-2-oxoindolin-6-yl)-3-fluoroisonicotinamide 3-Chloro-N-(1-(3-hydroxypropyl)-3,3-dimethyl-2-oxoindolin-6-yl)isonicotinamide N-(3,3-Dimethyl-2-oxo-1-(2,2,2-trifluoroethyl)indolin-6-yl)-3-fluoroisonicotinamide or N-(3,3-Dimethyl-1-(2-(methylsulfonyl)ethyl)-2-oxoindolin-6-yl)-3-fluoroisonicotinamide.

A further preferred embodiment of the invention relates to compounds of formula I, wherein

is pyrimidinyl or imidazolyl, and

is phenyl, for example the following compounds:

2,6-dimethyl-N-(1,3,3-trimethyl-2-oxoindolin-6-yl)pyrimidine-4-carboxamide 1-methyl-N-(1,3,3-trimethyl-2-oxoindolin-6-yl)-1H-imidazole-2-carboxamide 2,4-dimethyl-N-(1,3,3-trimethyl-2-oxoindolin-6-yl)pyrimidine-5-carboxamide or 2-methyl-N-(1,3,3-trimethyl-2-oxoindolin-6-yl)pyrimidine-5-carboxamide.

A further preferred embodiment of the invention relates to compounds of formula I, wherein

is pyrimidinyl, isoxazolyl or pyrazolyl, and

is pyridinyl, for example the following compounds:

N-(1-Cyclopropyl-3,3-dimethyl-2-oxo-2,3-dihydro-1H-pyrrolo[3,2-c]pyridin-6-yl)-2-methylpyrimidine-5-carboxamide N-(1-Cyclopropyl-3,3-dimethyl-2-oxo-2,3-dihydro-1H-pyrrolo[3,2-c]pyridin-6-yl)isoxazole-5-carboxamide N-(1-Cyclopropyl-3,3-dimethyl-2-oxo-2,3-dihydro-1H-pyrrolo[3,2-c]pyridin-6-yl)-1-methyl-1H-pyrazole-5-carboxamide N-(1-Cyclopropyl-3,3-dimethyl-2-oxo-2,3-dihydro-1H-pyrrolo[3,2-c]pyridin-6-yl)-1-methyl-1H-pyrazole-3-carboxamide N-(1-Cyclopropyl-3,3-dimethyl-2-oxo-2,3-dihydro-1H-pyrrolo[3,2-c]pyridin-6-yl)-2-methoxypyrimidine-5-carboxamide N-(1-Cyclopropyl-3,3-dimethyl-2-oxo-2,3-dihydro-1H-pyrrolo[3,2-c]pyridin-6-yl)-3-methylisoxazole-4-carboxamide or N-(1-Cyclopropyl-3,3-dimethyl-2-oxo-2,3-dihydro-1H-pyrrolo[3,2-c]pyridin-6-yl)-2-(trifluoromethyl)pyrimidine-5-carboxamide.

A further preferred embodiment of the invention relates to compounds of formula I, wherein

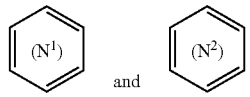

are both pyridinyl, for example the following compounds:

N-(1,3,3-trimethyl-2-oxo-2,3-dihydro-1H-pyrrolo[3,2-c]pyridin-6-yl)isonicotinamide N-(1,3,3-Trimethyl-2-oxo-2,3-dihydro-1H-pyrrolo[2,3-b]pyridin-6-yl)isonicotinamide N-(1,3,3-Trimethyl-2-oxo-2,3-dihydro-1H-pyrrolo[2,3-b]pyridin-6-yl)nicotinamide 2-Methyl-N-(1,3,3-trimethyl-2-oxo-2,3-dihydro-1H-pyrrolo[2,3-b]pyridin-6-yl)isonicotinamide N-(1-Cyclopropyl-3,3-dimethyl-2-oxo-2,3-dihydro-1H-pyrrolo[3,2-c]pyridin-6-yl)isonicotinamide N-(1-Cyclopropyl-3,3-dimethyl-2-oxo-2,3-dihydro-1H-pyrrolo[3,2-c]pyridin-6-yl)nicotinamide N-(1-Cyclopropyl-3,3-dimethyl-2-oxo-2,3-dihydro-1H-pyrrolo[3,2-c]pyridin-6-yl)-2-methylisonicotinamide N-(1-Cyclopropyl-3,3-dimethyl-2-oxo-2,3-dihydro-1H-pyrrolo[2,3-b]pyridin-6-yl)isonicotinamide or 2-Chloro-N-(1-cyclopropyl-3,3-dimethyl-2-oxo-2,3-dihydro-1H-pyrrolo[3,2-c]pyridin-6-yl)isonicotinamide.

The present compounds of formula I and their pharmaceutically acceptable salts can be prepared by methods known in the art, for example, by processes described below, which processes comprise reacting a compound of formula

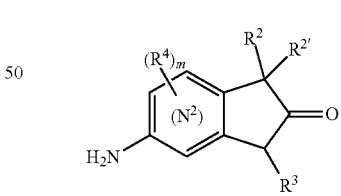

with a compound of formula

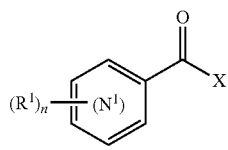

to a compound of formula

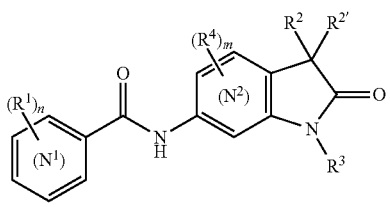

I wherein X is hydroxyl or chlorine and the further groups have the meaning as described above and, if desired, converting the compounds obtained into pharmaceutically acceptable acid addition salts The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

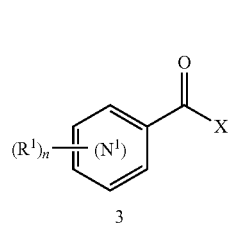

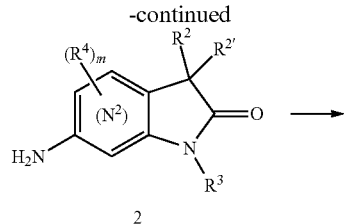

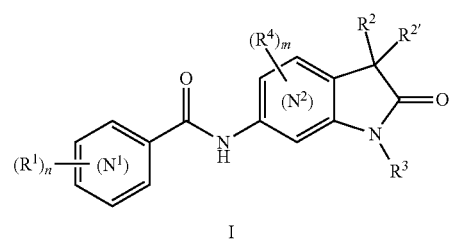

I

The present compounds of formula I and their pharmaceutically acceptable salts can be prepared by acylation of anilines of general formula 2 with activated acids of general formula 3 (see Scheme 1). Acid chlorides (with X=Cl) are either commercially available or can be prepared from the corresponding acids (X=OH) by generally known procedures, e.g. reaction with thionyl chloride or oxalyl chloride. The acid chlorides 3 (with X=Cl) can be reacted with anilines 2 in the presence of a base (e.g. triethylamine, diisopropylethylamine) to provide amides of general formula I. Alternatively amides of formula I can be obtained by in situ activation of acids of general formula 3 (X=OH) with generally known amide coupling reagents like 1-chloro-N,N,2-trimethylpropenylamine, 1-(3-dimethylaminopropyl)-3-ethylcarbodiimide hydrochloride (EDC) or (2-(7-aza-1H-benzotriazole-1-yl)-1,1,3,3-tetramethyluronium hexafluorophosphate (HATU) and reaction with anilines 2.

Scheme 2

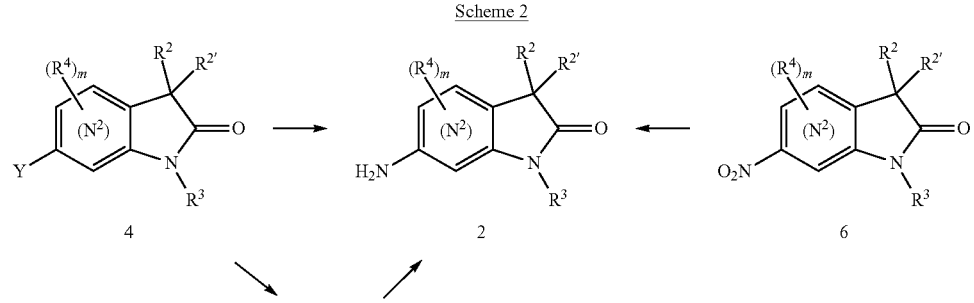

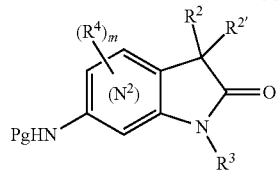

Anilines of general formula 2 are either commercially available or can be prepared by reduction of the corresponding nitro compounds 6 by methods known to one skilled in the art, e.g. hydrogenation in the presence of a catalyst (e.g. palladium on charcoal) or by chemical reduction with e.g. sodium dithionite (see Scheme 2). Alternatively halides 4 can be coupled with ammonia bearing a protecting group like benzyl to substituted anilines 7. This reaction can be accomplished using generally known procedures, e.g. displacement reactions under catalytic conditions (like e.g. palladium(0) or copper(II) catalysis) or under thermal conditions or under basic conditions. Cleavage of the protecting group (e.g. hydrogenation for benzyl) provides anilines 2. Alternatively anilines of general formula 2 can be prepared by coupling of halides of general formula 4 with ammonia under the conditions described above.

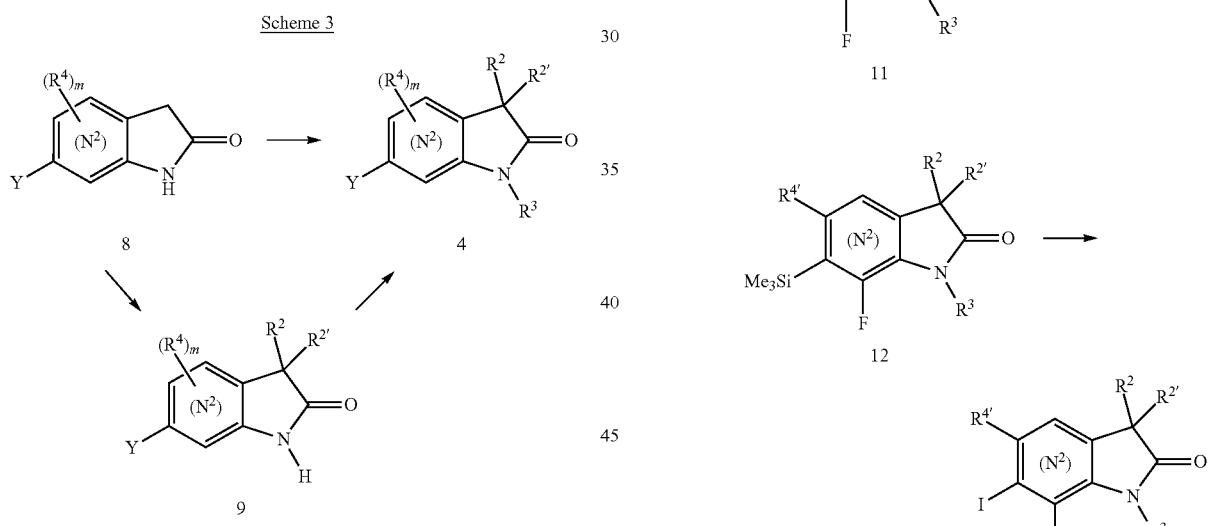

For $R^2=R^{2'}=R^3$ compounds of general formula 4 can e.g. be prepared by trialkylation of 6-halo-oxindoles 8 with $R^{2,2',3}$-LG with LG being a leaving group like iodide, bromide, chloride, tosylate in the presence of a base like sodium hydride (see Scheme 3).

For $R^2=R^{2'}\neq R^3$ compounds of general formula 4 can e.g. be prepared by dialkylation of 6-halo-oxindoles 8 with $R^{2,2'}$-LG (LG being a leaving group like iodide, bromide, chloride, tosylate) in the presence of a base like potassium tert-butoxide and in the presence of copper (I) bromide-dimethylsulfide complex. The dialkylated product 9 can then be converted to compounds 4 by alkylation with $R^3$-LG in the presence of a base like sodium hydride or cesium carbonate or by coupling of boronic acids $R^3$—B(OH)$_2$ or esters $R^3$—B(OR)$_2$ (e.g. $R^3$-4,4,5,5-tetramethyl-[1,3,2]dioxaborolane) under metal catalysis (like e.g. palladium(0) or copper(II) catalysis) in the presence of a base like e.g. sodium bis(trimethylsilyl)amide or sodium carbonate.

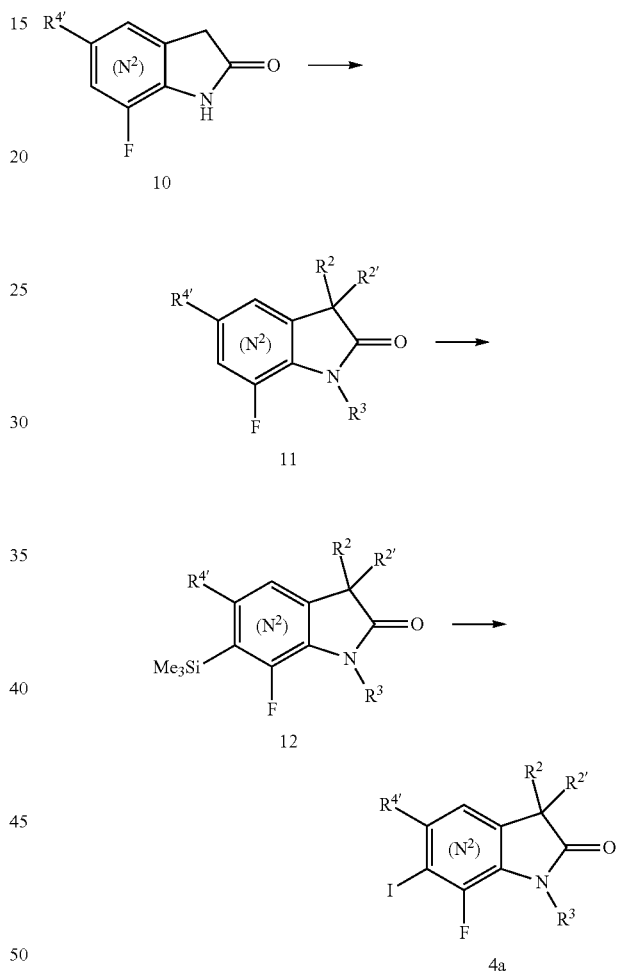

For Y=I, R$^4$=F,

=phenyl and $R^{4'}$=H or F, compounds of general formula 4a can e.g. be prepared by alkylation of oxindole 10 in analogy to Scheme 3, followed by ortho silylation by treatment with LDA and trimethylsilyl chloride followed by exchange of the silyl group with iodide with iodine monochloride (see Scheme 4).

Scheme 5

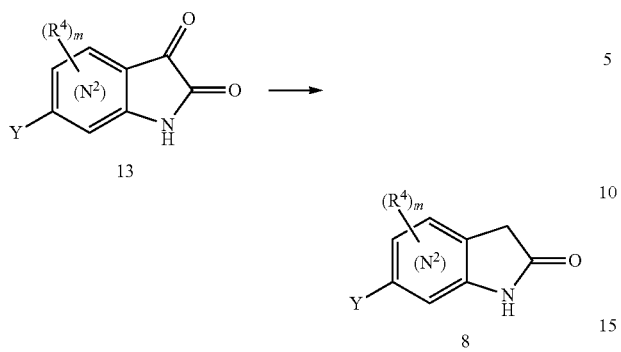

Compounds of general formula 8 can e.g. be prepared by reduction of isatin derivatives 13 with e.g. hydrazine (see Scheme 5).

Scheme 6

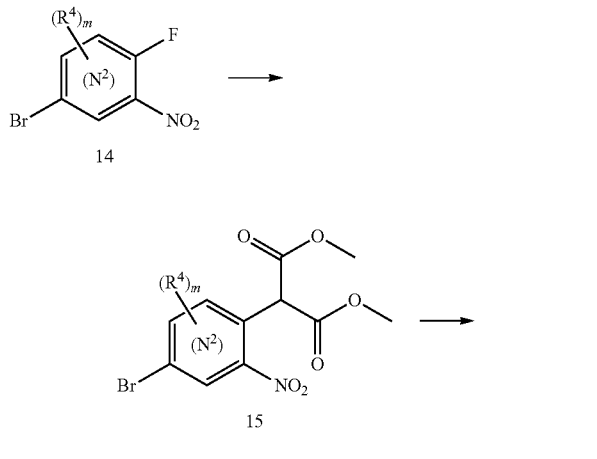

Alternatively compounds of general formula 8a with Y=Br,

=phenyl can e.g. be prepared starting from 4-bromo-1-fluoro-2-nitro-benzene derivatives 14 by nucleophilic substitution of the fluoride with malonate ester in the presence of a base like e.g. sodium hydride (see Scheme 6). Ester hydrolysis and decarboxylation can e.g. be accomplished by heating in the presence hydrochloric acid to provide acid 16. Nitro reduction with e.g. iron in acetic acid is followed by cyclization to lactam 8a.

Example 1

Known

N-(3,3-Dimethyl-2-oxo-2,3-dihydro-1H-indol-6-yl)-2-methyl-isonicotinamide

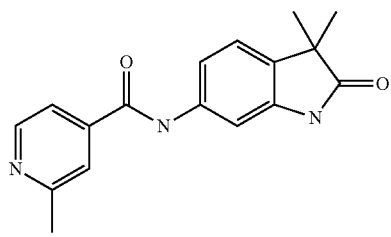

a) 6-Amino-3,3-dimethylindolin-2-one

Palladium on activated carbon (10%, 129 mg, 121 µmol) was added to a solution of 3,3-dimethyl-6-nitroindolin-2-one (J.-P. Hölck et al., 1987, U.S. Pat. No. 4,666,923 A1; 500 mg, 2.42 mmol) in ethyl acetate (100 ml). The mixture was stirred at 70° C. under an hydrogen atmosphere (balloon) for 48 hours. The catalyst was filtered off, washed with ethyl acetate and the solvent was evaporated. The title compound was obtained as orange powder (427 mg).

$^1$H NMR (DMSO-D$_6$, 400 MHz): δ (ppm)=10.75 (s, 1H), 7.92-7.89 (m, 1H), 7.62-7.58 (m, 2H), 1.30 (s, 6H).

b) N-(3,3-Dimethyl-2-oxo-2,3-dihydro-1H-indol-6-yl)-2-methyl-isonicotinamide To a suspension of 2-methylisonicotinic acid (175 mg, 1.28 mmol) in dry toluene (12.8 ml) was added SOCl$_2$ (167 mg, 103 µl, 1.4 mmol) and dry DMF (9.33 mg, 9.89 µl, 128 µmol) under an argon atmosphere. The mixture was heated under reflux for 2 hours and the solvent was evaporated under reduced pressure. The residue was suspended in dry dichloromethane (3.51 ml) and a suspension of 6-amino-3,3-dimethylindolin-2-one (0.15 g, 851 µmol) and DIPEA (330 mg, 446 µl, 2.55 mmol) in dry dichloromethane (5 ml) was added portionwise. The suspension was stirred under an argon atmosphere at room temperature for 16 hours, then diluted with dichloromethane, water and 1 M aqueous sodium carbonate solution. The aqueous phase was extracted with dichloromethane. The combined organic layers were washed with 1 M aqueous sodium carbonate solution, dried over sodium sulfate, the solvent was evaporated and the residue purified by silica gel chromatography using dichloromethane/methanol as eluent. The title compound was obtained as brown solid (99 mg).

MS ESI (m/z): 296.3 [(M+H)$^+$].

$^1$H NMR (DMSO-D$_6$, 400 MHz): δ (ppm)=10.38 (s, 2H), 8.64-8.62 (m, 1H), 7.71 (m, 1H), 7.64-7.62 (m, 1H), 7.49 (m, 1H), 7.31-7.23 (m, 2H), 2.57 (s, 3H), 1.24 (s, 6H).

Example 2

N-(1,3,3-Trimethyl-2-oxo-2,3-dihydro-1H-indol-6-yl)-isonicotinamide

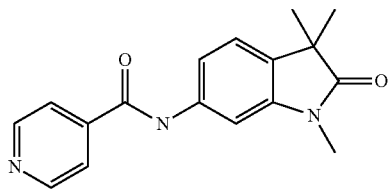 [SMILES: CN1C(=O)C(C)(C)c2ccc(NC(=O)c3ccncc3)cc21]

To a solution of 6-amino-1,3,3-trimethylindolin-2-one (W. von der Saal et al., J. Med. Chem. 1989, 32(7), 1481-1491; 500 mg, 2.63 mmol) in dry dichloromethane (13 ml) were added triethylamine (798 mg, 1.1 ml, 7.88 mmol) and isonicotinoyl chloride hydrochloride (724 mg, 3.94 mmol). The reaction mixture was stirred at room temperature for 16 hours. The reaction mixture was diluted with dichloromethane, water and 1 M aqueous sodium carbonate solution. The aqueous phase was extracted with dichloromethane. The combined organic layers were washed with 1 M aqueous sodium carbonate solution, dried over sodium sulfate, the solvent was evaporated and the residue was purified by silica gel chromatography using dichloromethane/methanol as eluent. The title compound was obtained as brown solid (661 mg).

MS ESI (m/z): 296.3 [(M+H)$^+$].

$^1$H NMR (CDCl$_3$, 400 MHz): δ (ppm)=8.83-8.81 (m, 2H), 8.03 (bs, 1H), 7.74-7.72 (m, 2H), 7.55 (m, 1H), 7.20-7.17 (m, 1H), 7.06-7.02 (m, 1H), 3.24 (s, 3H), 1.37 (s, 6H).

Example 3

N-(1'-Methyl-2'-oxospiro[cyclopentane-1,3'-indoline]-6'-yl)isonicotinamide

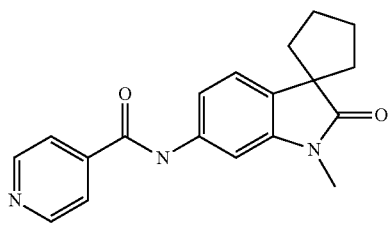

Prepared in analogy to example 2 using 6'-amino-1'-methyl-spiro[cyclopentane-1,3'-indoline]-2'-one (prepared in analogy to procedures described in W. von der Saal et al., J. Med. Chem. 1989, 32(7), 1481-1491 for the preparation of 6-amino-1,3,3-trimethylindolin-2-one by methylation and nitro reduction of 6'-nitro-spiro[cyclopentane-1,3'-indolin]-2'-one (A. Mertens et al. J. Med. Chem. 1987, 30 (8), 1279-1287)). The title compound was obtained as light yellow solid.

MS ESI (m/z): 322.2 [(M+H)$^+$].

$^1$H NMR (CDCl$_3$, 400 MHz): δ (ppm)=8.84-8.82 (m, 2H), 7.90 (bs, 1H), 7.75-7.73 (m, 2H), 7.50 (m, 1H), 7.19-7.16 (m, 1H), 7.04-7.00 (m, 1H), 3.24 (s, 3H), 2.20-1.80 (m, 8H).

Example 4

N-(1,3,3-Trimethyl-2-oxoindolin-6-yl)nicotinamide

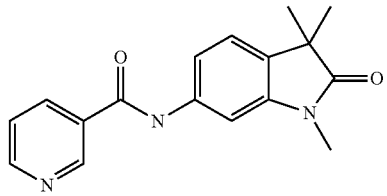 [SMILES: CN1C(=O)C(C)(C)c2ccc(NC(=O)c3cccnc3)cc21]

Prepared in analogy to example 1b from nicotinic acid and 6-amino-1,3,3-trimethylindolin-2-one (W. von der Saal et al., J. Med. Chem. 1989, 32(7), 1481-1491). The title compound was obtained as light yellow solid.

MS ESI (m/z): 296.3 [(M+H)$^+$].

$^1$H NMR (CDCl$_3$, 400 MHz): δ (ppm)=9.12-9.11 (m, 1H), 8.81-8.79 (m, 1H), 8.25-8.21 (m, 1H), 7.96 (bs, 1H), 7.56-7.55 (m, 1H), 7.49-7.45 (m, 1H), 7.20-7.17 (m, 1H), 7.06-7.02 (m, 1H), 3.25 (s, 3H), 1.38 (s, 6H).

Example 5

2-Methyl-N-(1,3,3-trimethyl-2-oxoindolin-6-yl)isonicotinamide

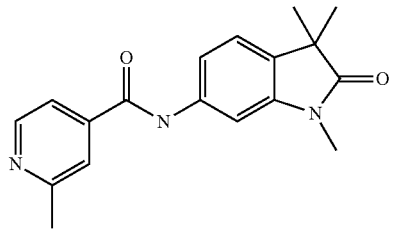

Prepared in analogy to example 1b from 6-amino-1,3,3-trimethylindolin-2-one (W. von der Saal et al., J. Med. Chem. 1989, 32(7), 1481-1491). The title compound was obtained as light brown solid.

MS ESI (m/z): 310.2 [(M+H)$^+$].

$^1$H NMR (CDCl$_3$, 400 MHz): δ (ppm)=8.70-8.68 (m, 1H), 7.88 (bs, 1H), 7.59-7.54 (m, 1H), 7.51-7.49 (m, 1H), 7.20-7.17 (m, 1H), 7.04-7.01 (m, 1H), 3.24 (s, 3H), 2.68 (s, 3H), 1.37 (s, 6H).

Example 6

N-(1,3,3-Trimethyl-2-oxo-2,3-dihydro-1H-pyrrolo[3,2-c]pyridin-6-yl)isonicotinamide

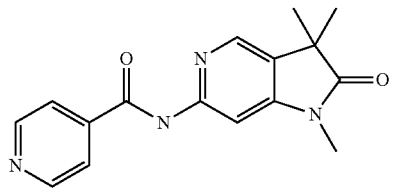 [SMILES: CN1C(=O)C(C)(C)c2cnc(NC(=O)c3ccncc3)cc21]

Prepared in analogy to example 20d, 37b, 37c and 2 from 6-chloro-1,3-dihydro-pyrrolo[3,2-c]pyridin-2-one (P. Eastwood et al., Bioorg. Med. Chem. Lett. 2011, 21(18), 5270-5273). The title compound was obtained as yellow powder.

MS ESI (m/z): 297.3 [(M+H)+].

$^1$H NMR (CDCl$_3$, 400 MHz): δ (ppm)=9.23 (bs, 1H), 8.86-8.84 (m, 2H), 8.03-7.98 (m, 2H), 7.81-7.79 (m, 2H), 3.29 (s, 3H), 1.44 (s, 6H).

Example 7

N-(1-ethyl-3,3-dimethyl-2-oxoindolin-6-yl)isonicotinamide

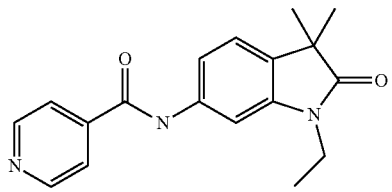 [SMILES: CCN1C(=O)C(C)(C)c2ccc(NC(=O)c3ccncc3)cc21]

Prepared in analogy to example 2 from 6-amino-1-ethyl-3,3-dimethylindolin-2-one (G. Georges et al., US2006/142247 A1). The title compound was obtained as an off-white powder.

MS ESI (m/z): 310.2 [(M+H)+].

$^1$H NMR (CDCl$_3$, 400 MHz): δ (ppm)=8.81-8.79 (m, 2H), 8.23 (bs, 1H), 7.75-7.73 (m, 2H), 7.58 (m, 1H), 7.20-7.17 (m, 1H), 7.07-7.04 (m, 1H), 3.78 (q, J=7.27 Hz, 2H), 1.36 (s, 6H), 1.27 (t, J=7.27 Hz, 3H).

Example 8

2,6-Dimethyl-N-(1,3,3-trimethyl-2-oxoindolin-6-yl)pyrimidine-4-carboxamide

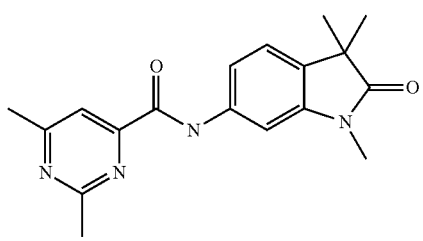 [SMILES: Cc1cc(C(=O)Nc2ccc3c(c2)N(C)C(=O)C3(C)C)nc(C)n1]

Prepared in analogy to example 1b from 6-amino-1,3,3-trimethylindolin-2-one and 2,6-dimethylpyrimidine-4-carboxylic acid. The title compound was obtained as white foam.

MS ESI (m/z): 325.2 [(M+H)+].

$^1$H NMR (CDCl$_3$, 400 MHz): δ (ppm)=9.98 (bs, 1H), 7.88 (m, 1H), 7.65 (m, 1H), 7.20 (m, 2H), 3.27 (s, 3H), 2.81 (s, 3H), 2.64 (s, 3H), 1.38 (s, 6H).

Example 9

4-Methyl-N-(1,3,3-trimethyl-2-oxoindolin-6-yl)nicotinamide

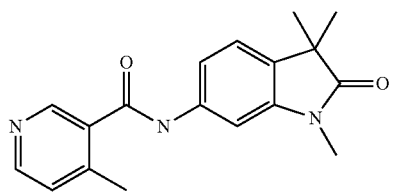 [SMILES: Cc1ccncc1C(=O)Nc1ccc2c(c1)N(C)C(=O)C2(C)C]

Prepared in analogy to example 1b from 6-amino-1,3,3-trimethylindolin-2-one and 4-methylnicotinic acid. The title compound was obtained as red oil.

MS ESI (m/z): 310.2 [(M+H)+].

$^1$H NMR (CDCl$_3$, 400 MHz): δ (ppm)=8.65 (m, 1H), 8.57 (m, 1H), 8.48-8.46 (m, 1H), 7.88 (m, 1H), 7.60 (m, 1H), 7.21-7.16 (m, 2H), 7.10-7.07 (m, 1H), 3.23 (s, 3H), 2.53 (s, 3H), 1.36 (s, 6H).

Example 10

6-Methoxy-N-(1,3,3-trimethyl-2-oxoindolin-6-yl)nicotinamide

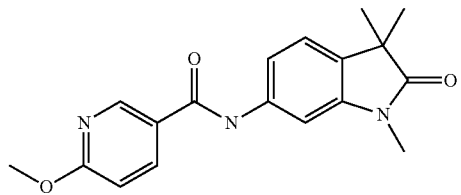 [SMILES: COc1ccc(C(=O)Nc2ccc3c(c2)N(C)C(=O)C3(C)C)cn1]

Prepared in analogy to example 1b from 6-amino-1,3,3-trimethylindolin-2-one and 6-methoxynicotinic acid. The title compound was obtained as light yellow foam.

MS ESI (m/z): 326.2 [(M+H)+].

$^1$H NMR (CDCl$_3$, 400 MHz): δ (ppm)=8.71-8.70 (m, 1H), 8.11-8.07 (m, 1H), 7.74 (bs, 1H), 7.55 (m, 1H), 7.18-7.15 (m, 1H), 7.00-6.97 (m, 1H), 6.86-6.84 (m, 1H), 4.02 (s, 3H), 3.24 (s, 3H), 1.37 (s, 6H).

Example 11

1-Methyl-N-(1,3,3-trimethyl-2-oxoindolin-6-yl)-1H-imidazole-2-carboxamide

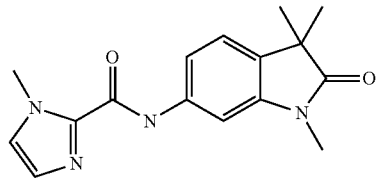 [SMILES: CN1C(=O)C(C)(C)c2ccc(NC(=O)c3nccn3C)cc21]

To a solution of 1-methyl-1H-imidazole-2-carboxylic acid (99.4 mg, 788 µmol) and 6-amino-1,3,3-trimethylindolin-2-one (100 mg, 526 µmol) in DMF (3 ml) were added HATU (400 mg, 1.05 mmol) and DIPEA (347 mg, 468 µl, 2.63 mmol). The reaction mixture was stirred for 3 hours at room temperature and then poured into ethyl acetate and 1 M aqueous sodium carbonate solution. The aqueous phase was extracted with ethyl acetate. The combined organic layers were dried over sodium sulfate and the solvent was removed under reduced pressure. The crude material was purified by silica gel chromatography using ethyl acetate/heptane as eluent followed by reversed phase preparative HPLC. The title compound was obtained as off-white crystals (135 mg).

MS ESI (m/z): 299.1 [(M+H)+].

$^1$H NMR (CDCl$_3$, 400 MHz): δ (ppm)=9.30 (bs, 1H), 7.53-7.52 (m, 1H), 7.17-7.14 (m, 1H), 7.09-7.04 (m, 3H), 4.12 (s, 3H), 3.24 (s, 3H), 1.37 (s, 6H).

Example 12

2,4-Dimethyl-N-(1,3,3-trimethyl-2-oxoindolin-6-yl)pyrimidine-5-carboxamide

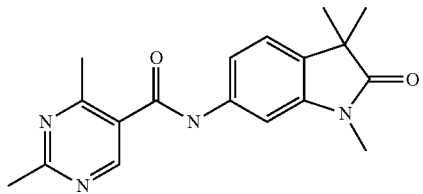

Prepared in analogy to example 11 from 2,4-dimethylpyrimidine-5-carboxylic acid. The title compound was obtained as white foam.

MS ESI (m/z): 325.3 [(M+H)+].

$^1$H NMR (CDCl$_3$, 400 MHz): δ (ppm)=8.72 (m, 1H), 7.56-7.52 (m, 2H), 7.20-7.17 (m, 1H), 6.99-6.96 (m, 1H), 3.25 (s, 3H), 2.76 (s, 3H), 2.71 (s, 3H), 1.37 (s, 6H).

Example 13

N-(7-fluoro-1,3,3-trimethyl-2-oxoindolin-6-yl)isonicotinamide

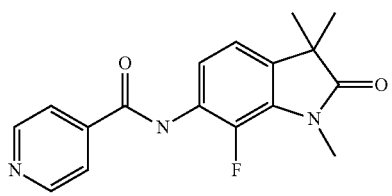 [SMILES: CN1C(=O)C(C)(C)c2ccc(NC(=O)c3ccncc3)c(F)c21]

a) 7-Fluoro-1,3,3-trimethylindolin-2-one

To a suspension of NaH (8.79 g, 220 mmol) in tetrahydrofuran (100 ml) was added 7-fluoroindolin-2-one (8.30 g, 54.9 mmol) in portion within 20 minutes. The reaction mixture was stirred for 30 minutes. MeI (31.2 g, 13.7 ml, 220 mmol) was added dropwise at 24-27° C. within 1.5 hours. The reaction mixture was stirred at room temperature for 3 hours. The reaction mixture was very carefully quenched with 20 ml saturated aqueous ammonium chloride solution at 10-15° C., then diluted with tert-butyl methyl ether and water. The aqueous phase was extracted with tert-butyl methyl ether, the combined organic phases were washed with brine and dried over sodium sulfate. The solvent was evaporated and the residue purified by silica gel chromatography using ethyl acetate/heptane as eluent. The title compound was obtained as orange crystals (9.91 g).

MS ESI (m/z): 194.3 [(M+H)+].

$^1$H NMR (CDCl$_3$, 400 MHz): δ (ppm)=6.99-6.97 (m, 3H), 3.43 (d, J=2.62 Hz, 3H), 1.37 (s, 6H).

b) 7-Fluoro-1,3,3-trimethyl-6-(trimethylsilyl)indolin-2-one

A solution of diisopropylamine (5.4 g, 7.6 ml, 52.8 mmol) in dry tetrahydrofuran (23 ml) under an argon atmosphere was cooled to −40° C. and a solution of n-BuLi (1.6 M in hexane, 31.6 ml, 50.5 mmol) was added dropwise. The mixture was stirred at −40° C. for 30 minutes and then added to a solution of 7-fluoro-1,3,3-trimethylindolin-2-one (8.875 g, 45.9 mmol) and trimethylsilyl chloride (5.49 g, 6.46 ml, 50.5 mmol) in dry tetrahydrofuran (69 ml) at −75° C. The reaction mixture was warmed to room temperature within 16 hours. The reaction mixture was carefully quenched with water (2 ml) and diluted with ethyl acetate and water. The aqueous phase was extracted ethyl acetate, the combined organic phases were washed with brine and dried over sodium sulfate. The solvent was evaporated and the residue purified by silica gel chromatography using ethyl acetate/heptane as eluent. The title compound was obtained as light yellow oil (8.55 g).

MS ESI (m/z): 266.2 [(M+H)+].

$^1$H NMR (CDCl$_3$, 400 MHz): δ (ppm)=7.06-7.02 (m, 1H), 6.99-6.96 (m, 1H), 3.44 (d, J=3.03 Hz, 3H), 1.36 (s, 6H), 0.33 (s, 9H).

c) 7-Fluoro-6-iodo-1,3,3-trimethylindolin-2-one

To a solution of 7-fluoro-1,3,3-trimethyl-6-(trimethylsilyl)indolin-2-one (9.9 g, 37.3 mmol) in dichloromethane (500 ml) at 0° C. was added iodine monochloride (37.3 ml, 37.3 mmol). The reaction mixture was warmed to room temperature and stirred for 16 hours. A saturated aqueous solution of sodium thiosulfate was added to the reaction mixture and the aqueous phase was extracted with dichloromethane. The combined organic layers were dried over sodium sulfate. The solvent was evaporated and the residue purified by silica gel chromatography using ethyl acetate/heptane as eluent. The title compound was obtained as off-white crystals (9.82 g).

$^1$H NMR (CDCl$_3$, 400 MHz): δ (ppm)=7.43-7.39 (m, 1H), 6.77-6.75 (m, 1H), 3.42 (d, J=3.23 Hz, 3H), 1.36 (s, 6H).

d) 6-Amino-7-fluoro-1,3,3-trimethylindolin-2-one

Prepared in analogy to example 20e and 37c from 7-fluoro-6-iodo-1,3,3-trimethylindolin-2-one. The title compound was obtained as white crystals.

MS ESI (m/z): 209.3 [(M+H)+].

$^1$H NMR (CDCl$_3$, 400 MHz): δ (ppm)=6.75-6.73 (m, 1H), 6.45-6.40 (m, 1H), 3.73 (bs, 2H), 3.42-3.41 (m, 3H), 1.32 (s, 6H).

e) N-(7-fluoro-1,3,3-trimethyl-2-oxoindolin-6-yl)isonicotinamide

Prepared in analogy to example 2 from 6-amino-7-fluoro-1,3,3-trimethylindolin-2-one. The title compound was obtained as white solid.

MS ESI (m/z): 314.0 [(M+H)⁺].
¹H NMR (CDCl₃, 400 MHz): δ (ppm)=8.86-8.84 (m, 2H), 8.01-8.00 (m, 2H), 7.74-7.72 (m, 2H), 7.05-7.02 (m, 1H), 3.45-3.44 (m, 3H), 1.39 (s, 6H).

Example 14

N-(1-Cyclopropyl-3,3-dimethyl-2-oxoindolin-6-yl)isonicotinamide

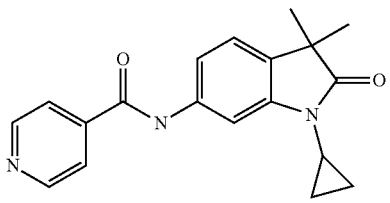 [SMILES: CC1(C)C(=O)N(C2CC2)c2cc(NC(=O)c3ccncc3)ccc21]

a) 6-Bromo-3,3-dimethyl-1,3-dihydro-indol-2-one

To a suspension of potassium tert-butylate (12.8 g, 114 mmol) in dry THF (80 ml) at 0° C. under an argon atmosphere was added portionwise 6-bromoindolin-2-one (5.0 g, 22.9 mmol) followed by copper(I) bromide-dimethylsulfide complex (470 mg, 2.29 mmol). MeI (6.82 g, 3.00 ml, 48.0 mmol) was added dropwise within 45 minutes, keeping temperature of the reaction mixture below 8° C. The reaction mixture was warmed to room temperature and kept at this temperature for 16 hours. The reaction mixture was cooled to 0° C. again and saturated aqueous ammonium chloride solution was cautiously added. The mixture was diluted with tert-butyl methyl ether and water. The aqueous phase was extracted with tert-butyl methyl ether, the combined organic phases were dried over sodium sulfate, the solvent was evaporated and the residue purified by silica gel chromatography using ethyl acetate/heptane as eluent. The title compound was obtained as light yellow solid (5.17 g).
MS ESI (m/z): 240.0/242.1 [(M+H)⁺].
¹H NMR (CDCl₃, 400 MHz): δ (ppm)=8.12 (m, 1H), 7.20-7.16 (m, 1H), 7.09-7.08 (m, 1H), 7.06-7.04 (m, 1H), 1.39 (s, 6H).

b) 6-Bromo-1-cyclopropyl-3,3-dimethyl-1,3-dihydro-indol-2-one

To a suspension of 6-bromo-3,3-dimethylindolin-2-one (4.85 g, 20.2 mmol), cyclopropyl boronic acid (3.47 g, 40.4 mmol), DMAP (7.55 g, 60.6 mmol) and copper(II) acetate (3.85 g, 21.2 mmol) in dry toluene (400 ml), was added a 2 M solution of sodium bis(trimethylsilyl)amide in THF (10.6 ml, 21.2 mmol). The reaction mixture was heated to 95° C. while bubbling dry air through the mixture for 16 hours.
The reaction mixture was diluted with tert-butyl methyl ether, quenched with water and acidified with 1 M HCl. The aqueous phase was extracted with tert-butyl methyl ether. The combined organic layers were washed with 1 M HCl and brine and dried over sodium sulfate. The solvent was evaporated and the residue purified by silica gel chromatography using ethyl acetate/heptane as eluent. The title compound was obtained as red solid (5.12 g).
MS ESI (m/z): 280.1/282.1 [(M+H)⁺].

¹H NMR (CDCl₃, 400 MHz): δ (ppm)=7.24 (m, 1H), 7.20-7.17 (m, 1H), 7.04-7.02 (m, 1H), 2.66-2.58 (m, 1H), 1.32 (s, 6H), 1.11-1.04 (m, 2H), 0.92-0.86 (m, 2H).

c) 6-Amino-1-cyclopropyl-3,3-dimethyl-1,3-dihydro-indol-2-one

Prepared in analogy to example 37b-c from 6-bromo-1-cyclopropyl-3,3-dimethyl-1,3-dihydro-indol-2-one. The title compound was obtained as brown solid.
MS ESI (m/z): 217.3 [(M+H)⁺].
¹H NMR (CDCl₃, 400 MHz): δ (ppm)=6.95-6.92 (m, 1H), 6.49 (m, 1H), 6.37-6.34 (m, 1H), 3.72 (bs, 2H), 2.63-2.56 (m, 1H), 1.29 (s, 6H), 1.06-0.99 (m, 2H), 0.91-0.86 (m, 2H).

d) N-(1-Cyclopropyl-3,3-dimethyl-2-oxoindolin-6-yl)isonicotinamide

Prepared in analogy to example 2 from 6-amino-1-cyclopropyl-3,3-dimethyl-1,3-dihydro-indol-2-one. The title compound was obtained as brown powder.
MS ESI (m/z): 322.2 [(M+H)⁺].
¹H NMR (DMSO-D₆, 400 MHz): δ (ppm)=10.54 (s, 1H), 8.81-8.79 (m, 2H), 7.88-7.86 (m, 2H), 7.69 (m, 1H), 7.46-7.43 (m, 1H), 7.31-7.28 (m, 1H), 2.73-2.66 (m, 1H), 1.23 (s, 6H), 1.04-0.97 (m, 2H), 0.81-0.76 (m, 2H).

Example 15

3-Methoxy-N-(1,3,3-trimethyl-2-oxoindolin-6-yl)isonicotinamide

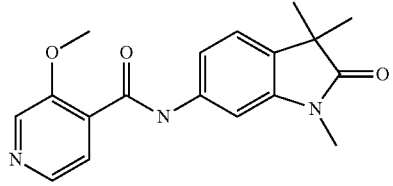 [SMILES: COc1cnccc1C(=O)Nc1ccc2c(c1)N(C)C(=O)C2(C)C]

Prepared in analogy to example 11 from 3-methoxyisonicotinic acid. The title compound was obtained as off-white crystals.
MS ESI (m/z): 326.3 [(M+H)⁺].
¹H NMR (CDCl₃, 400 MHz): δ (ppm)=9.69 (bs, 1H), 8.55 (m, 1H), 8.50-8.49 (m, 1H), 8.10-8.09 (m, 1H), 7.63 (m, 1H), 7.18-7.16 (m, 1H), 7.00-6.97 (m, 1H), 4.21 (s, 3H), 3.26 (s, 3H), 1.38 (s, 6H).

Example 16

2-Methyl-N-(1,3,3-trimethyl-2-oxoindolin-6-yl)pyrimidine-5-carboxamide

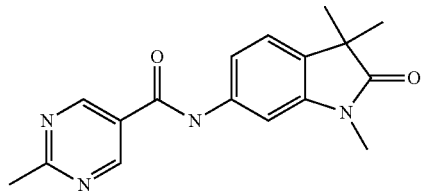 [SMILES: Cc1ncc(C(=O)Nc2ccc3c(c2)N(C)C(=O)C3(C)C)cn1]

Prepared in analogy to example 11 from 2-methylpyrimidine-5-carboxylic acid. The title compound was obtained as light yellow crystals.

MS ESI (m/z): 311.4 [(M+H)+].

$^1$H NMR (CDCl$_3$, 400 MHz): δ (ppm)=9.12 (m, 2H), 7.88 (bs, 1H), 7.52-7.51 (m, 1H), 7.20-7.18 (m, 1H), 7.05-7.02 (m, 1H), 3.24 (s, 3H), 2.84 (s, 3H), 1.38 (s, 6H).

Example 17

N-(1-Cyclopropyl-3,3-dimethyl-2-oxoindolin-6-yl)-2-methylisonicotinamide

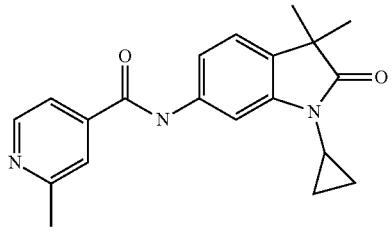 [SMILES: Cc1cc(C(=O)Nc2ccc3c(c2)N(C2CC2)C(=O)C3(C)C)ccn1]

To a solution of 2-methylisonicotinic acid (95.1 mg, 694 µmol) in dry dichloromethane (3.64 ml) under an argon atmosphere at 0° C. was added a solution of 1-chloro-N,N,2-trimethylpropenylamine (104 mg, 763 µmol) in dry dichloromethane (1 ml). After 2 hours 6-amino-1-cyclopropyl-3,3-dimethyl-1,3-dihydro-indol-2-one (example 14c, 150 mg, 694 µmol) and triethyl amine (140 mg, 193 µl, 1.39 mmol) were added at 0° C. The reaction mixture was warmed to room temperature, kept at this temperature for 16 hours, then diluted with dichloromethane, water and 1 M aqueous sodium carbonate solution. The aqueous phase was extracted with dichloromethane. The combined organic layers were washed with 1 M aqueous sodium carbonate solution, dried over sodium sulfate, the solvent was evaporated and the residue was purified by silica gel chromatography using dichloromethane/methanol as eluent. The title compound was obtained as light yellow oil (207 mg).

MS ESI (m/z): 336.3 [(M+H)+].

$^1$H NMR (CDCl$_3$, 400 MHz): δ (ppm)=8.68-8.67 (m, 1H), 8.05 (bs, 1H), 7.69 (m, 1H), 7.61 (m, 1H), 7.53-7.51 (m, 1H), 7.18-7.10 (m, 2H), 2.70-2.62 (m, 1H), 2.67 (s, 3H), 1.34 (s, 6H), 1.12-1.06 (m, 2H), 0.95-0.89 (m, 2H).

Example 18

N-(1-Cyclopropyl-3,3-dimethyl-2-oxoindolin-6-yl)nicotinamide

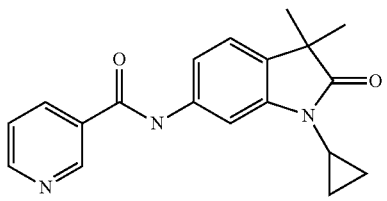 [SMILES: CC1(C)C(=O)N(C2CC2)c2cc(NC(=O)c3cccnc3)ccc21]

Prepared in analogy to example 17 from nicotinic acid. The title compound was obtained as yellow solid.

MS ESI (m/z): 322.2 [(M+H)+].

$^1$H NMR (CDCl$_3$, 400 MHz): δ (ppm)=9.13-9.12 (m, 1H), 8.79-8.77 (m, 1H), 8.27-8.23 (m, 2H), 7.70 (m, 1H), 7.48-7.44 (m, 1H), 7.18-7.15 (m, 2H), 2.70-2.63 (m, 1H), 1.34 (s, 6H), 1.12-1.06 (m, 2H), 0.95-0.89 (m, 2H).

Example 19

4-Chloro-N-(1,3,3-trimethyl-2-oxoindolin-6-yl)nicotinamide

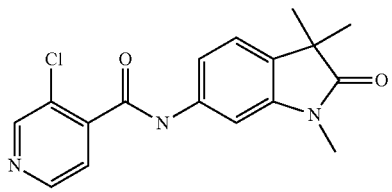 [SMILES: CN1C(=O)C(C)(C)c2ccc(NC(=O)c3ccncc3Cl)cc21]

Prepared in analogy to example 1b from 4-chloronicotinic acid. The title compound was obtained as light brown solid.

MS ESI (m/z): 330.2/332.2 [(M+H)+].

$^1$H NMR (CDCl$_3$, 400 MHz): δ (ppm)=8.96 (s, 1H), 8.62-8.61 (m, 1H), 8.01 (bs, 1H), 7.57-7.56 (m, 1H), 7.45-7.43 (m, 1H), 7.20-7.17 (m, 1H), 7.04-7.00 (m, 1H), 3.25 (s, 3H), 1.37 (s, 6H).

Example 20

N-(5-Fluoro-1,3,3-trimethyl-2-oxoindolin-6-yl)isonicotinamide

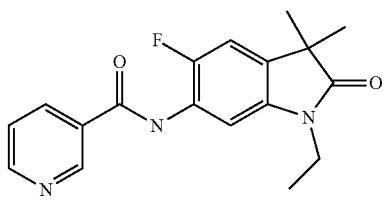 [SMILES: CCN1C(=O)C(C)(C)c2cc(F)c(NC(=O)c3cccnc3)cc21]

a) 2-(4-Bromo-5-fluoro-2-nitro-phenyl)-malonic acid dimethyl ester/2-(2-Bromo-5-fluoro-4-nitro-phenyl)-malonic acid dimethyl ester A suspension of NaH (60% in mineral oil, 20.2 g, 504 mmol) in dioxane (233 ml) was cooled to 11° C. A solution of 1-bromo-2,4-difluoro-5-nitrobenzene (50 g, 26.5 ml, 210 mmol) and dimethyl malonate (33.3 g, 28.9 ml, 242 mmol) in dioxane (467 ml) was carefully added at 11-14° C. within 45 minutes (gas evolution). After completion of the addition the reaction mixture was kept at 12° C. for another hour and then warmed to room temperature. After 16 hours the reaction mixture was cooled to 10° C. and 100 ml saturated aqueous ammonium chloride solution was added. The reaction mixture was diluted with tert-butyl methyl ether, water and saturated aqueous ammonium chloride solution. The aqueous phase was extracted with tert-butyl methyl ether, the combined organic phases were washed with saturated aqueous ammonium chloride solution and brine and dried over sodium sulfate. The solvent was evaporated and the residue purified by silica gel chromatography using ethyl acetate/heptane as eluent. The title compounds were obtained as yellow liquid (53.7 g) as a 2.6:1 mixture and used for the next reaction without further purification.

MS ESI (m/z): 348.1/350.3 [(M−H)−].

$^1$H NMR (CDCl$_3$, 400 MHz) of 2-(4-Bromo-5-fluoro-2-nitro-phenyl)-malonic acid dimethyl ester: δ (ppm)=8.37-8.35 (m, 1H), 7.36-7.33 (m, 1H), 5.36 (s, 1H), 3.82 (s, 6H).

$^1$H NMR (CDCl$_3$, 400 MHz) of 2-(2-Bromo-5-fluoro-4-nitro-phenyl)-malonic acid dimethyl ester: δ (ppm)=8.33-8.30 (m, 1H), 7.60-7.56 (m, 1H), 5.27 (s, 1H), 3.76 (s, 6H).

b) (4-Bromo-5-fluoro-2-nitrophenyl)-acetic acid/(2-Bromo-5-fluoro-4-nitro-phenyl)-acetic acid A mixture of 2-(4-bromo-5-fluoro-2-nitro-phenyl)-malonic acid dimethyl ester/2-(2-bromo-5-fluoro-4-nitro-phenyl)-malonic acid dimethyl ester (2.6:1 mixture, 53.7 g, 153 mmol) and 6 M aqueous hydrochloric acid (767 ml) was heated to reflux for 7 hours and then cooled to 5° C. The precipitate was filtered, washed with water and with n-pentane and then coevaporated 3 times with toluene to give 25.9 g of a mixture of the title compounds as white solid. The mother liquor was extracted with ethyl acetate and the combined organic phases dried over sodium sulfate. The solvent was evaporated and the residue triturated with n-pentane and then coevaporated with toluene to give 11.42 g of a mixture of the title compounds as an off-white solid. This material was combined with the first crop to give a total of 37.32 g of the title compounds as a 2.6:1 mixture which was used for the next reaction without further purification.

MS ESI (m/z): 232.0/233.9 [(M-CO$_2$—H)−].

$^1$H NMR (DMSO-D$_6$, 400 MHz) of 2-(4-Bromo-5-fluoro-2-nitrophenyl)acetic acid: δ (ppm)=8.50-8.47 (m, 1H), 7.70-7.67 (m, 1H), 4.00 (s, 2H).

$^1$H NMR (DMSO-D$_6$, 400 MHz) of (2-Bromo-5-fluoro-4-nitro-phenyl)-acetic acid: δ (ppm)=8.40-8.37 (m, 1H), 7.78-7.74 (m, 1H), 3.87 (s, 2H).

c) 6-Bromo-5-fluoroindolin-2-one

A suspension of (4-bromo-5-fluoro-2-nitrophenyl)-acetic acid/(2-bromo-5-fluoro-4-nitro-phenyl)-acetic acid (2.6:1 mixture, 37.3 g, 134 mmol) and iron (30.0 g, 537 mmol) in acetic acid (671 ml) was heated to 100° C. for 7 hours and then cooled to room temperature. Remaining elemental iron was removed with a magnetic rod. Ice water (900 ml) was added to the reaction mixture. The precipitate was filtered off, washed four times with water and then suspended in an ice-cold aqueous solution of 25% HCl (300 ml) and conc. HCl (50 ml). After stirring for 10 minutes the precipitate was filtered off and washed four times with water.

The precipitate was suspended in a mixture of 1 M aqueous Na$_2$CO$_3$ (400 ml) solution and 0.1 M NaOH (100 ml) and stirred for 40 minutes. The precipitate was filtered off and washed four times with 0.1 M aqueous NaOH, three times with water and once with diisopropylether to give title compound as light grey solid (20.5 g).

MS ESI (m/z): 228.0/230.0 [(M−H)−].

$^1$H NMR (DMSO-D$_6$, 400 MHz): δ (ppm)=10.47 (bs, 1H), 7.31-7.28 (m, 1H), 7.01-6.99 (m, 1H), 3.49 (s, 2H).

d) 6-Bromo-5-fluoro-1,3,3-trimethylindolin-2-one

To a suspension of NaH (5.04 g, 126 mmol) in tetrahydrofuran (105 ml) under an argon atmosphere was added 6-bromo-5-fluoroindolin-2-one (7.24 g, 31.5 mmol) in portions. After gas evolution has ceased methyl iodide (17.9 g, 7.88 ml, 126 mmol) was added dropwise within 50 minutes by means of a syringe pump (exothermic reaction), keeping the temperature of the reaction mixture between 24° C. and 26° C. The reaction mixture was kept at room temperature for 4 hours and then carefully quenched with aqueous ammonium chloride solution.

The reaction mixture was diluted with tert-butyl methyl ether, water and saturated aqueous ammonium chloride solution. The aqueous phase was extracted with tert-butyl methyl ether, the combined organic phases were washed with saturated aqueous ammonium chloride and dried over sodium sulfate. The solvent was evaporated and the residue was triturated with heptane to give the title compound as light brown solid (7.87 g).

$^1$H NMR (CDCl$_3$, 400 MHz): δ (ppm)=7.02-6.97 (m, 2H), 3.19 (s, 3H), 1.36 (s, 6H).

e) 6-(Benzylamino)-5-fluoro-1,3,3-trimethylindolin-2-one

To a solution of 6-bromo-5-fluoro-1,3,3-trimethylindolin-2-one (2.8 g, 10.3 mmol) in tetrahydrofuran (280 ml) under an argon atmosphere were added 2,2'-bis(diphenylphosphino)-1,1'-binaphthyl (320 mg, 514 µmol), tris(dibenzylideneacetone)dipalladium(0) (471 mg, 514 µmol), benzylamine (2.21 g, 2.25 ml, 20.6 mmol) and a 1 M solution of lithium bis(trimethylsilyl)amide (25.7 ml, 25.7 mmol). The reaction mixture was heated to 80° C. in the microwave for 45 minutes and then diluted with ethyl acetate, water and 2 N aqueous Na$_2$CO$_3$ solution. The aqueous phase was extracted with ethyl acetate. The combined organic phases were washed with brine, dried over sodium sulfate. The solvent was evaporated and the residue purified by silica gel chromatography using ethyl acetate/heptane as eluent. The title compound was obtained as light yellow powder (1.57 g).

MS ESI (m/z): 299.3 [(M+H)+].

$^1$H NMR (CDCl$_3$, 400 MHz): δ (ppm)=7.41-7.29 (m, 5H), 6.89-6.85 (m, 1H), 6.20-6.18 (m, 1H), 4.40 (s, 2H), 4.38 (bs, 1H), 3.11 (s, 3H), 1.31 (s, 6H).

f) 6-Amino-5-fluoro-1,3,3-trimethylindolin-2-one

Prepared in analogy to example 37 c from 6-(benzylamino)-5-fluoro-1,3,3-trimethylindolin-2-one. The title compound was obtained as light yellow solid.

MS ESI (m/z): 209.1 [(M+H)+].

g) N-(5-Fluoro-1,3,3-trimethyl-2-oxoindolin-6-yl)isonicotinamide

Prepared in analogy to example 17 from 6-amino-5-fluoro-1,3,3-trimethylindolin-2-one and isonicotinic acid. The title compound was obtained as white powder.

MS ESI (m/z): 314.0 [(M+H)+].

$^1$H NMR (CDCl$_3$, 400 MHz): δ (ppm)=8.87-8.85 (m, 2H), 8.13 (bs, 1H), 8.06-8.04 (m, 1H), 7.75-7.73 (m, 2H), 7.07-7.03 (m, 1H), 3.26 (s, 3H), 1.37 (s, 6H).

Example 21

N-(1-Ethyl-3,3-dimethyl-2-oxoindolin-6-yl)nicotinamide

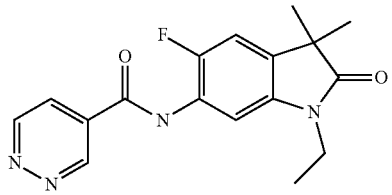 [SMILES: CCN1C(=O)C(C)(C)c2cc(F)c(NC(=O)c3ccnnc3)cc21]

Prepared in analogy to example 17 from 6-amino-1-ethyl-3,3-dimethylindolin-2-one (G. Georges et al., US2006/142247 A1) and nicotinic acid. The title compound was obtained as white solid.

MS ESI (m/z): 310.2 [(M+H)$^+$].

$^1$H NMR (CDCl$_3$, 400 MHz): δ (ppm)=8.81-8.79 (m, 2H), 8.23 (bs, 1H), 7.75-7.73 (m, 2H), 7.58 (m, 1H), 7.20-7.17 (m, 1H), 7.07-7.04 (m, 1H), 3.78 (q, J=7.27 Hz, 2H), 1.36 (s, 6H), 1.27 (t, J=7.27 Hz, 3H).

Example 22

N-(5-fluoro-1,3,3-trimethyl-2-oxoindolin-6-yl)-2-methylisonicotinamide

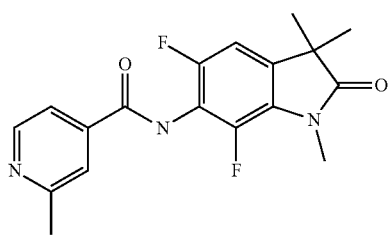 [SMILES: Cc1cc(C(=O)Nc2c(F)cc3c(c2F)N(C)C(=O)C3(C)C)ccn1]

Prepared in analogy to example 17 from 6-amino-5-fluoro-1,3,3-trimethylindolin-2-one (example 20 f). The title compound was obtained as white powder.

MS ESI (m/z): 328.2 [(M+H)$^+$].

$^1$H NMR (CDCl$_3$, 400 MHz): δ (ppm)=8.73-8.71 (m, 1H), 8.10 (bs, 1H), 8.06-8.04 (m, 1H), 7.59 (m, 1H), 7.52-7.50 (m, 1H), 7.06-7.03 (m, 1H), 3.26 (s, 3H), 2.69 (s, 3H), 1.37 (s, 6H).

Example 23

N-(7-fluoro-1,3,3-trimethyl-2-oxoindolin-6-yl)nicotinamide

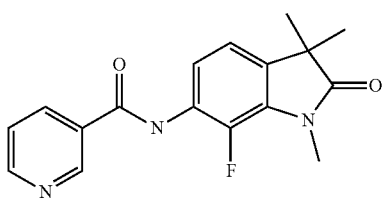 [SMILES: CN1C(=O)C(C)(C)c2ccc(NC(=O)c3cccnc3)c(F)c21]

Prepared in analogy to example 26 from 6-amino-7-fluoro-1,3,3-trimethylindolin-2-one (example 13d) and nicotinic acid. The title compound was obtained as off-white crystals.

MS ESI (m/z): 314.2 [(M+H)$^+$].

$^1$H NMR (CDCl$_3$, 400 MHz): δ (ppm)=9.13 (m, 1H), 8.83-8.81 (m, 1H), 8.25-8.21 (m, 1H), 8.02-7.97 (m, 2H), 7.51-7.46 (m, 1H), 7.04-7.02 (m, 1H), 3.45 (m, 3H), 1.39 (s, 6H).

Example 24

N-(5-fluoro-1,3,3-trimethyl-2-oxoindolin-6-yl)nicotinamide

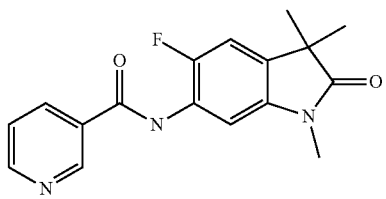 [SMILES: CN1C(=O)C(C)(C)c2cc(F)c(NC(=O)c3cccnc3)cc21]

Prepared in analogy to example 17 from 6-amino-5-fluoro-1,3,3-trimethylindolin-2-one (example 20 f) and nicotinic acid. The title compound was obtained as off-white solid.

$^1$H NMR (CDCl$_3$, 400 MHz): δ (ppm)=9.14 (m, 1H), 8.84-8.82 (m, 1H), 8.24-8.21 (m, 1H), 8.09 (bs, 1H), 8.06-8.04 (m, 1H), 7.52-7.47 (m, 1H), 7.06-7.03 (m, 1H), 3.26 (s, 3H), 1.37 (s, 6H).

Example 25

2-Chloro-N-(1,3,3,7-tetramethyl-2-oxoindolin-6-yl)isonicotinamide

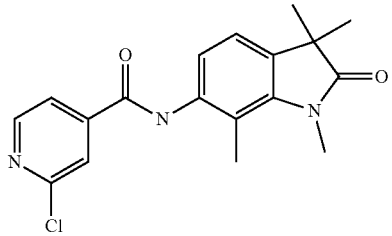 [SMILES: Cc1c(NC(=O)c2ccnc(Cl)c2)ccc2c1N(C)C(=O)C2(C)C]

a) 6-Bromo-7-methyl-1,3-dihydro-indol-2-one

A mixture of 6-bromo-7-methylindoline-2,3-dione (G. W. Rewcastle et al., J. Med. Chem. 1991, 34(1), 217-222; 7.65 g, 31.9 mmol) and hydrazine monohydrate (35.9 g, 35 ml, 718 mmol) was heated to 130° C. for 3 h and then cooled to 10° C. 37% HCl (72.2 g, 60.2 ml, 733 mmol) was added slowly. The precipitate was filtered through sintered glass, washed excessively with water, than with little heptane and dried under high vacuum. The title compound was obtained as yellow crystals and used for the next reaction without further purification.

b) 6-Amino-1,3,3,7-tetramethyl-1,3-dihydro-indol-2-one

Prepared in analogy to example 20 d-f from 6-bromo-7-methyl-1,3-dihydro-indol-2-one. The title compound was obtained as grey foam.

MS ESI (m/z): 205.2 [(M+H)$^+$].

¹H NMR (CDCl₃, 400 MHz): δ (ppm)=6.87-6.84 (m, 1H), 6.43-6.41 (m, 1H), 3.62 (bs, 2H), 3.50 (s, 3H), 2.37 (s, 3H), 1.31 (s, 6H).

c) 2-Chloro-N-(1,3,3,7-tetramethyl-2-oxoindolin-6-yl)isonicotinamide

Prepared in analogy to example 26 from 2-chloroisonicotinic acid and 6-amino-1,3,3,7-tetramethyl-1,3-dihydro-indol-2-one. The title compound was obtained as light yellow crystals.

MS ESI (m/z): 344.1/346.2 [(M+H)⁺].

¹H NMR (CDCl₃, 400 MHz): δ (ppm)=8.60-8.59 (m, 1H), 7.80-7.67 (m, 3H), 7.17-7.08 (m, 2H), 3.54 (s, 3H), 2.50 (s, 3H), 1.36 (s, 6H).

Example 26

2-Chloro-6-methyl-N-(1,3,3-trimethyl-2-oxoindolin-6-yl)nicotinamide

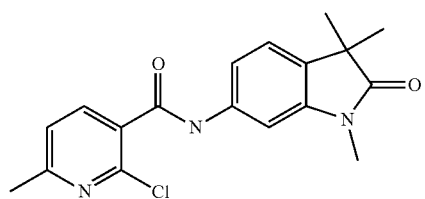 [SMILES: Cc1ccc(C(=O)Nc2ccc3c(c2)N(C)C(=O)C3(C)C)c(Cl)n1]

A suspension of 6-amino-1,3,3-trimethylindolin-2-one (120 mg, 631 μmol), 2-chloro-6-methylnicotinic acid (108 mg, 631 μmol) and 2-(3H-[1,2,3]triazolo[4,5-b]pyridin-3-yl)-1,1,3,3-tetramethylisouronium hexafluorophosphate(V) (480 mg, 1.26 mmol) and N,N-diisopropylethylamine (408 mg, 536 μl, 3.15 mmol) in DMF (3 ml) was stirred at room temperature for 16 hours. An aqueous solution of Na₂CO₃ was added. The aqueous phase was extracted with ethyl acetate, the combined organic phases were dried over sodium sulfate, the solvent was evaporated and the residue purified by silica gel chromatography using ethyl acetate/heptane as eluent. The title compound was obtained as white solid (167 mg).

MS ESI (m/z): 344.2/346.2 [(M+H)⁺].

¹H NMR (CDCl₃, 400 MHz): δ (ppm)=8.33 (bs, 1H), 8.17-8.14 (m, 1H), 7.54 (m, 1H), 7.28-7.25 (m, 1H), 7.20-7.17 (m, 1H), 7.05-7.02 (m, 1H), 3.25 (s, 3H), 2.62 (s, 3H), 1.37 (s, 6H).

Example 27

3-Chloro-N-(1,3,3-trimethyl-2-oxoindolin-6-yl)isonicotinamide

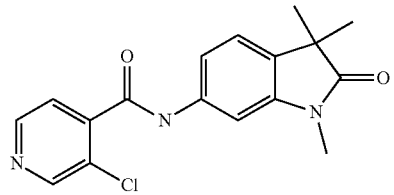 [SMILES: CN1C(=O)C(C)(C)c2ccc(NC(=O)c3ccncc3Cl)cc21]

Prepared in analogy to example 26 from 3-chloroisonicotinic acid. The title compound was obtained as white solid.

MS ESI (m/z): 330.2/332.2 [(M+H)⁺].

¹H NMR (CDCl₃, 400 MHz): δ (ppm)=8.74 (s, 1H), 8.67-8.66 (m, 1H), 8.00 (bs, 1H), 7.70-7.68 (m, 1H), 7.54-7.53 (m, 1H), 7.20-7.18 (m, 1H), 7.04-7.01 (m, 1H), 3.25 (s, 3H), 1.38 (s, 6H).

Example 28

N-(7-fluoro-1,3,3-trimethyl-2-oxoindolin-6-yl)-2-methylisonicotinamide

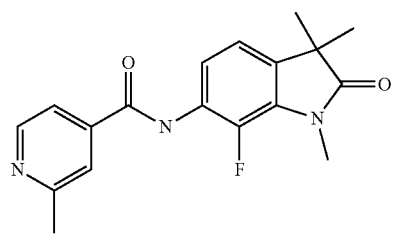 [SMILES: Cc1cc(C(=O)Nc2ccc3c(c2F)N(C)C(=O)C3(C)C)ccn1]

Prepared in analogy to example 26 from 6-amino-7-fluoro-1,3,3-trimethylindolin-2-one (example 13d) and 2-methylisonicotinic acid. The title compound was obtained as light yellow crystals.

MS ESI (m/z): 328.3 [(M+H)⁺].

¹H NMR (CDCl₃, 400 MHz): δ (ppm)=8.72-8.70 (m, 1H), 8.02-7.97 (m, 2H), 7.60 (m, 1H), 7.51-7.50 (m, 1H), 7.04-7.02 (m, 1H), 3.45-3.44 (m, 2.69 (s, 3H), 1.38 (s, 6H).

Example 29

3-Fluoro-N-(1,3,3-trimethyl-2-oxoindolin-6-yl)isonicotinamide

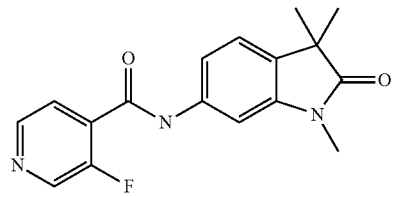

Prepared in analogy to example 26 from 3-fluoroisonicotinic acid. The title compound was obtained as light yellow solid.

MS ESI (m/z): 314.2 [(M+H)⁺].

¹H NMR (CDCl₃, 400 MHz): δ (ppm)=8.68-8.65 (m, 2H), 8.46-8.41 (m, 1H), 8.05-8.01 (m, 1H), 7.54-7.53 (m, 1H), 7.21-7.18 (m, 1H), 7.07-7.04 (m, 1H), 3.25 (s, 3H), 1.38 (s, 6H).

Example 30

3-Chloro-N-(1-cyclopropyl-3,3-dimethyl-2-oxoindolin-6-yl)isonicotinamide

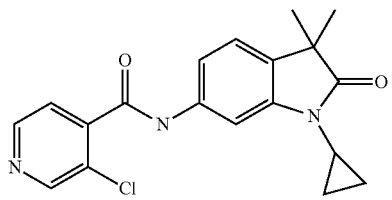 [SMILES: CC1(C)C(=O)N(C2CC2)c2cc(NC(=O)c3ccncc3Cl)ccc21]

Prepared in analogy to example 26 from 3-chloroisonicotinic acid and 6-amino-1-cyclopropyl-3,3-dimethyl-1,3-dihydro-indol-2-one (example 14c). The title compound was obtained as white foam.

MS ESI (m/z): 356.3/358.1 [(M+H)+].

$^1$H NMR (CDCl$_3$, 400 MHz): δ (ppm)=8.75 (m, 1H), 8.68-8.66 (m, 1H), 7.95 (m, 1H), 7.71-7.69 (m, 1H), 7.67 (m, 1H), 7.19-7.16 (m, 1H), 7.12-7.09 (m, 1H), 2.72-2.65 (m, 1H), 1.34 (s, 6H), 1.14-1.07 (m, 2H), 0.96-0.91 (m, 2H).

Example 31

N-(1-Cyclopropyl-3,3-dimethyl-2-oxoindolin-6-yl)-3-fluoroisonicotinamide

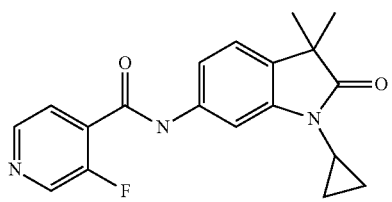 [SMILES: CC1(C)C(=O)N(C2CC2)c2cc(NC(=O)c3ccncc3F)ccc21]

Prepared in analogy to example 26 from 3-fluoroisonicotinic acid and 6-amino-1-cyclopropyl-3,3-dimethyl-1,3-dihydro-indol-2-one (example 14c). The title compound was obtained as light yellow solid.

MS ESI (m/z): 340.2 [(M+H)+].

$^1$H NMR (CDCl$_3$, 400 MHz): δ (ppm)=8.69-8.68 (m, 1H), 8.67-8.65 (m, 1H), 8.44-8.39 (m, 1H), 8.06-8.02 (m, 1H), 7.69-7.68 (m, 1H), 7.19-7.16 (m, 1H), 7.14-7.10 (m, 1H), 2.72-2.65 (m, 1H), 1.34 (s, 6H), 1.15-1.08 (m, 2H), 0.96-0.91 (m, 2H)

Example 32

N-(7-Fluoro-1,3,3-trimethyl-2-oxoindolin-6-yl)-6-methylnicotinamide

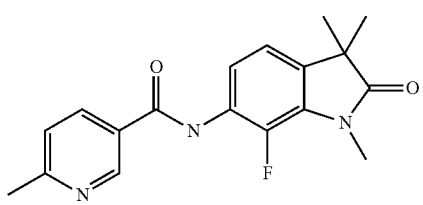 [SMILES: Cc1ccc(C(=O)Nc2ccc3c(c2F)N(C)C(=O)C3(C)C)cn1]

Prepared in analogy to example 1b from 6-amino-7-fluoro-1,3,3-trimethylindolin-2-one (example 13d) and 6-methylnicotinic acid. The title compound was obtained as dark red foam.

MS ESI (m/z): 328.3 [(M+H)+].

$^1$H NMR (CDCl$_3$, 400 MHz): δ (ppm)=9.01-9.00 (m, 1H), 8.13-8.09 (m, 1H), 8.02-7.93 (m, 2H), 7.34-7.31 (m, 1H), 7.03-7.01 (m, 1H), 3.45-3.44 (m, 3H), 2.67 (s, 3H), 1.38 (s, 6H).

Example 33

5-Fluoro-2-methyl-N-(1,3,3-trimethyl-2-oxoindolin-6-yl)isonicotinamide

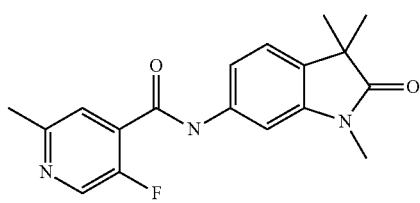 [SMILES: Cc1cc(C(=O)Nc2ccc3c(c2)N(C)C(=O)C3(C)C)c(F)cn1]

Prepared in analogy to example 26 from 5-fluoro-2-methyl-isonicotinic acid (prepared according to U. Abel et al., WO200645514). The title compound was obtained as white solid.

MS ESI (m/z): 326.3 [(M−H)−].

$^1$H NMR (CDCl$_3$, 400 MHz): δ (ppm)=8.54-8.53 (m, 1H), 8.45-8.41 (m, 1H), 7.86-7.84 (m, 1H), 7.53-7.52 (m, 1H), 7.20-7.18 (m, 1H), 7.07-7.04 (m, 1H), 3.25 (s, 3H), 2.64 (s, 3H), 1.38 (s, 6H).

Example 34

N-(5-Chloro-1,3,3-trimethyl-2-oxoindolin-6-yl)isonicotinamide

Prepared in analogy to example 2 from 6-amino-5-chloro-1,3,3-trimethyl-1,3-dihydro-indol-2-one (which is prepared in analogy to example 20 a-f starting from 1-bromo-2-chloro-4-fluoro-5-nitrobenzene). The title compound was obtained as light yellow crystals.

MS ESI (m/z): 330.2/332.1 [(M+H)+].

$^1$H NMR (CDCl$_3$, 400 MHz): δ (ppm)=8.88-8.86 (m, 2H), 8.52 (bs, 1H), 8.17 (m, 1H), 7.77-7.75 (m, 2H), 7.25 (m, 1H), 3.26 (s, 3H), 1.38 (s, 6H).

Example 35

N-(5-Chloro-1,3,3-trimethyl-2-oxoindolin-6-yl)-2-methylisonicotinamide

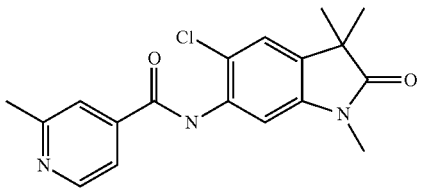 [SMILES: Cc1cc(C(=O)Nc2cc3c(cc2Cl)C(C)(C)C(=O)N3C)ccn1]

Prepared in analogy to example 26 from 2-methylisonicotinic acid and 6-amino-5-chloro-1,3,3-trimethyl-1,3-dihydro-indol-2-one (which is prepared in analogy to example 20 a-f starting from 1-bromo-2-chloro-4-fluoro-5-nitrobenzene). The title compound was obtained as white foam.

MS ESI (m/z): 344.1/346.2 [(M+H)$^+$].

$^1$H NMR (CDCl$_3$, 400 MHz): δ (ppm)=8.74-8.72 (m, 1H), 8.49 (bs, 1H), 8.16 (m, 1H), 7.62 (m, 1H), 7.54-7.52 (m, 1H), 7.24 (m, 1H), 3.26 (s, 3H), 2.70 (s, 3H), 1.38 (s, 6H).

Example 36

N-(1-cyclopropyl-5-fluoro-3,3-dimethyl-2-oxoindolin-6-yl)isonicotinamide

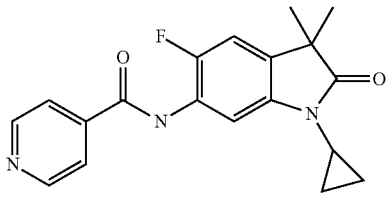 [SMILES: CC1(C)C(=O)N(C2CC2)c2cc(NC(=O)c3ccncc3)c(F)cc21]

a) 6-Bromo-5-fluoro-3,3-dimethylindolin-2-one

To a solution of potassium tert-butoxide (9.27 g, 82.6 mmol) in dry THF (50 ml) under icebath cooling was added 6-bromo-5-fluoroindolin-2-one (example 20c, 3.8 g, 16.5 mmol) in portions, followed by copper (I) bromide-dimethyl sulfide complex (340 mg, 1.65 mmol). After cooling to 2° C. methyl iodide (4.92 g, 2.17 ml, 34.7 mmol) was added slowly over a period of 30 minutes. The reaction mixture was warmed to room temperature, stirred for 16 hours, then cooled to 0° C. and carefully quenched with saturated ammonium chloride solution.

The mixture was diluted with tert-butyl methyl ether and water. The aqueous phase was extracted with tert-butyl methyl ether, the combined organic phases were dried over sodium sulfate, the solvent was evaporated and the residue purified by silica gel chromatography using ethyl acetate/heptane as eluent and followed by trituration with diethyl ether. The title compound was obtained as yellow solid (3.6 g).

MS ESI (m/z): 258.0/260.0 [(M+H)$^+$].

$^1$H NMR (CDCl$_3$, 400 MHz): δ (ppm)=10.44 (bs, 1H), 7.48-7.45 (m, 1H), 7.05-7.04 (m, 1H), 1.25 (s, 6H).

b) 6-Bromo-1-cyclopropyl-5-fluoro-3,3-dimethyl-1,3-dihydro-indol-2-one

Prepared in analogy to example 14b from 6-bromo-5-fluoro-3,3-dimethylindolin-2-one.

MS ESI (m/z): 298.1/300.0 [(M+H)$^+$].

$^1$H NMR (CDCl$_3$, 400 MHz): δ (ppm)=7.24-7.22 (m, 1H), 6.98-6.96 (m, 1H), 2.65-2.58 (m, 1H), 1.32 (s, 6H), 1.11-1.04 (m, 2H), 0.92-0.86 (m, 2H).

c) N-(1-cyclopropyl-5-fluoro-3,3-dimethyl-2-oxoindolin-6-yl)isonicotinamide Prepared in analogy to example 20 e-g. The title compound was obtained as light yellow crystals.

MS ESI (m/z): 340.1 [(M+H)$^+$].

$^1$H NMR (CDCl$_3$, 400 MHz): δ (ppm)=8.87-8.85 (m, 2H), 8.28-8.26 (m, 1H), 8.11-8.10 (m, 1H), 7.75-7.73 (m, 2H), 7.03-7.00 (m, 1H), 2.72-2.65 (m, 1H), 1.34 (s, 6H), 1.16-1.09 (m, 2H), 0.96-0.90 (m, 2H).

Example 37

N-(1-Isopropyl-3,3-dimethyl-2-oxoindolin-6-yl)nicotinamide

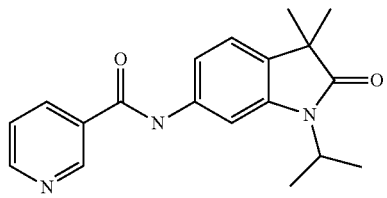 [SMILES: CC(C)N1C(=O)C(C)(C)c2ccc(NC(=O)c3cccnc3)cc21]

a) 6-Bromo-1-isopropyl-3,3-dimethyl-1,3-dihydro-indol-2-one

To a suspension of 6-bromo-3,3-dimethylindolin-2-one (example 14a, 1.68 g, 7.00 mmol) in DMF (30 ml) were added 2-bromopropane (2.15 g, 1.64 ml, 17.5 mmol) and cesium carbonate (5.02 g, 15.4 mmol). The reaction mixture was heated to 80° C. for 18 hours. The reaction mixture was treated with 1 M HCl and the aqueous phase was extracted with EtOAc. The combined organic layers were dried over Na$_2$SO$_4$ and the solvent was evaporated. The residue was purified by silica gel chromatography using ethyl acetate/heptane as eluent. The title compound was obtained as orange solid (2.00 g, 70% purity) and was used for the next reaction without further purification.

b) 6-Benzylamino-1-isopropyl-3,3-dimethyl-1,3-dihydro-indol-2-one

To a solution of 6-bromo-1-isopropyl-3,3-dimethylindolin-2-one (1.99 g, 7.08 mmol, 70%) in THF (20.0 ml) was added BINAP (227 mg, 354 μmol) and sodium tert-butoxide (1.74 g, 17.7 mmol), tris(dibenzylideneacetone)dipalladium (0) chloroform adduct (378 mg, 354 μmol) and benzylamine (766 mg, 782 μl, 7.08 mmol) under an argon atmosphere. The reaction mixture was heated to 70° C. for 18 hours. An aqueous solution of Na₂CO₃ was added to the reaction mixture at room temperature, the aqueous phase was extracted with tert-butyl methyl ether, the combined organic phases were dried over sodium sulfate, the solvent was evaporated and the residue purified by silica gel chromatography using ethyl acetate/heptane as eluent. The title compound was obtained as yellow foam (1.60 g).

MS ESI (m/z): 309.4 [(M+H)⁺].

¹H NMR (CDCl₃, 400 MHz): δ (ppm)=7.42-7.28 (m, 5H), 6.98-6.97 (m, 1H), 6.33-6.28 (m, 2H), 4.58 (hep, J=7.06 Hz, 1H), 4.35-4.33 (m, 2H), 4.11 (m, 1H), 1.39 (d, J=7.06 Hz, 6H), 1.29 (s, 6H).

c) 6-Amino-1-isopropyl-3,3-dimethyl-1,3-dihydro-indol-2-one

Palladium on activated carbon (10%, 276 mg, 259 μmol) was added to a solution of 6-(benzylamino)-1-isopropyl-3,3-dimethylindolin-2-one (1.60 g, 5.18 mmol) in ethanol (75 ml). The mixture was stirred at room temperature under an hydrogen atmosphere (balloon) for 16 hours. As reaction was incomplete, the catalyst was filtered off and washed with ethanol. The solvent was evaporated and ethanol (75 ml) was added to the residue. Palladium on activated carbon (276 mg, 259 μmol) was added and hydrogenation (balloon) continued for 6 hours at 50° C. and 12 hours at room temperature. The catalyst was filtered off, washed with ethanol and the solvent was evaporated. The residue was purified by silica gel chromatography using ethyl acetate/heptane as eluent. The title compound was obtained as light yellow solid (892 mg).

MS ESI (m/z): 219.2 [(M+H)⁺].

¹H NMR (CDCl₃, 400 MHz): δ (ppm)=6.98-6.95 (m, 1H), 6.40-6.39 (m, 1H), 6.36-6.33 (m, 1H), 4.59 (hep, J=7.06 Hz, 1H), 3.69 (bs, 2H), 1.46 (d, J=7.06 Hz, 6H), 1.30 (s, 6H).

d) N-(1-Isopropyl-3,3-dimethyl-2-oxoindolin-6-yl) nicotinamide

Prepared in analogy to example 26 from 6-amino-1-isopropyl-3,3-dimethyl-1,3-dihydro-indol-2-one and nicotinic acid. The title compound was obtained as white foam.

MS ESI (m/z): 324.3 [(M+H)⁺].

¹H NMR (CDCl₃, 400 MHz): δ (ppm)=9.11 (m, 1H), 8.82-8.79 (m, 1H), 8.25-8.21 (m, 1H), 7.87 (bs, 1H), 7.76 (m, 1H), 7.50-7.45 (m, 1H), 7.20-7.17 (m, 1H), 7.02-6.98 (m, 1H), 4.66 (hep, J=7.06 Hz, 1H), 1.52 (d, J=7.06 Hz, 6H), 1.35 (s, 6H).

Example 38

N-(1-Cyclopropyl-5-fluoro-3,3-dimethyl-2-oxoindolin-6-yl)nicotinamide

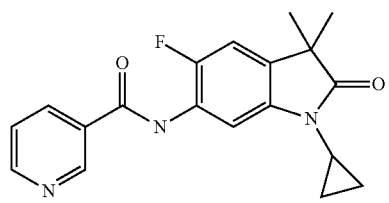 [SMILES: CC1(C)C(=O)N(C2CC2)c2cc(NC(=O)c3cccnc3)c(F)cc21]

Prepared in analogy to example 20e, 20f and 26 from 6-bromo-1-cyclopropyl-5-fluoro-3,3-dimethyl-1,3-dihydro-indol-2-one (example 36b) and nicotinic acid. The title compound was obtained as light yellow foam.

MS ESI (m/z): 340.1 [(M+H)⁺].

¹H NMR (CDCl₃, 400 MHz): δ (ppm)=9.15-9.14 (m, 1H), 8.84-8.82 (m, 1H), 8.28-8.21 (m, 2H), 8.06-8.05 (m, 1H), 7.51-7.47 (m, 1H), 7.03-7.00 (m, 1H), 2.73-2.65 (m, 1H), 1.34 (s, 6H), 1.16-1.09 (m, 2H), 0.96-0.91 (m, 2H).

Example 39

N-(1-Ethyl-3,3-dimethyl-2-oxoindolin-6-yl)-2-methylisonicotinamide

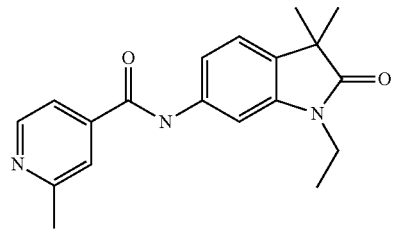 [SMILES: CCN1C(=O)C(C)(C)c2ccc(NC(=O)c3ccnc(C)c3)cc21]

Prepared in analogy to example 1b from 6-amino-1-ethyl-3,3-dimethylindolin-2-one (G. Georges et al., US2006/142247 A1). The title compound was obtained as off-white foam.

MS ESI (m/z): 324.4 [(M+H)⁺].

¹H NMR (CDCl₃, 400 MHz): δ (ppm)=8.70-8.69 (m, 1H), 7.87 (bs, 1H), 7.59-7.56 (m, 2H), 7.51-7.49 (m, 1H), 7.20-7.17 (m, 1H), 7.04-7.00 (m, 1H), 3.79 (q, J=7.27 Hz, 2H), 2.68 (s, 3H), 1.37 (s, 6H), 1.29 (t, J=7.27 Hz, 3H).

Example 40

3-Chloro-N-(1-ethyl-3,3-dimethyl-2-oxoindolin-6-yl)isonicotinamide

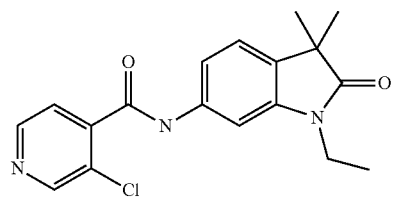 [SMILES: CCN1C(=O)C(C)(C)c2ccc(NC(=O)c3ccncc3Cl)cc21]

Prepared in analogy to example 26 from 3-chloroisonicotinic acid and 6-amino-1-ethyl-3,3-dimethylindolin-2-one (G. Georges et al., US2006/142247 A1). The title compound was obtained as white solid.

MS ESI (m/z): 344.2/346.3 [(M+H)⁺].

¹H NMR (CDCl₃, 400 MHz): δ (ppm)=8.75 (m, 1H), 8.68-8.66 (m, 1H), 7.97 (bs, 1H), 7.70-7.69 (m, 1H), 7.55 (m, 1H), 7.21-7.18 (m, 1H), 7.03-6.99 (m, 1H), 3.80 (q, J=7.27 Hz, 2H), 1.37 (s, 6H), 1.30 (t, J=7.27 Hz, 3H).

Example 41

N-(1-ethyl-3,3-dimethyl-2-oxoindolin-6-yl)-3-fluoroisonicotinamide

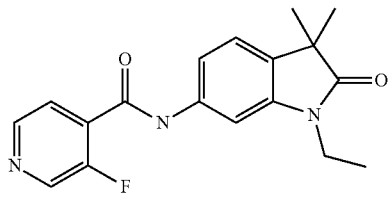

Prepared in analogy to example 26 from 3-fluoroisonicotinic acid and 6-amino-1-ethyl-3,3-dimethylindolin-2-one (G. Georges et al., US2006/142247 A1). The title compound was obtained as light yellow solid.

MS ESI (m/z): 328.3 [(M+H)$^+$].
$^1$H NMR (CDCl$_3$, 400 MHz): δ (ppm)=8.68 (m, 1H), 8.67-8.65 (m, 1H), 8.44-8.40 (m, 1H), 8.05-8.01 (m, 1H), 7.56 (m, 1H), 7.21-7.18 (m, 1H), 7.06-7.02 (m, 1H), 3.80 (q, J=7.27 Hz, 2H), 1.37 (s, 6H), 1.30 (t, J=7.27 Hz, 3H).

Example 42

N-(1-Isopropyl-3,3-dimethyl-2-oxo-2,3-dihydro-1H-indol-6-yl)-2-methyl-isonicotinamide

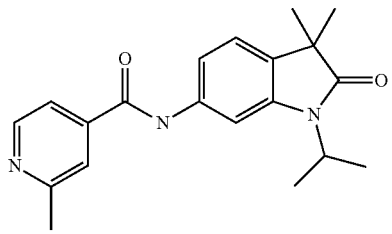 [SMILES: Cc1cc(C(=O)Nc2ccc3c(c2)N(C(C)C)C(=O)C3(C)C)ccn1]

Prepared in analogy to example 37d from 2-methylisonicotinic acid. The title compound was obtained as white solid.

MS ESI (m/z): 338.2 [(M+H)$^+$].
$^1$H NMR (CDCl$_3$, 400 MHz): δ (ppm)=8.70-8.68 (m, 1H), 7.91 (m, 1H), 7.77-7.76 (m, 1H), 7.60 (m, 1H), 7.51-7.49 (m, 1H), 7.19-7.17 (m, 1H), 7.01-6.98 (m, 1H), 4.66 (hep, J=7.06 Hz, 1H), 2.67 (s, 3H), 1.51 (d, J=6.86 Hz, 6H), 1.35 (s, 6H).

Example 43

4-Fluoro-N-(1,3,3-trimethyl-2-oxoindolin-6-yl)benzamide

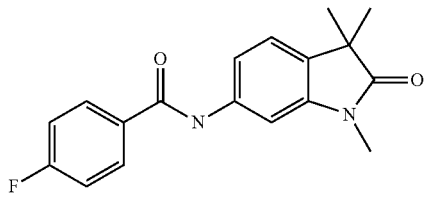 [SMILES: CN1C(=O)C(C)(C)c2ccc(NC(=O)c3ccc(F)cc3)cc21]

Prepared in analogy to example 26 from 4-fluorobenzoic acid. The title compound was obtained as white solid.

MS ESI (m/z): 313.5 [(M+H)$^+$].
$^1$H NMR (CDCl$_3$, 400 MHz): δ (ppm)=7.93-7.88 (m, 2H), 7.82 (bs, 1H), 7.56-7.55 (m, 1H), 7.22-7.15 (m, 3H), 7.01-6.98 (m, 1H), 3.24 (s, 3H), 1.37 (s, 6H).

Example 44

3-Chloro-N-(1,3,3-trimethyl-2-oxoindolin-6-yl)picolinamide

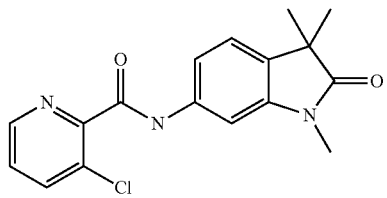 [SMILES: CN1C(=O)C(C)(C)c2ccc(NC(=O)c3ncccc3Cl)cc21]

Prepared in analogy to example 26 from 3-chloropyridine-2-carboxylic acid. The title compound was obtained as white solid.

MS ESI (m/z): 330.5/332.4 [(M+H)$^+$].
$^1$H NMR (CDCl$_3$, 400 MHz): δ (ppm)=8.55-8.53 (m, 1H), 8.24-8.20 (m, 2H), 7.54 (m, 1H), 7.43-7.41 (m, 1H), 7.20-7.18 (m, 1H), 7.06-7.02 (m, 1H), 3.25 (s, 3H), 1.38 (s, 6H).

Example 45

N-(1-Cyclopentyl-3,3-dimethyl-2-oxoindolin-6-yl)-3-fluoroisonicotinamide

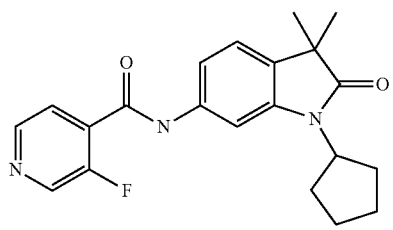 [SMILES: CC1(C)C(=O)N(C2CCCC2)c2cc(NC(=O)c3ccncc3F)ccc21]

a) 6-Amino-1-cyclopentyl-3,3-dimethyl-1,3-dihydro-indol-2-one

Prepared in analogy to example 37 a-c from bromocyclopentane. The title compound was obtained as yellow waxy solid.

MS ESI (m/z): 245.5 [(M+H)$^+$].
$^1$H NMR (CDCl$_3$, 400 MHz): δ (ppm)=6.98-6.95 (m, 1H), 6.37-6.33 (m, 1H), 6.31 (m, 1H), 4.80-4.68 (m, 1H), 3.69 (bs, 2H), 2.10-1.69 (m, 8H), 1.30 (s, 6H).

b) N-(1-Cyclopentyl-3,3-dimethyl-2-oxoindolin-6-yl)-3-fluoroisonicotinamide

Prepared in analogy to example 26 from 3-fluoroisonicotinic acid and 6-amino-1-cyclopentyl-3,3-dimethyl-1,3-dihydro-indol-2-one. The title compound was obtained as yellow foam.

MS ESI (m/z): 368.6 [(M+H)$^+$].
$^1$H NMR (CDCl$_3$, 400 MHz): δ (ppm)=8.68-8.67 (m, 1H), 8.66-8.64 (m, 1H), 8.42-8.36 (m, 1H), 8.05-8.01 (m, 1H), 7.75-7.74 (m, 1H), 7.20-7.18 (m, 1H), 6.98-6.95 (m, 1H), 4.84-4.78 (m, 1H), 2.15-1.71 (m, 8H), 1.36 (s, 6H).

Example 46

N-(1-Cyclopropyl-5-fluoro-3,3-dimethyl-2-oxoindolin-6-yl)-2-methylisonicotinamide

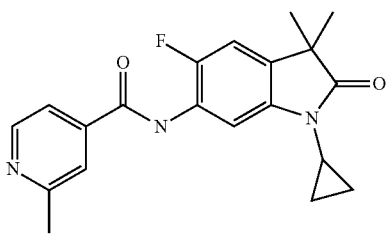 [SMILES: Cc1cc(C(=O)Nc2cc3c(cc2F)C(C)(C)C(=O)N3C2CC2)ccn1]

a) 6-Amino-1-cyclopropyl-5-fluoro-3,3-dimethyl-1,3-dihydro-indol-2-one

To a solution of 6-bromo-1-cyclopropyl-5-fluoro-3,3-dimethylindolin-2-one (example 36b, 400 mg, 1.34 mmol) in NMP (7 ml) were added ammonium hydroxide (6.3 g, 7 ml, 44.9 mmol) and copper(I) oxide (38.4 mg, 268 μmol). The reaction mixture was heated in a sealed tube to 110° C. for 24 hours and then poured into dichloromethane (20 ml). The organic phase was washed with 1 M aqueous sodium bicarbonate solution and with water, dried over sodium sulfate and concentrated in vacuo. The NMP was removed by kugelrohr distillation. The residue was purified by silica gel chromatography using ethyl acetate/heptane as eluent. The title compound was obtained as off-white crystals (257 mg).

MS ESI (m/z): 235.5 [(M+H)$^+$].

$^1$H NMR (CDCl$_3$, 400 MHz): δ (ppm)=6.84-6.81 (m, 1H), 6.57-6.54 (m, 1H), 3.75 (bs, 2H), 2.62-2.54 (m, 1H), 1.28 (s, 6H), 1.06-0.99 (m, 2H), 0.90-0.85 (m, 2H).

b) N-(1-Cyclopropyl-5-fluoro-3,3-dimethyl-2-oxoindolin-6-yl)-2-methylisonicotinamide Prepared in analogy to example 26 from 6-amino-1-cyclopropyl-5-fluoro-3,3-dimethyl-1,3-dihydro-indol-2-one and 2-methylisonicotinic acid. The title compound was obtained as light yellow crystals.

MS ESI (m/z): 354.5 [(M+H)$^+$].

$^1$H NMR (CDCl$_3$, 400 MHz): δ (ppm)=8.72-8.71 (m, 1H), 8.28-8.26 (m, 1H), 8.09 (m, 1H), 7.61 (m, 1H), 7.53-7.51 (m, 1H), 7.03-6.99 (m, 1H), 2.72-2.65 (m, 1H), 2.69 (s, 3H), 1.33 (s, 6H), 1.16-1.09 (m, 2H), 0.96-0.90 (m, 2H).

Example 47

N-(5,7-Difluoro-1,3,3-trimethyl-2-oxo-2,3-dihydro-1H-indol-6-yl)-isonicotinamide

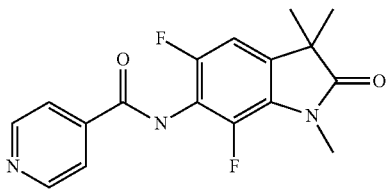

a) 5,7-Difluoro-6-iodo-1,3,3-trimethyl-1,3-dihydro-indol-2-one

Prepared in analogy to example 13a-c from 5,7-difluoro-1,3-dihydro-indol-2-one. The title compound was obtained as off white solid.

MS ESI (m/z): 338 [(M+H)$^+$].

b) 6-Amino-5,7-difluoro-1,3,3-trimethyl-1,3-dihydro-indol-2-one

Prepared in analogy to example 46a from 5,7-difluoro-6-iodo-1,3,3-trimethyl-1,3-dihydro-indol-2-one. The title compound was obtained as yellow solid.

MS ESI (m/z): 227 [(M+H)$^+$].

c) N-(5,7-Difluoro-1,3,3-trimethyl-2-oxo-2,3-dihydro-1H-indol-6-yl)-isonicotinamide To a solution of isonicotinic acid (70 mg, 0.569 mmol) in DMF (2 ml) were added triethylamine (0.24 ml, 1.7 mmol) and Mukaiyama reagent (312 mg, 1.13 mmol) followed by the addition of 6-amino-5,7-difluoro-1,3,3-trimethyl-1,3-dihydro-indol-2-one (154 mg, 0.682 mmol). The resultant reaction mixture was stirred at 25° C. for 12 hours. The mixture was diluted with saturated aqueous NaHCO$_3$ solution (10 ml), and extracted with dichloromethane (2×20 ml). The combined organic layers were washed with brine (15 ml), dried over anhydrous Na$_2$SO$_4$ and the solvent was evaporated. The crude material was purified by column chromatography with amine functionalized silica gel using ethyl acetate/heptane as eluent, followed by purification by prep-HPLC. The title compound was obtained as off-white solid (45 mg).

MS ESI (m/z): 332 [(M+H)$^+$].

Example 48

3-Fluoro-N-(5-fluoro-1,3,3-trimethyl-2-oxoindolin-6-yl)isonicotinamide

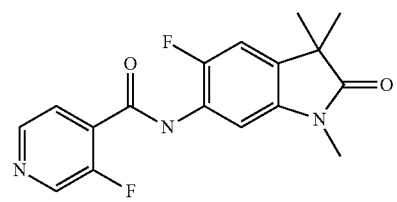

Prepared in analogy to example 26 from 6-amino-5-fluoro-1,3,3-trimethylindolin-2-one (example 20 f) and 3-fluoroisonicotinic acid. The title compound was obtained as light yellow crystals.

MS ESI (m/z): 332.5 [(M+H)$^+$].

¹H NMR (CDCl₃, 400 MHz): δ (ppm)=8.81-8.76 (m, 1H), 8.71-8.66 (m, 2H), 8.08-8.01 (m, 2H), 7.07-7.04 (m, 1H), 3.26 (s, 3H), 1.37 (s, 6H).

Example 49

N-(5,7-Difluoro-1,3,3-trimethyl-2-oxo-2,3-dihydro-1H-indol-6-yl)-2-methyl-isonicotinamide

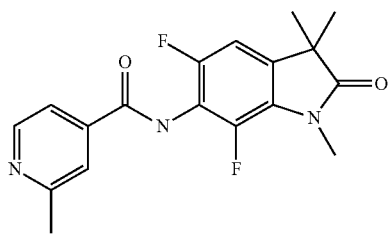 [SMILES: Cc1cc(C(=O)Nc2c(F)cc3c(c2F)N(C)C(=O)C3(C)C)ccn1]

Prepared in analogy to example 47 using 2-methyl isonicotinic acid. The title compound was obtained as off-white solid.

MS ESI (m/z): 346 [(M+H)⁺].

Example 50

N-(5,7-Difluoro-1,3,3-trimethyl-2-oxo-2,3-dihydro-1H-indol-6-yl)-nicotinamide

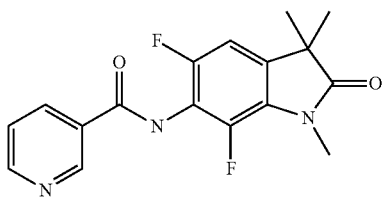 [SMILES: CN1C(=O)C(C)(C)c2cc(F)c(NC(=O)c3cccnc3)c(F)c21]

Prepared in analogy to example 47 using nicotinic acid. The title compound was obtained as off-white solid.

MS ESI (m/z): 332 [(M+H)⁺].

Example 51

3-Chloro-N-(5-fluoro-1,3,3-trimethyl-2-oxoindolin-6-yl)isonicotinamide

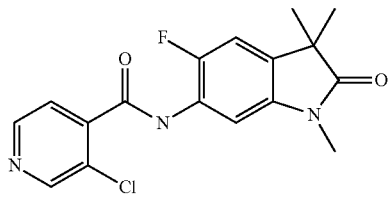

Prepared in analogy to example 26 from 6-amino-5-fluoro-1,3,3-trimethylindolin-2-one (example 20 f) and 3-chloroisonicotinic acid. The title compound was obtained as white crystals.

MS ESI (m/z): 348.4/350.4 [(M+H)⁺].

¹H NMR (CDCl₃, 400 MHz): δ (ppm)=8.77 (m, 1H), 8.70-8.68 (m, 1H), 8.37 (m, 1H), 8.06-8.04 (m, 1H), 7.74-7.73 (m, 1H), 7.06-7.03 (m, 1H), 3.26 (s, 3H), 1.37 (s, 6H).

Example 52

N-(1-(Cyclopropylmethyl)-3,3-dimethyl-2-oxoindolin-6-yl)isonicotinamide

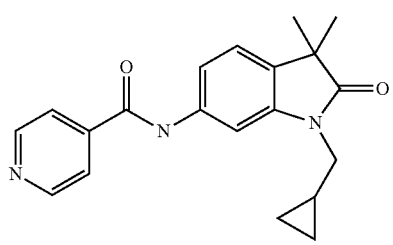 [SMILES: CC1(C)C(=O)N(CC2CC2)c2cc(NC(=O)c3ccncc3)ccc21]

Prepared in analogy to example 37a, 46a and 26 using (bromomethyl)cyclopropane and isonicotinic acid. The title compound was obtained as white solid.

MS ESI (m/z): 336.2 [(M+H)⁺].

¹H NMR (CDCl₃, 400 MHz): δ (ppm)=8.82-8.81 (m, 2H), 8.05 (m, 1H), 7.73-7.72 (m, 2H), 7.67 (m, 1H), 7.19-7.18 (m, 1H), 7.03-7.01 (m, 1H), 3.62 (d, J=6.95 Hz, 2H), 1.37 (s, 6H), 1.23-1.19 (m, 1H), 0.54-0.51 (m, 2H), 0.42-0.39 (m, 2H).

Example 53

N-(1-(Cyclopropylmethyl)-3,3-dimethyl-2-oxoindolin-6-yl)-3-fluoroisonicotinamide

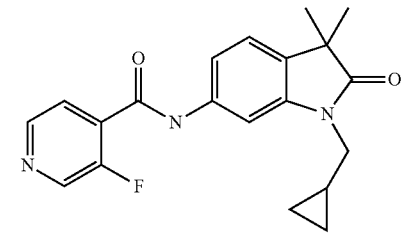 [SMILES: CC1(C)C(=O)N(CC2CC2)c2cc(NC(=O)c3ccncc3F)ccc21]

Prepared in analogy to example 37a, 46a and 26 using (bromomethyl)cyclopropane and 3-fluoroisonicotinic acid. The title compound was obtained as light yellow solid.

MS ESI (m/z): 354.5 [(M+H)⁺].

¹H NMR (CDCl₃, 400 MHz): δ (ppm)=8.69-8.65 (m, 2H), 8.44-8.40 (m, 1H), 8.06-8.02 (m, 1H), 7.67-7.66 (m, 1H), 7.21-7.19 (m, 1H), 7.04-7.00 (m, 1H), 3.64 (d, J=6.86 Hz, 2H), 1.38 (s, 6H), 1.26-1.19 (m, 1H), 0.57-0.51 (m, 2H), 0.45-0.39 (m, 2H).

Example 54

N-(1-Cyclopropyl-3,3-dimethyl-2-oxoindolin-6-yl)-5-fluoro-2-methylisonicotinamide

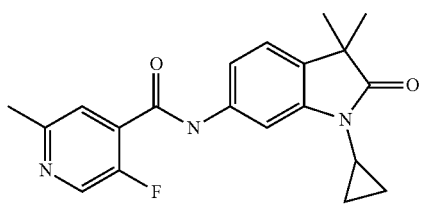 [SMILES: Cc1cc(C(=O)Nc2ccc3c(c2)N(C2CC2)C(=O)C3(C)C)c(F)cn1]

Prepared in analogy to example 26 from 6-amino-1-cyclopropyl-3,3-dimethyl-1,3-dihydro-indol-2-one (example 14c) and 5-fluoro-2-methyl-isonicotinic acid (prepared according to U. Abel et al., WO200645514). The title compound was obtained as light yellow solid.

MS ESI (m/z): 354.4 [(M+H)$^+$].

$^1$H NMR (CD$_3$OD, 400 MHz): δ (ppm)=8.50 (m, 1H), 7.76 (m, 1H), 7.60-7.58 (m, 1H), 7.35-7.32 (m, 1H), 7.29-7.26 (m, 1H), 2.77-2.70 (m, 1H), 2.61 (s, 3H), 1.33 (s, 6H), 1.14-1.08 (m, 2H), 0.92-0.86 (m, 2H).

Example 55

N-(1'-Cyclopropyl-2'-oxospiro[cyclopropane-1,3'-indoline]-6'-yl)isonicotinamide

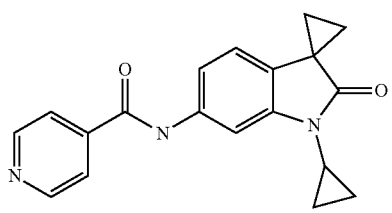 [SMILES: O=C(Nc1ccc2c(c1)N(C1CC1)C(=O)C21CC1)c1ccncc1]

a) 6'-Bromospiro[cyclopropane-1,3'-indolin]-2'-one

A solution of 6-bromoindolin-2-one (2 g, 9.43 mmol) and diisopropylamine (2.00 g, 2.82 ml, 19.8 mmol) in tetrahydrofuran (16 ml) was cooled to –25° C. and a solution of nBuLi (1.6 M in hexane, 23.6 ml, 37.7 mmol) was added dropwise. The reaction mixture was warmed to 0° C. and a solution of 1,2-dibromoethane (5.32 g, 2.44 ml, 28.3 mmol) in tetrahydrofuran (2 ml) was added dropwise. The reaction mixture was warmed to room temperature, stirred for 20 hours and carefully quenched with brine (2 ml) and conc. HCl (2 ml, ice bath). The reaction mixture was diluted with tert-butyl methyl ether and water. The aqueous phase was extracted with tert-butyl methyl ether, the combined organic phases were washed with brine and dried over sodium sulfate. The solvent was evaporated and the residue purified by silica gel chromatography using ethyl acetate/heptane as eluent. The title compound was obtained as red crystals (1.11 g).

MS ESI (m/z): 238.3/240.3 [(M+H)$^+$].

$^1$H NMR (DMSO-D$_6$, 400 MHz): δ (ppm)=10.67 (bs, 1H), 7.12-7.09 (m, 1H), 7.03 (m, 1H), 6.95-6.92 (m, 1H), 1.61-1.57 (m, 2H), 1.49-1.45 (m, 2H).

b) 6'-Amino-1'-cyclopropylspiro[cyclopropane-1,3'-indolin]-2'-one

Prepared in analogy to example 14b and 46a from 6'-bromospiro[cyclopropane-1,3'-indolin]-2'-one. The title compound was obtained as light brown crystals.

MS ESI (m/z): 215.5 [(M+H)$^+$].

$^1$H NMR (CDCl$_3$, 400 MHz): δ (ppm)=6.60-6.57 (m, 2H), 6.35-6.32 (m, 1H), 3.72 (bs, 2H), 2.69-2.61 (m, 1H), 1.61-1.58 (m, 2H), 1.37-1.33 (m, 2H), 1.07-0.98 (m, 2H), 0.96-0.91 (m, 2H).

c) N-(1'-Cyclopropyl-2'-oxospiro[cyclopropane-1,3'-indoline]-6'-yl)isonicotinamide Prepared in analogy to example 26 from 6'-amino-1'-cyclopropylspiro[cyclopropane-1,3'-indolin]-2'-one and isonicotinic acid. The title compound was obtained as light yellow crystals.

MS ESI (m/z): 320.4 [(M+H)$^+$].

$^1$H NMR (DMSO-D$_6$, 400 MHz): δ (ppm)=10.54 (s, 1H), 8.80-8.78 (m, 2H), 7.89-7.87 (m, 2H), 7.77-7.76 (m, 1H), 7.44-7.41 (m, 1H), 7.00-6.97 (m, 1H), 2.78-2.71 (m, 1H), 1.56-1.53 (m, 2H), 1.48-1.44 (m, 2H), 1.05-0.99 (m, 2H), 0.86-0.80 (m, 2H).

Example 56

3-Chloro-N-(1'-cyclopropyl-2'-oxospiro[cyclopropane-1,3'-indoline]-6'-yl)isonicotinamide

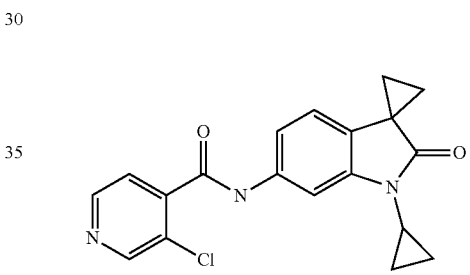

Prepared in analogy to example 55 using 3-chloroisonicotinic acid. The title compound was obtained as light brown crystals.

MS ESI (m/z): 354.4/356.4 [(M+H)$^+$].

$^1$H NMR (DMSO-D$_6$, 400 MHz): δ (ppm)=10.74 (s, 1H), 8.80 (m, 1H), 8.68-8.66 (m, 1H), 7.70-7.66 (m, 2H), 7.32-7.29 (m 1H), 6.99-6.96 (m, 1H), 2.78-2.71 (m, 1H), 1.56-1.52 (m, 2H), 1.48-1.44 (m, 2H), 1.04-0.97 (m, 2H), 0.85-0.79 (m, 2H).

Example 57

N-(1'-Cyclopropyl-2'-oxospiro[cyclopropane-1,3'-indoline]-6'-yl)-3-fluoroisonicotinamide

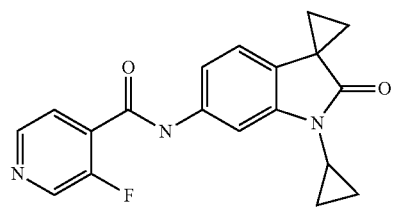 [SMILES: O=C(Nc1ccc2c(c1)N(C1CC1)C(=O)C21CC1)c1ccncc1F]

Prepared in analogy to example 55 using 3-fluoroisonicotinic acid. The title compound was obtained as light yellow crystals.

MS ESI (m/z): 338.4 [(M+H)+].

1H NMR (DMSO-D6, 400 MHz): δ (ppm)=10.73 (s, 1H), 8.77 (m, 1H), 8.61-8.59 (m, 1H), 7.74-7.70 (m, 2H), 7.34-7.31 (m 1H), 6.99-6.97 (m, 1H), 2.77-2.72 (m, 1H), 1.56-1.53 (m, 2H), 1.48-1.44 (m, 2H), 1.04-0.97 (m, 2H), 0.85-0.79 (m, 2H).

Example 58

N-(3,3-Dimethyl-1-(oxetan-3-yl)-2-oxoindolin-6-yl)isonicotinamide

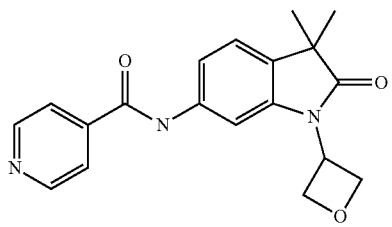 [SMILES: CC1(C)C(=O)N(C2COC2)c2cc(NC(=O)c3ccncc3)ccc21]

Prepared in analogy to example 37a, 46a and 26 using 3-bromooxetane and isonicotinic acid. The title compound was obtained as white foam.

MS ESI (m/z): 338.5 [(M+H)+].

1H NMR (CDCl3, 400 MHz): δ (ppm)=8.85-8.83 (m, 2H), 7.93-7.92 (m, 2H), 7.75-7.73 (m, 2H), 7.45-7.42 (m, 1H), 7.29-7.24 (m, 1H), 5.65-5.56 (m, 1H), 5.17-5.08 (m, 4H), 1.39 (s, 6H).

Example 59

N-(3,3-Dimethyl-1-(oxetan-3-yl)-2-oxoindolin-6-yl)isonicotinamide

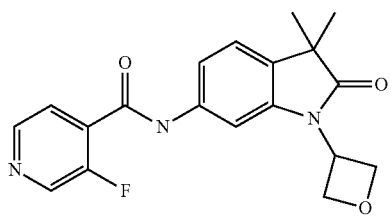 [SMILES: CC1(C)C(=O)N(C2COC2)c2cc(NC(=O)c3ccncc3F)ccc21]

Prepared in analogy to example 37a and 46a and 26 using 3-bromooxetane and 3-fluoroisonicotinic acid. The title compound was obtained as white foam.

MS ESI (m/z): 356.4 [(M+H)+].

1H NMR (CDCl3, 400 MHz): δ (ppm)=8.69-8.68 (m, 1H), 8.66-8.64 (m, 1H), 8.46-8.42 (m, 1H), 8.06-8.03 (m, 2H), 7.29-7.25 (m, 2H), 5.63-5.54 (m, 1H), 5.19-5.07 (m, 4H), 1.39 (s, 6H).

Example 60

N-(1'-Cyclopropyl-2'-oxospiro[cyclopropane-1,3'-indoline]-6'-yl)-2-methylisonicotinamide

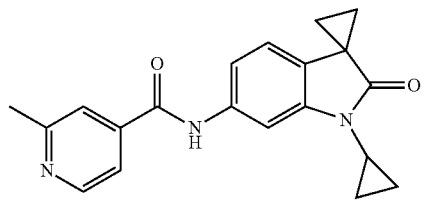 [SMILES: Cc1cc(C(=O)Nc2ccc3c(c2)N(C2CC2)C(=O)C32CC2)ccn1]

Prepared in analogy to example 55 using 2-methylisonicotinic acid. The title compound was obtained as light yellow crystals.

MS ESI (m/z): 334.5 [(M+H)+].

1H NMR (DMSO-D6, 300 MHz) δ=10.49 (s, 1H), 8.64 (d, J=4.8 Hz, 1H), 7.76-7.75 (m, 2H), 7.67 (d, J=5.0 Hz, 1H), 7.43 (dd, J=1.8, 8.1 Hz, 1H), 6.98 (d, J=8.1 Hz, 1H), 2.78-2.72 (m, 1H), 2.58 (s, 3H), 1.56-1.44 (m, 4H), 1.05-0.80 (m, 4H).

Example 61

3-Chloro-N-(7-fluoro-1,3,3-trimethyl-2-oxoindolin-6-yl)isonicotinamide

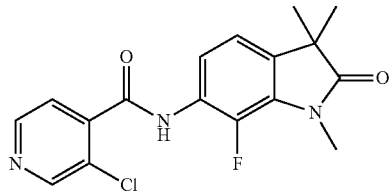 [SMILES: CN1C(=O)C(C)(C)c2ccc(NC(=O)c3ccncc3Cl)c(F)c21]

Prepared in analogy to example 23 using 3-chloroisonicotinic acid. The title compound was obtained as yellow crystals.

MS ESI (m/z): 348.4/350.4 [(M+H)+].

1H NMR (DMSO-D6, 300 MHz) δ=10.58 (s, 1H), 8.79 (s, 1H), 8.67 (d, J=4.8 Hz, 1H), 7.64 (d, J=4.6 Hz, 1H), 7.39-7.34 (m, 1H), 7.22 (d, J=7.9 Hz, 1H), 3.32 (s, 3H), 1.30 (s, 6H).

Example 62

3-Chloro-N-(3,3-dimethyl-1-(oxetan-3-yl)-2-oxoindolin-6-yl)isonicotinamide

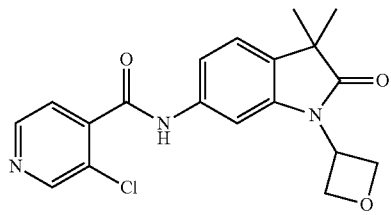 [SMILES: CC1(C)C(=O)N(C2COC2)c2cc(NC(=O)c3ccncc3Cl)ccc21]

Prepared in analogy to example 59 using 3-chloroisonicotinic acid. The title compound was obtained as light yellow solid.

MS ESI (m/z): 372.5/374.5 [(M+H)+].

$^1$H NMR (CDCl$_3$, 300 MHz) δ=8.75 (s, 1H), 8.66 (d, J=4.6 Hz, 1H), 8.02 (s, 1H), 7.92 (d, J=1.8 Hz, 1H), 7.70 (d, J=4.8 Hz, 1H), 7.39 (dd, J=1.9, 8.0 Hz, 1H), 7.29-7.26 (m, 1H), 5.62-5.53 (m, 1H), 5.17-5.06 (m, 4H), 1.39 (s, 6H).

Example 63

N-(3,3-Dimethyl-1-(oxetan-3-yl)-2-oxoindolin-6-yl)-2-methylisonicotinamide

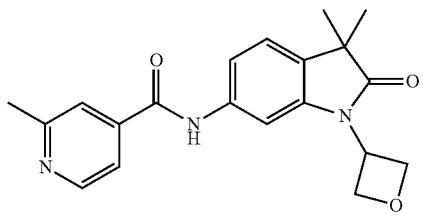 [SMILES: Cc1cc(C(=O)Nc2ccc3c(c2)N(C2COC2)C(=O)C3(C)C)ccn1]

Prepared in analogy to example 59 using 2-methylisonicotinic acid. The title compound was obtained as white foam.

MS ESI (m/z): 352.5 [(M+H)+].

$^1$H NMR (CDCl$_3$, 300 MHz) δ=8.70 (d, J=5.0 Hz, 1H), 7.93 (s, 1H), 7.90 (d, J=1.8 Hz, 1H), 7.62 (s, 1H), 7.53 (d, J=5.2 Hz, 1H), 7.47 (dd, J=1.9, 8.0 Hz, 1H), 7.28-7.26 (m, 1H), 5.60 (tt, J=5.9, 7.9 Hz, 1H), 5.18-5.07 (m, 4H), 2.68 (s, 3H), 1.39 (s, 6H).

Example 64

N-(3,3-Dimethyl-1-(oxetan-3-yl)-2-oxoindolin-6-yl) nicotinamide

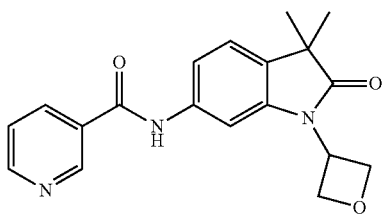 [SMILES: CC1(C)C(=O)N(C2COC2)c2cc(NC(=O)c3cccnc3)ccc21]

Prepared in analogy to example 59 using 2-methylisonicotinic acid. The title compound was obtained as light yellow foam.

MS ESI (m/z): 338.5 [(M+H)+].

$^1$H NMR (CDCl$_3$, 300 MHz) δ=9.15 (d, J=1.8 Hz, 1H), 8.77 (dd, J=1.6, 4.8 Hz, 1H), 8.31 (br s, 1H), 8.26 (td, J=2.0, 7.9 Hz, 1H), 7.93 (d, J=1.6 Hz, 1H), 7.51-7.41 (m, 2H), 7.28-7.26 (m, 1H), 5.65-5.56 (m, 1H), 5.18-5.07 (m, 4H), 1.38 (s, 6H).

Example 65

N-(1-(3-Cyclopropoxypropyl)-3,3-dimethyl-2-oxoindolin-6-yl)-3-fluoroisonicotinamide

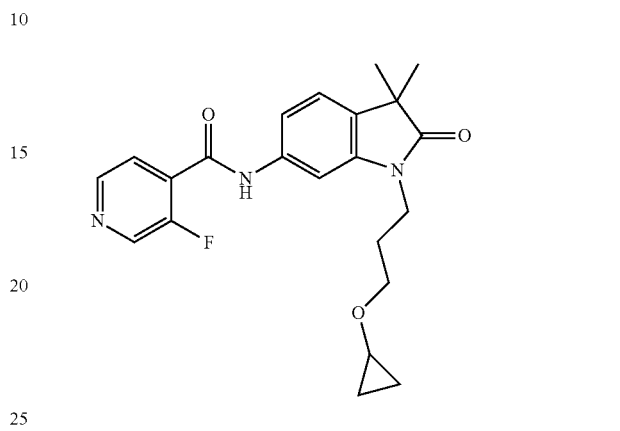

a) (3-Bromopropoxy)cyclopropane

To a solution of 3-cyclopropoxypropan-1-ol (J.-W. Huang et al., Tetrahedron Letters, 1999, 40(49), 8647-8650; 350 mg, 3.01 mmol) and CBr$_4$ (1.2 g, 3.62 mmol) in pentane (4 ml) was added portionwise triphenylphosphine (948 mg, 3.62 mmol). The reaction mixture was stirred at room temperature for 18 hours and then filtered through sintered glass and washed with pentane. The pentane layers were combined and concentrated in vacuo. The title compound was obtained as colorless liquid (586 mg, purity ~90%).

$^1$H NMR (CDCl$_3$, 300 MHz) δ=3.62 (t, J=6.0 Hz, 2H), 3.47 (t, J=6.5 Hz, 2H), 3.31-3.25 (m, 1H), 2.08 (quin, J=6.2 Hz, 2H), 0.59-0.43 (m, 4H).

b) 6-Bromo-1-(3-cyclopropoxypropyl)-3,3-dimethylindolin-2-one

To a suspension of 6-bromo-3,3-dimethylindolin-2-one (example 14a, 300 mg, 1.25 mmol) and Cs$_2$CO$_3$ (814 mg, 2.5 mmol) in DMF (2 ml) was added a solution of (3-bromopropoxy)cyclopropane (447 mg, 2.5 mmol) in DMF (0.5 ml). The reaction mixture was heated to 70° C. for 3 hours. The reaction mixture was filtered through sintered glass and concentrated. The crude material was purified by flash chromatography on silica gel using ethyl acetate as eluent. The title compound was obtained as orange viscous oil (360 mg).

MS ESI (m/z): 338.4/340.4 [(M+H)+].

$^1$H NMR (CDCl$_3$, 300 MHz) δ=7.17 (dd, J=1.8, 7.9 Hz, 1H), 7.06-7.03 (m, 2H), 3.75 (t, J=6.9 Hz, 2H), 3.49 (t, J=6.0 Hz, 2H), 3.24 (tt, J=3.0, 6.1 Hz, 1H), 1.92 (quin, J=6.4 Hz, 2H), 1.35 (s, 6H), 0.59-0.41 (m, 4H).

c) 6-Amino-1-(3-cyclopropoxypropyl)-3,3-dimethylindolin-2-one

To a suspension of 6-bromo-1-(3-cyclopropoxypropyl)-3,3-dimethylindolin-2-one (360 mg, 1.06 mmol) and K$_2$CO$_3$ (441 mg, 3.19 mmol) in DMSO (2 ml) were added L-proline (49.0 mg, 426 μmol), copper (I) iodide (40.5 mg, 213 μmol) and ammonium hydroxide (373 mg, 414 μl, 2.66 mmol). The tube was sealed and heated to 90° C. for 7 hours. The reaction mixture was poured into TBME (50 ml) and extracted with 1 M HCl. The combined aqueous layers were basified with 2M Na₂CO₃. The aqueous phase was extracted two times with TBME. The combined organic layers were dried over Na₂SO₄ and concentrated in vacuo. The title compound was obtained as brown viscous oil (228 mg).

MS ESI (m/z): 275.5 [(M+H)⁺].

¹H NMR (CDCl₃, 300 MHz) δ=6.95 (d, J=7.9 Hz, 1H), 6.34 (dd, J=2.1, 7.8 Hz, 1H), 6.27 (d, J=2.0 Hz, 1H), 3.71 (t, J=6.9 Hz, 2H), 3.50 (t, J=6.2 Hz, 2H), 3.25 (tt, J=3.1, 6.0 Hz, 1H), 1.91 (quin, J=6.6 Hz, 2H), 1.31 (s, 6H), 0.59-0.41 (m, 4H).

d) N-(1-(3-Cyclopropoxypropyl)-3,3-dimethyl-2-oxoindolin-6-yl)-3-fluoroisonicotinamide Prepared in analogy to example 26 from 6-amino-1-(3-cyclopropoxypropyl)-3,3-dimethylindolin-2-one and 3-fluoroisonicotinic acid. The title compound was obtained as yellow oil.

MS ESI (m/z): 398.6 [(M+H)⁺].

¹H NMR (CDCl₃, 300 MHz) δ=8.68 (d, J=2.8 Hz, 1H), 8.65 (dd, J=1.4, 5.0 Hz, 1H), 8.40 (d, J=13.5 Hz, 1H), 8.03 (dd, J=4.9, 6.6 Hz, 1H), 7.45 (d, J=1.4 Hz, 1H), 7.21-7.14 (m, 2H), 3.81 (t, J=6.9 Hz, 2H), 3.52 (t, J=6.1 Hz, 2H), 3.25 (tt, J=3.0, 6.1 Hz, 1H), 1.96 (quin, J=6.5 Hz, 2H), 1.37 (s, 6H), 0.59-0.39 (m, 4H).

Example 66

N-(1-(3-Cyclopropoxypropyl)-3,3-dimethyl-2-oxoindolin-6-yl)isonicotinamide

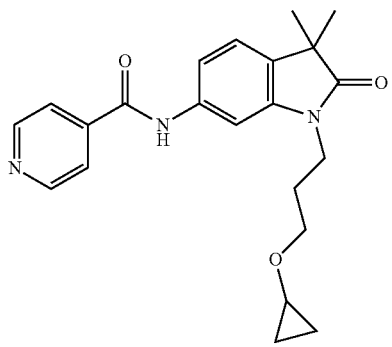 [SMILES: CC1(C)C(=O)N(CCCOC2CC2)c2cc(NC(=O)c3ccncc3)ccc21]

Prepared in analogy to example 65 using isonicotinic acid. The title compound was obtained as light yellow crystals.

MS ESI (m/z): 380.6 [(M+H)⁺].

¹H NMR (CDCl₃, 300 MHz) δ=8.84-8.82 (m, 2H), 7.85 (s, 1H), 7.73-7.71 (m, 2H), 7.44 (d, J=1.6 Hz, 1H), 7.19 (d, J=8.1 Hz, 1H), 7.13 (dd, J=1.8, 8.1 Hz, 1H), 3.80 (t, J=6.9 Hz, 2H), 3.53 (t, J=6.1 Hz, 2H), 3.25 (tt, J=3.1, 6.0 Hz, 1H), 1.96 (quin, J=6.5 Hz, 2H), 1.37 (s, 6H), 0.58-0.39 (m, 4H).

Example 67

3-Fluoro-N-(1-(hydroxymethyl)-3,3-dimethyl-2-oxoindolin-6-yl)isonicotinamide

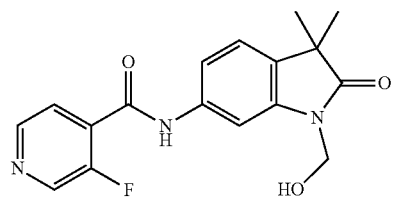 [SMILES: CC1(C)C(=O)N(CO)c2cc(NC(=O)c3ccncc3F)ccc21]

a) 6-Bromo-3,3-dimethyl-1-((2-(trimethylsilyl)ethoxy)methyl)indolin-2-one

A solution of 6-bromo-3,3-dimethylindolin-2-one (example 14a, 4.87 g, 20.3 mmol) in THF (135 ml) was cooled to 0° C. and a solution of sodium bis(trimethylsilyl)amide in THF (1M, 24.3 ml, 24.3 mmol) was added during 15 minutes. Then a solution of (2-(chloromethoxy)ethyl)trimethylsilane (4.27 g, 4.54 ml, 24.3 mmol) in THF (5 ml) was added during 15 minutes. After 4 hours at 0° C. the reaction mixture was poured into ice-water.

The aqueous phase was extracted with ethyl acetate. The combined organic layers were dried over Na₂SO₄ and the solvent was evaporated. The crude product was purified by flash chromatography on silica gel using EtOAc/heptane as eluent. The title compound was obtained as light yellow liquid (7.76 g, ~70% purity).

MS ESI (m/z): 370.0/372.0 [(M+H)⁺].

¹H NMR (CDCl₃, 300 MHz) δ=7.24-7.21 (m, 2H), 7.07 (d, J=8.5 Hz, 1H), 5.13 (s, 2H), 3.57-3.51 (m, 2H), 1.37 (s, 6H), 0.95-0.92 (m, 2H), −0.04 (s, 9H).

b) 3-Fluoro-N-(1-(hydroxymethyl)-3,3-dimethyl-2-oxoindolin-6-yl)isonicotinamide To a solution of N-(3,3-dimethyl-2-oxo-1-((2-(trimethylsilyl)ethoxy)methyl)indolin-6-yl)-3-fluoroisonicotinamide (prepared in analogy to example 37b, 37c and 26 from 6-bromo-3,3-dimethyl-1-((2-(trimethylsilyl)ethoxy)methyl)indolin-2-one and 3-fluoroisonicotinic acid; 110 mg, 256 μmol) in chloroform (2 ml) was added TFA (1.7 g, 1.14 ml, 14.9 mmol). After 5 hours at room temperature the reaction mixture was treated with a saturated aqueous solution of NaHCO₃. The aqueous phase was extracted with EtOAc. The combined organic layers were dried over Na₂SO₄ and concentrated in vacuo. The crude material was purified by flash chromatography on silica gel using ethyl acetate/heptane as eluent.

The title compound was obtained as light yellow solid (42 mg).

MS ESI (m/z): 330.4 [(M+H)⁺].

¹H NMR (DMSO-D₆, 300 MHz) δ=10.71 (s, 1H), 8.76 (d, J=1.4 Hz, 1H), 8.59 (dd, J=1.3, 4.7 Hz, 1H), 7.70-7.67 (m,

1H), 7.56 (s, 1H), 7.33 (m, 2H), 6.23 (t, J=6.9 Hz, 1H), 5.05 (d, J=6.9 Hz, 2H), 1.28 (s, 6H).

Example 68

3-Fluoro-N-(1-(2-hydroxyethyl)-3,3-dimethyl-2-oxoindolin-6-yl)isonicotinamide

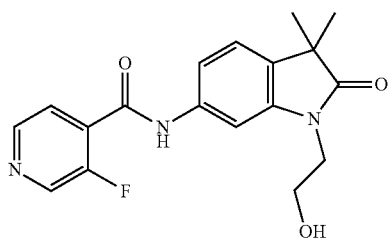

a) 6-Bromo-1-(2-(tert-butyldimethylsilyloxy)ethyl)-3,3-dimethylindolin-2-one

To a solution of 6-bromo-3,3-dimethylindolin-2-one (example 14a, 500 mg, 2.08 mmol) in DMF (16.7 ml) under an argon atmosphere were added (2-bromoethoxy)(tert-butyl)dimethylsilane (996 mg, 894 µl, 4.16 mmol) and cesium carbonate (1.36 g, 4.16 mmol). After 1 hour at 80° C. the reaction mixture was treated with water and the aqueous phase was extracted with EtOAc.

The combined organic layers were dried over $Na_2SO_4$ and concentrated in vacuo. The crude material was purified by flash chromatography on silica gel using heptane/ethyl acetate as eluent. The title compound was obtained as orange liquid (740 mg).

MS ESI (m/z): 398.5/400.5 [(M+H)$^+$].

$^1$H NMR (CDCl$_3$, 300 MHz) δ=7.19 (d, J=1.6 Hz, 1H), 7.15 (dd, J=1.6, 7.9 Hz, 1H), 7.02 (d, J=7.9 Hz, 1H), 3.87-3.78 (m, 4H), 1.35 (s, 6H), 0.81 (s, 9H), −0.04 (s, 6H).

b) 3-Fluoro-N-(1-(2-hydroxyethyl)-3,3-dimethyl-2-oxoindolin-6-yl)isonicotinamide To a solution of N-(1-(2-(tert-butyldimethylsilyloxy) ethyl)-3,3-dimethyl-2-oxoindolin-6-yl)-3-fluoroisonicotinamide (prepared in analogy to example 65c and 26 from 6-bromo-1-(2-(tert-butyldimethylsilyloxy)ethyl)-3,3-dimethylindolin-2-one and 3-fluoroisonicotinic acid; 195 mg, 426 µmol) in THF (10 ml) was added a solution of TBAF in THF (1M, 639 µl, 639 µmol). After 2 hours at room temperature the reaction mixture was treated with water and the aqueous phase was extracted with EtOAc. The combined organic layers were dried over $Na_2SO_4$ and concentrated in vacuo. The crude material was purified by flash chromatography on silica gel using dichloromethane/methanol (with 10% ammonia) as eluent. The title compound was obtained as light yellow solid (151 mg).

MS ESI (m/z): 344.5 [(M+H)$^+$].

$^1$H NMR (DMSO-D$_6$, 300 MHz) δ=10.69 (s, 1H), 8.76 (d, J=1.2 Hz, 1H), 8.60 (dd, J=1.1, 4.7 Hz, 1H), 7.71-7.67 (m, 1H), 7.51 (s, 1H), 7.33-7.29 (m, 2H), 4.90 (t, J=5.4 Hz, 1H), 3.72-3.68 (m, 2H), 3.62-3.57 (m, 2H), 1.27 (s, 6H).

Example 69

3-Fluoro-N-(1-(3-hydroxypropyl)-3,3-dimethyl-2-oxoindolin-6-yl)isonicotinamide

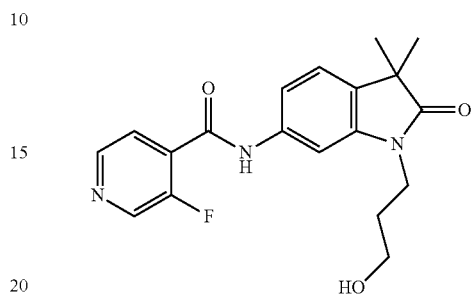

Prepared in analogy to example 68 using (3-bromopropoxy)(tert-butyl)dimethylsilane. The title compound was obtained as light yellow foam.

MS ESI (m/z): 358.5 [(M+H)$^+$].

$^1$H NMR (CDCl$_3$, 300 MHz) δ=8.68 (d, J=2.8 Hz, 1H), 8.66 (dd, J=1.4, 4.8 Hz, 1H), 8.43 (d, J=14.5 Hz, 1H), 8.02 (dd, J=4.9, 6.6 Hz, 1H), 7.63 (d, J=1.8 Hz, 1H), 7.22 (d, J=7.9 Hz, 1H), 7.04 (dd, J=1.8, 7.9 Hz, 1H), 3.95-3.91 (m, 2H), 3.59-3.53 (m, 2H), 3.16-3.11 (m, 1H), 1.91 (td, J=6.0, 11.7 Hz, 2H), 1.40 (s, 6H).

Example 70

N-(1-(3-(Cyclopropylsulfonyl)propyl)-3,3-dimethyl-2-oxoindolin-6-yl)isonicotinamide

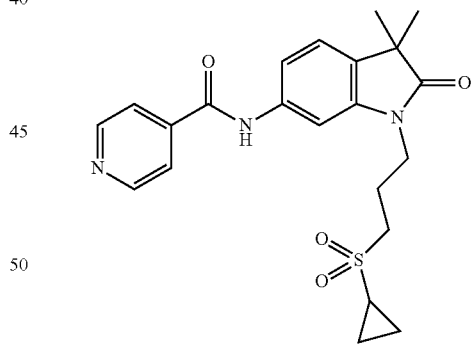

a) 3-(Cyclopropylthio)propan-1-ol

A solution of 3-mercaptopropan-1-ol (1.15 g, 1.08 ml, 12.5 mmol), potassium tert-butoxide (1.4 g, 12.5 mmol) and bromocyclopropane (1.51 g, 1 ml, 12.5 mmol) in DMSO (30 ml) was heated to 80° C. for 15 hours. The reaction mixture was poured into 75 mL saturated aqueous NaHCO$_3$ solution and extracted with diethyl ether and washed with water. The combined organic layers were dried with sodium sulfate, filtered and the obtained solution concentrated in vacuo. The title compound was obtained as red liquid (1.24 g) and was used without further purification.

¹H NMR (CDCl₃, 300 MHz): δ=3.78 (q, J=5.9 Hz, 2H), 2.70 (t, J=7.1 Hz, 2H), 2.00-1.81 (m, 3H), 0.95-0.75 (m, 2H), 0.61-0.47 (m, 2H).

b) (3-Bromopropyl)(cyclopropyl)sulfane

To a suspension of 3-(cyclopropylthio)propan-1-ol (1.68 g, 12.7 mmol) and CBr₄ (5.06 g, 15.2 mmol) in pentane (13 ml) was added triphenylphosphine (4.00 g, 15.2 mmol) portion-wise under icecooling. Dichloromethane (7 ml) was added and the suspension was stirred for 4 hours. The reaction mixture was filtered and washed with pentane. The obtained solution was concentrated in vacuo. The title compound was obtained as a mixture with TPPO as brown semisolid (6.66 g). The material was used without further purification.

c) 6-Amino-1-(3-(cyclopropylthio)propyl)-3,3-dimethylindolin-2-one

Prepared in analogy to example 65b and 65c using (3-bromopropyl)(cyclopropyl)sulfane. The title compound was obtained as brown viscous oil.

MS ESI (m/z): 291.5 [(M+H)⁺].

¹H NMR (CDCl₃, 300 MHz) δ=6.96 (d, J=7.9 Hz, 1H), 6.35 (dd, J=2.0, 7.9 Hz, 1H), 6.28 (d, J=2.0 Hz, 1H), 3.76 (t, J=7.1 Hz, 2H), 3.71 (br s, 2H), 2.63-2.58 (m, 2H), 2.00 (quin, J=7.2 Hz, 2H), 1.89 (tt, J=4.3, 7.4 Hz, 1H), 1.32 (s, 6H), 0.86-0.80 (m, 2H), 0.57-0.51 (m, 2H).

d) N-(1-(3-(Cyclopropylthio)propyl)-3,3-dimethyl-2-oxoindolin-6-yl)isonicotinamide A solution of 6-amino-1-(3-(cyclopropylthio)propyl)-3,3-dimethylindolin-2-one (160 mg, 496 μmol), isonicotinoyl chloride (84.2 mg, 595 μmol) and DIPEA (192 mg, 260 μl, 1.49 mmol) in dichloromethane (3 ml) was stirred at room temperature for 3 hours. The crude material was purified by flash chromatography on silica gel using EtOAc/heptane as eluent. The title compound was obtained as yellow viscous oil (131 mg).

MS ESI (m/z): 396.5 [(M+H)⁺].

¹H NMR (CDCl₃, 300 MHz) δ=8.84-8.82 (m, 2H), 7.89 (s, 1H), 7.73-7.71 (m, 2H), 7.54 (d, J=1.8 Hz, 1H), 7.19 (d, J=7.9 Hz, 1H), 7.08 (dd, J=1.8, 7.9 Hz, 1H), 3.85 (t, J=7.1 Hz, 2H), 2.62 (t, J=7.4 Hz, 2H), 2.06 (quin, J=7.2 Hz, 2H), 1.91 (tt, J=4.4, 7.4 Hz, 1H), 1.37 (s, 6H), 0.86-0.80 (m, 2H), 0.56-0.51 (m, 2H).

e) N-(1-(3-(Cyclopropylsulfonyl)propyl)-3,3-dimethyl-2-oxoindolin-6-yl)isonicotinamide To a solution of N-(1-(3-(cyclopropylthio)propyl)-3,3-dimethyl-2-oxoindolin-6-yl)isonicotinamide (130 mg, 329 μmol) in methanol (1 ml) was added dropwise a solution of oxone (303 mg, 493 μmol) in water (1.00 ml). After 2 hours at room temperature the reaction mixture was poured into water and the aqueous phase was extracted with EtOAc. The combined organic layers were washed with saturated NaHCO₃ solution, dried over Na₂SO₄ and concentrated in vacuo. The crude material was purified by flash chromatography on silica gel using dichloromethane/methanol as eluent. The title compound was obtained as white foam (91 mg).

MS ESI (m/z): 428.6 [(M+H)⁺].

¹H NMR (CDCl₃, 300 MHz) δ=8.84-8.82 (m, 2H), 7.93 (s, 1H), 7.73-7.71 (m, 2H), 7.47 (d, J=1.6 Hz, 1H), 7.22 (d, J=7.9 Hz, 1H), 7.17 (dd, J=1.6, 7.9 Hz, 1H), 3.92 (t, J=7.0 Hz, 2H), 3.14-3.09 (m, 2H), 2.42 (tt, J=4.8, 7.9 Hz, 1H), 2.34-2.25 (m, 2H), 1.38 (s, 6H), 1.28-1.22 (m, 2H), 1.09-1.02 (m, 2H).

Example 71

N-(1-(3-(Cyclopropylsulfonyl)propyl)-3,3-dimethyl-2-oxoindolin-6-yl)isonicotinamide

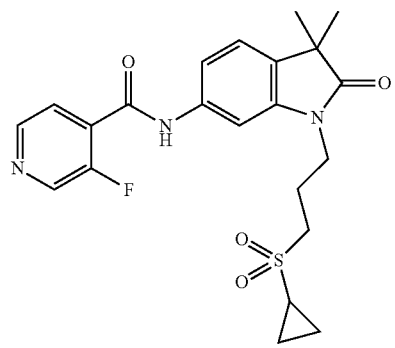 [SMILES: CC1(C)C(=O)N(CCCS(=O)(=O)C2CC2)c2cc(NC(=O)c3ccncc3F)ccc21]

Prepared in analogy to example 70 a-c, 26 and 70e using 3-fluoroisonicotinic acid. The title compound was obtained as white foam.

MS ESI (m/z): 446.5 [(M+H)⁺].

¹H NMR (CDCl₃, 300 MHz) δ=8.68 (d, J=2.6 Hz, 1H), 8.66 (d, J=4.8 Hz, 1H), 8.43 (d, J=13.7 Hz, 1H), 8.01 (dd, J=5.0, 6.5 Hz, 1H), 7.54 (d, J=1.8 Hz, 1H), 7.22 (d, J=8.0 Hz, 1H), 7.13 (dd, J=1.8, 8.0 Hz, 1H), 3.93 (t, J=6.8 Hz, 2H), 3.14-3.09 (m, 2H), 2.42 (tt, J=4.8, 8.0 Hz, 1H), 2.36-2.26 (m, 2H), 1.38 (s, 6H), 1.28-1.22 (m, 2H), 1.09-1.02 (m, 2H).

Example 72

N-(3,3-Dimethyl-2-oxoindolin-6-yl)-3-fluoroisonicotinamide

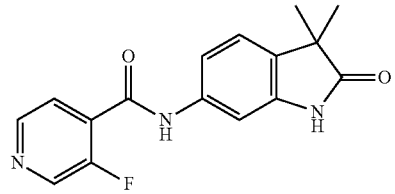 [SMILES: CC1(C)C(=O)Nc2cc(NC(=O)c3ccncc3F)ccc21]

Prepared in analogy to example 1 using 3-fluoroisonicotinic acid. The title compound was obtained as light yellow solid.

MS ESI (m/z): 300.5 [(M+H)⁺].

¹H NMR (DMSO-D₆, 400 MHz) δ=10.65 (s, 1H), 10.38 (s, 1H), 8.76 (d, J=1.1 Hz, 1H), 8.59 (dd, J=1.3, 4.8 Hz, 1H), 7.69-7.67 (m, 1H), 7.44 (d, J=1.9 Hz, 1H), 7.28-7.22 (m, 1H), 7.21-7.12 (m, 1H), 1.24 (s, 6H).

Example 73

3-Chloro-N-(1-(3-hydroxypropyl)-3,3-dimethyl-2-oxoindolin-6-yl)isonicotinamide

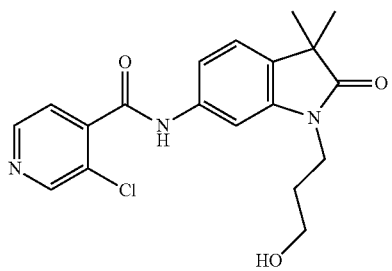

Prepared in analogy to example 69 using 3-chloroisonicotinic acid. The title compound was obtained as white solid.

MS ESI (m/z): 374.5/376.5 [(M+H)+].

¹H NMR (CDCl₃, 300 MHz) δ=8.74 (s, 1H), 8.66 (d, J=5.0 Hz, 1H), 8.11 (s, 1H), 7.67 (d, J=4.8 Hz, 1H), 7.61 (d, J=1.8 Hz, 1H), 7.21 (d, J=7.9 Hz, 1H), 7.04 (dd, J=1.8, 7.9 Hz, 1H), 3.94-3.90 (m, 2H), 3.57-3.51 (m, 2H), 3.18 (t, J=6.7 Hz, 1H), 1.90 (quin, J=5.9 Hz, 2H), 1.39 (s, 6H).

Example 74

N-(3,3-Dimethyl-2-oxo-1-(2,2,2-trifluoroethyl)indolin-6-yl)-3-fluoroisonicotinamide

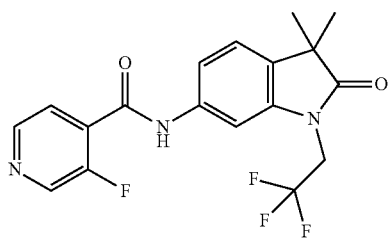

To a solution of N-(3,3-dimethyl-2-oxoindolin-6-yl)-3-fluoroisonicotinamide (example 72, 78 mg, 261 µmol) in DMF (700 µl) under an argon atmosphere was added 2,2,2-trifluoroethyl trifluoromethanesulfonate (66.5 mg, 39.6 µl, 287 µmol) and cesium carbonate (93.4 mg, 287 µmol). After 3 hours at room temperature the reaction mixture was poured into water and the aqueous phase was extracted with EtOAc. The combined organic layers were dried over Na₂SO₄ and the solvent was evaporated. The residue was purified by flash chromatography on silica gel using dichloromethane/methanol (with 10% ammonia) as eluent followed by trituration with diethyl ether/heptane. The title compound was obtained as white foam (36 mg).

MS ESI (m/z): 382.6 [(M+H)+].

¹H NMR (CDCl₃, 300 MHz) δ=8.68 (d, J=2.6 Hz, 1H), 8.66 (dd, J=1.4, 4.8 Hz, 1H), 8.43 (d, J=13.3 Hz, 1H), 8.03 (dd, J=4.9, 6.6 Hz, 1H), 7.64 (s, 1H), 7.23 (d, J=7.9 Hz, 1H), 7.13 (dd, J=1.9, 7.9 Hz, 1H), 4.36 (q, J=8.7 Hz, 2H), 1.42 (s, 6H).

Example 75

N-(3,3-Dimethyl-1-(2-(methylsulfonyl)ethyl)-2-oxoindolin-6-yl)-3-fluoroisonicotinamide

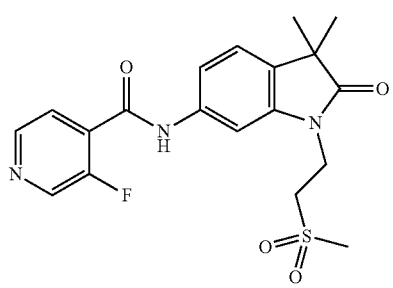 [SMILES: CC1(C)C(=O)N(CCS(C)(=O)=O)c2cc(NC(=O)c3ccncc3F)ccc21]

To a solution of N-(3,3-dimethyl-2-oxoindolin-6-yl)-3-fluoroisonicotinamide (example 72, 100 mg, 334 µmol) in DMF (1.67 ml) under an argon atmosphere was added methylsulfonylethene (35.5 mg, 31.6 µl, 334 µmol) and cesium carbonate (109 mg, 334 µmol). After 3 hours at room temperature the reaction mixture was poured into water and the aqueous phase was extracted with EtOAc. The combined organic layers were dried over Na₂SO₄ and the solvent was evaporated. The residue was purified by flash chromatography on silica gel using dichloromethane/methanol (with 10% ammonia) as eluent followed by preparative HPLC. The title compound was obtained as off-white solid (60 mg).

MS ESI (m/z): 406.5 [(M+H)+].

¹H NMR (CDCl₃, 300 MHz) δ=8.68 (d, J=2.6 Hz, 1H), 8.65 (dd, J=1.3, 4.9 Hz, 1H), 8.45 (d, J=13.1 Hz, 1H), 8.02 (dd, J=4.8, 6.5 Hz, 1H), 7.56 (d, J=1.6 Hz, 1H), 7.23 (d, J=7.9 Hz, 1H), 7.18 (dd, J=1.8, 7.9 Hz, 1H), 4.24 (t, J=6.8 Hz, 2H), 3.43 (t, J=6.8 Hz, 2H), 3.01 (s, 3H), 1.39 (s, 6H).

Example 76

N-(1,3,3-Trimethyl-2-oxo-2,3-dihydro-1H-pyrrolo[2,3-b]pyridin-6-yl)isonicotinamide

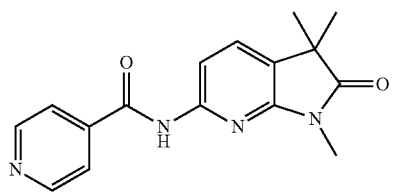 [SMILES: CN1C(=O)C(C)(C)c2ccc(NC(=O)c3ccncc3)nc21]

a) 6-Chloro-1,3,3-trimethyl-pyrrolo[2,3-b]pyridin-2-one

A suspension of 6-chloro-1H-pyrrolo[2,3-b]pyridin-2(3H)-one (300 mg, 1.78 mmol) in dry THF (4.19 ml) was added in portions during 10 minutes to a suspension of NaH (60% on mineral oil, 285 mg, 7.12 mmol) in dry THF (1.74 ml) under argon and the reaction mixture was stirred for 20 minutes. MeI (1.01 g, 445 µl, 7.12 mmol) was carefully added dropwise at 23-26° C. during 30 minutes and the mixture was stirred for another 3 hours. The reaction mixture was carefully quenched with 10 ml saturated aqueous NH₄Cl solution and diluted with EtOAc, water and saturated aqueous NaHCO₃ solution. The aqueous phase was extracted with EtOAc. The combined organic layers were washed with saturated aqueous NaHCO₃ solution, dried with sodium sulfate and the solvent was evaporated. The crude material was purified by silica gel chromatography using heptane/ethyl acetate as eluent. The title compound was isolated as red solid (149 mg).

MS ESI (m/z): 211.1/213.3 [(M+H)⁺].

¹H NMR (CDCl₃, 300 MHz) δ=7.36 (d, J=7.5 Hz, 1H), 6.98 (d, J=7.7 Hz, 1H), 3.28 (s, 3H), 1.38 (s, 6H).

b) 6-(Benzylamino)-1,3,3-trimethyl-1H-pyrrolo[2,3-b]pyridin-2(3H)-one

To a mixture of 6-chloro-1,3,3-trimethyl-1H-pyrrolo[2,3-b]pyridin-2-one (500 mg, 2.37 mmol), benzylamine (763 mg, 778 µl, 7.12 mmol) and sodium tert-butoxide (388 mg, 4.03 mmol) in toluene (10 ml) were added tris(dibenzylideneacetone)dipalladium (0) chloroform adduct (49.1 mg, 47.5 µmol) and BINAP (29.6 mg, 47.5 µmol). The reaction mixture was heated to 115° C. and stirred for 48 hours. The reaction mixture was diluted with EtOAc, silica gel was added and the mixture concentrated in vacuo. The obtained material was purified silica gel chromatography using heptane/ethyl acetate as eluent. The title compound was obtained as light yellow solid (616 mg).

MS ESI (m/z): 282.5 [(M+H)⁺].

¹H NMR (CDCl₃, 300 MHz) δ=7.41-7.27 (m, 5H), 7.17 (d, J=7.9 Hz, 1H), 5.97 (d, J=7.9 Hz, 1H), 4.85 (br t, J=5.4 Hz, 1H), 4.48 (d, J=5.9 Hz, 2H), 3.21 (s, 3H), 1.32 (s, 6H).

c) 6-amino-1,3,3-trimethyl-1H-pyrrolo[2,3-b]pyridin-2(3H)-one hydrochloride

A mixture of 6-(benzylamino)-1,3,3-trimethyl-1H-pyrrolo[2,3-b]pyridin-2(3H)-one (610 mg, 2.17 mmol) and 25% aqueous HCl solution (1.2 g, 1 ml, 8.23 mmol) in ethanol (20 ml) was evacuated three times and flushed with argon. Pd (10% on activated charcoal, 231 mg, 217 µmol) was added. Degassing was repeated, then evacuated three times and flushed with hydrogen. The reaction mixture was heated to 40° C. and stirred 4 hours at this temperature under the hydrogen atmosphere. The reaction mixture was filtered through a glass fiber filter, washed with EtOH and the solvent was evaporated. The title compound was obtained as grey solid (388 mg) and was used without further purification.

MS ESI (m/z): 192.5 [(M+H)⁺].

¹H NMR (DMSO-D₆, 300 MHz) δ=7.33 (d, J=7.9 Hz, 1H), 6.10 (d, J=8.1 Hz, 1H), 3.06 (s, 3H), 1.21 (s, 6H).

d) N-(1,3,3-Trimethyl-2-oxo-2,3-dihydro-1H-pyrrolo[2,3-b]pyridin-6-yl)isonicotinamide Prepared in analogy to example 2 from 6-amino-1,3,3-trimethyl-1H-pyrrolo[2,3-b]pyridin-2(3H)-one hydrochloride and isonicotinoyl chloride hydrochloride. The title compound was obtained as light yellow solid.

MS ESI (m/z): 297.5 [(M+H)⁺].

¹H NMR (CDCl₃, 300 MHz) δ=8.88-8.80 (m, 2H), 8.39 (br s, 1H), 8.01 (d, J=7.9 Hz, 1H), 7.80-7.74 (m, 2H), 7.50 (d, J=8.1 Hz, 1H), 3.25 (s, 3H), 1.40 (s, 6H).

Example 77

N-(1,3,3-Trimethyl-2-oxo-2,3-dihydro-1H-pyrrolo[2,3-b]pyridin-6-yl)nicotinamide

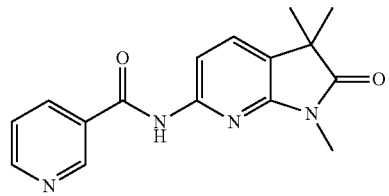

Prepared in analogy to example 2 using 6-amino-1,3,3-trimethyl-1H-pyrrolo[2,3-b]pyridin-2-one hydrochloride (example 76c) and nicotinoyl chloride hydrochloride. The title compound was obtained as light yellow solid.

MS ESI (m/z): 297.5 [(M+H)⁺].

¹H NMR (CDCl₃, 300 MHz) δ=9.17 (d, J=1.8 Hz, 1H), 8.82 (dd, J=1.6, 4.8 Hz, 1H), 8.38 (br s, 1H), 8.30-8.21 (m, 1H), 8.01 (d, J=7.9 Hz, 1H), 7.53-7.44 (m, 2H), 3.25 (s, 3H), 1.40 (s, 6H).

Example 78

2-Methyl-N-(1,3,3-trimethyl-2-oxo-2,3-dihydro-1H-pyrrolo[2,3-b]pyridin-6-yl)isonicotinamide

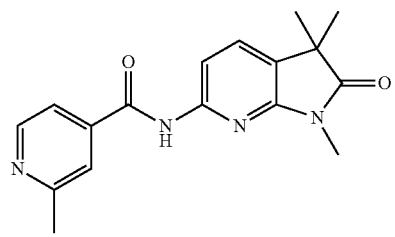 [SMILES: Cc1cc(C(=O)Nc2ccc3c(n2)N(C)C(=O)C3(C)C)ccn1]

Prepared in analogy to example 26 using 6-amino-1,3,3-trimethyl-1H-pyrrolo[2,3-b]pyridin-2(3H)-one hydrochloride (example 76c) and 2-methylisonicotinic acid. The title compound was obtained as light brown viscous oil.

MS ESI (m/z): 311.6 [(M+H)⁺].

¹H NMR (CDCl₃, 300 MHz) δ=8.71 (d, J=5.0 Hz, 1H), 8.36 (br s, 1H), 8.01 (d, J=7.9 Hz, 1H), 7.63 (s, 1H), 7.55 (d, J=5.2 Hz, 1H), 7.50 (d, J=7.9 Hz, 1H), 3.25 (s, 3H), 2.69 (s, 3H), 1.40 (s, 6H).

Example 79

N-(1-Cyclopropyl-3,3-dimethyl-2-oxo-2,3-dihydro-1H-pyrrolo[3,2-c]pyridin-6-yl)isonicotinamide

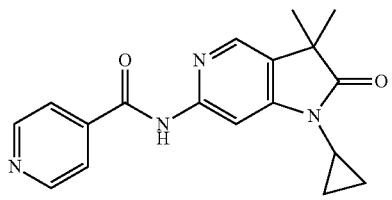 [SMILES: CC1(C)C(=O)N(C2CC2)c2cc(NC(=O)c3ccncc3)ncc21]

a) 6-Chloro-1-cyclopropyl-3,3-dimethyl-1H-pyrrolo[3,2-c]pyridin-2(3H)-one

Prepared in analogy to example 14a and 14b from 6-chloro-1,3-dihydro-pyrrolo[3,2-c]pyridin-2-one (P. Eastwood et al., Bioorg. Med. Chem. Lett. 2011, 21(18), 5270-5273 and EP2108641, 2009). The title compound was obtained as yellow crystals.

MS ESI (m/z): 237.4 [(M+H)$^+$].

$^1$H NMR (CDCl$_3$, 300 MHz) δ=8.04 (s, 1H), 7.04 (d, J=0.6 Hz, 1H), 2.65 (tt, J=3.7, 7.1 Hz, 1H), 1.38 (s, 6H), 1.14-1.07 (m, 2H), 0.91-0.86 (m, 2H).

b) 1-Cyclopropyl-6-(diphenylmethyleneamino)-3,3-dimethyl-1H-pyrrolo[3,2-c]pyridin-2(3H)-one To a suspension of 6-chloro-1-cyclopropyl-3,3-dimethyl-1H-pyrrolo[3,2-c]pyridin-2(3H)-one (1.789 g, 7.56 mmol), diphenylmethanimine (2.05 g, 1.9 ml, 11.3 mmol, Eq: 1.5) and sodium tert-butoxide (1.23 g, 12.8 mmol) in toluene (48 ml) were added tris(dibenzylideneacetone)dipalladium(0) chloroform adduct (156 mg, 151 mol) and BINAP (94.1 mg, 151 mol). The reaction mixture was heated to 100° C. for 18 hours and then diluted with dichloromethane. Silica gel was added and the solvent was evaporated. The crude material was purified by flash chromatography on silica gel using heptane/EtOAc as eluent. The title compound was obtained as brown crystals (2.31 g).

MS ESI (m/z): 382.6 [(M+H)$^+$].

c) 6-Amino-1-cyclopropyl-3,3-dimethyl-1H-pyrrolo[3,2-c]pyridin-2(3H)-one

A suspension of 1-cyclopropyl-6-(diphenylmethyleneamino)-3,3-dimethyl-1H-pyrrolo[3,2-c]pyridin-2(3H)-one (2.31 g, 6.06 mmol), sodium acetate (1.49 g, 18.2 mmol) and hydroxylamine hydrochloride (926 mg, 13.3 mmol) in methanol (60 ml) was heated to 50° C. for 3 hours. The reaction mixture was diluted with methanol, silica gel was added and the solvent was evaporated. The crude material was purified by flash chromatography on silica gel using dichloromethane/methanol as eluent. The title compound was obtained as off-white crystals (1.1 g).

MS ESI (m/z): 218.5 [(M+H)$^+$].

$^1$H NMR (CDCl$_3$, 300 MHz) δ=7.73 (s, 1H), 6.23 (s, 1H), 4.60 (br s, 2H), 2.63-2.56 (m, 1H), 1.33 (s, 6H), 1.07-1.01 (m, 2H), 0.89-0.84 (m, 2H)

d) N-(1-Cyclopropyl-3,3-dimethyl-2-oxo-2,3-dihydro-1H-pyrrolo[3,2-c]pyridin-6-yl)isonicotinamide Prepared in analogy to example 2 from 6-amino-1-cyclopropyl-3,3-dimethyl-1H-pyrrolo[3,2-c]pyridin-2(3H)-one. The title compound was obtained as white crystals.

MS ESI (m/z): 323.5 [(M+H)$^+$].

$^1$H NMR (CDCl$_3$, 300 MHz) δ=8.86-8.84 (m, 2H), 8.65 (br s, 1H), 8.19 (s, 1H), 7.97 (s, 1H), 7.77-7.75 (m, 2H), 2.72 (tt, J=3.6, 7.1 Hz, 1H), 1.39 (s, 6H), 1.20-1.13 (m, 2H), 0.96-0.91 (m, 2H).

Example 80

N-(1-Cyclopropyl-3,3-dimethyl-2-oxo-2,3-dihydro-1H-pyrrolo[3,2-c]pyridin-6-yl)nicotinamide

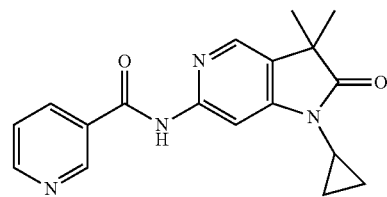 [SMILES: CC1(C)C(=O)N(C2CC2)c2cc(NC(=O)c3cccnc3)ncc21]

Prepared in analogy to example 2 from nicotinyl chloride hydrochloride and 6-amino-1-cyclopropyl-3,3-dimethyl-1H-pyrrolo[3,2-c]pyridin-2(3H)-one (example 79c). The title compound was obtained as light yellow crystals.

MS ESI (m/z): 323.5 [(M+H)$^+$].

$^1$H NMR (CDCl$_3$, 300 MHz) δ=9.18 (d, J=2.2 Hz, 1H), 8.82 (dd, J=1.5, 4.7 Hz, 1H), 8.62 (br s, 1H), 8.24 (td, J=2.0, 7.9 Hz, 1H), 8.19 (s, 1H), 7.97 (s, 1H), 7.48 (dd, J=4.8, 8.1 Hz, 1H), 2.72 (tt, J=3.7, 7.1 Hz, 1H), 1.39 (s, 6H), 1.19-1.13 (m, 2H), 0.97-0.91 (m, 2H).

Example 81

N-(1-Cyclopropyl-3,3-dimethyl-2-oxo-2,3-dihydro-1H-pyrrolo[3,2-c]pyridin-6-yl)-2-methylisonicotinamide

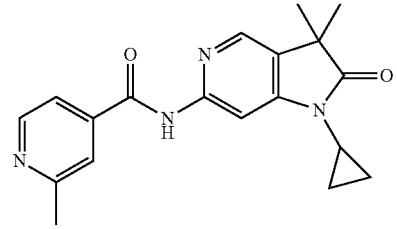 [SMILES: Cc1cc(C(=O)Nc2cc3c(cn2)C(C)(C)C(=O)N3C2CC2)ccn1]

Prepared in analogy to example 26 from 2-methylisonicotinic acid and 6-amino-1-cyclopropyl-3,3-dimethyl-1H-pyrrolo[3,2-c]pyridin-2(3H)-one (example 79c). The title compound was obtained as off-white foam.

MS ESI (m/z): 337.5 [(M+H)$^+$].

$^1$H NMR (CDCl$_3$, 300 MHz) δ=8.70 (d, J=5.2 Hz, 1H), 8.70 (br s, 1H), 8.20 (s, 1H), 7.95 (s, 1H), 7.63 (s, 1H), 7.54

(dd, J=1.2, 5.0 Hz, 1H), 2.76-2.68 (m, 1H), 2.67 (s, 3H), 1.39 (s, 6H), 1.19-1.12 (m, 2H), 0.96-0.91 (m, 2H).

Example 82

N-(1-Cyclopropyl-3,3-dimethyl-2-oxo-2,3-dihydro-1H-pyrrolo[2,3-b]pyridin-6-yl)isonicotinamide

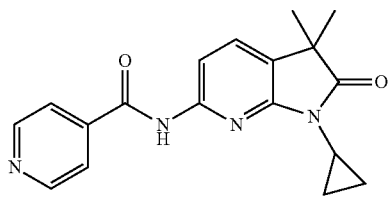 [SMILES: CC1(C)C(=O)N(C2CC2)c2nc(NC(=O)c3ccncc3)ccc21]

a) 6-Chloro-3,3-dimethyl-1H-pyrrolo[2,3-b]pyridin-2(3H)-one

To a suspension of potassium tert-butoxide (3.2 g, 28.0 mmol) in dry THF (10.5 ml) was added a suspension of 6-chloro-1H-pyrrolo[2,3-b]pyridin-2(3H)-one (1 g, 5.59 mmol) in dry THF (8.1 ml) under icecooling and under an argon atmosphere. Copper (I) bromide-dimethylsulfide complex (116 mg, 559 µmol) was added. During 15 minutes MeI (1.59 g, 699 µl, 11.2 mmol) in THF (1 ml) was carefully added dropwise at the same temperature. The cooling bath was removed. After 30 minutes at room temperature the reaction mixture was cooled to 0° C. and saturated aqueous NH$_4$Cl solution (20 ml) was added. The aqueous phase was extracted with EtOAc. The combined organic layers were washed with water, dried with Na$_2$SO$_4$ and the solvent was evaporated. The crude material was purified by silica gel chromatography using heptane/ethyl acetate as eluent. The title compound was obtained as pink solid (470 mg).

MS ESI (m/z): 197.1/199.2 [(M+H)$^+$].

$^1$H NMR (CDCl$_3$, 300 MHz) δ=8.13 (br s, 1H), 7.39 (d, J=7.9 Hz, 1H), 7.00 (d, J=7.7 Hz, 1H), 1.42 (s, 6H).

b) 6-Chloro-1-cyclopropyl-3,3-dimethyl-1H-pyrrolo[2,3-b]pyridin-2(3H)-one

To a suspension of 6-chloro-3,3-dimethyl-1H-pyrrolo[2,3-b]pyridin-2(3H)-one (150 mg, 763 mol), cyclopropylboronic acid (131 mg, 1.53 mmol), copper (II) acetate (145 mg, 801 µmol) and DMAP (280 mg, 2.29 mmol) in toluene (15 ml) was added sodium bis(trimethylsilyl)amide (2 M in THF, 400 µl, 801 µmol). While bubbling dry air through the reaction mixture, it was heated to 95° C. and stirred for 16 hours. The reaction mixture was poured into 1 M aqueous HCl solution (20 ml) and extracted with tBuOMe. The organic layers were washed with 1 M aqueous HCl solution and brine, dried over Na$_2$SO$_4$ and concentrated in vacuo. The crude material was purified by silica gel chromatography using heptane/ethyl acetate as eluent. The title compound was obtained as yellow viscous oil (178 mg).

MS ESI (m/z): 237.5, 239.5 [(M+H)$^+$].

$^1$H NMR (CDCl$_3$, 300 MHz) δ=7.34 (d, J=7.7 Hz, 1H), 6.97 (d, J=7.7 Hz, 1H), 2.89-2.77 (m, 1H), 1.34 (s, 6H), 1.10-1.03 (m, 4H).

c) 6-Amino-1-cyclopropyl-3,3-dimethyl-1H-pyrrolo[2,3-b]pyridin-2(3H)-one hydrochloride Prepared in analogy to example 76b and 76c. The title compound was obtained as grey solid. MS ESI (m/z): 218.5 [(M+H)$^+$].

$^1$H NMR (DMSO-D$_6$, 300 MHz) δ=7.37 (d, J=7.9 Hz, 1H), 6.16 (d, J=8.1 Hz, 1H), 2.78-2.68 (m, 1H), 1.18 (s, 6H), 0.98-0.86 (m, 4H)

d) N-(1-cyclopropyl-3,3-dimethyl-2-oxo-2,3-dihydro-1H-pyrrolo[2,3-b]pyridin-6-yl)isonicotinamide Prepared in analogy to example 2 using 6-amino-1-cyclopropyl-3,3-dimethyl-1H-pyrrolo[2,3-b]pyridin-2(3H)-one hydrochloride. The title compound was obtained as light yellow solid.

MS ESI (m/z): 323.6 [(M+H)$^+$].

$^1$H NMR (CDCl$_3$, 300 MHz) δ=8.92-8.79 (m, 2H), 8.46 (br s, 1H), 8.02 (d, J=7.9 Hz, 1H), 7.83-7.74 (m, 2H), 7.49 (d, J=7.9 Hz, 1H), 2.83-2.72 (m, 1H), 1.36 (s, 6H), 1.08-1.01 (m, 4H).

Example 83

2-Chloro-N-(1-cyclopropyl-3,3-dimethyl-2-oxo-2,3-dihydro-1H-pyrrolo[3,2-c]pyridin-6-yl)isonicotinamide

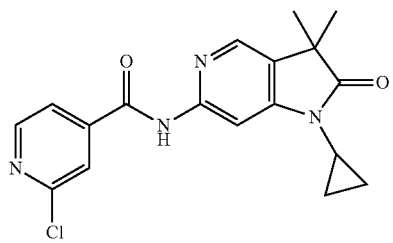 [SMILES: CC1(C)C(=O)N(C2CC2)c2cc(NC(=O)c3ccnc(Cl)c3)ncc21]

Prepared in analogy to example 26 from 2-chloroisonicotinic acid and 6-amino-1-cyclopropyl-3,3-dimethyl-1H-pyrrolo[3,2-c]pyridin-2(3H)-one (example 79c). The title compound was obtained as light yellow foam.

MS ESI (m/z): 357.5/359.5 [(M+H)$^+$].

$^1$H NMR (CDCl$_3$, 300 MHz) δ=8.61 (dd, J=0.6, 5.0 Hz, 1H), 8.59 (br s, 1H), 8.15 (br s, 1H), 7.98 (s, 1H), 7.82 (s, 1H), 7.68 (dd, J=1.4, 5.2 Hz, 1H), 2.72 (tt, J=3.7, 7.1 Hz, 1H), 1.40 (s, 6H), 1.20-1.13 (m, 2H), 0.96-0.90 (m, 2H).

Example 84

N-(1-Cyclopropyl-3,3-dimethyl-2-oxo-2,3-dihydro-1H-pyrrolo[3,2-c]pyridin-6-yl)-2-methylpyrimidine-5-carboxamide

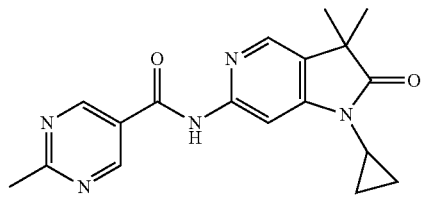 [SMILES: Cc1ncc(C(=O)Nc2cc3c(cn2)C(C)(C)C(=O)N3C2CC2)cn1]

Prepared in analogy to example 26 from 2-methylpyrimidine-5-carboxylic acid and 6-amino-1-cyclopropyl-3,3-dimethyl-1H-pyrrolo[3,2-c]pyridin-2(3H)-one (example 79c). The title compound was obtained as light yellow crystals.

MS ESI (m/z): 338.6 [(M+H)+].

1H NMR (CDCl3, 300 MHz) δ=9.17 (s, 2H), 8.15 (s, 1H), 7.97 (s, 1H), 2.85 (s, 3H), 2.72 (tt, J=3.8, 7.0 Hz, 1H), 1.39 (s, 6H), 1.20-1.13 (m, 2H), 0.96-0.91 (m, 2H).

Example 85

N-(1-Cyclopropyl-3,3-dimethyl-2-oxo-2,3-dihydro-1H-pyrrolo[3,2-c]pyridin-6-yl)isoxazole-5-carboxamide

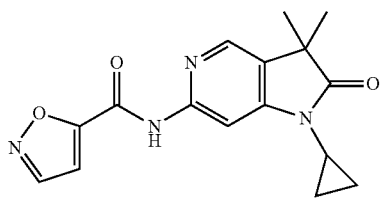 [SMILES: CC1(C)C(=O)N(C2CC2)c2cc(NC(=O)c3ccno3)ncc21]

Prepared in analogy to example 26 from isoxazole-5-carboxylic acid and 6-amino-1-cyclopropyl-3,3-dimethyl-1H-pyrrolo[3,2-c]pyridin-2(3H)-one (example 79c). The title compound was obtained as light yellow solid.

MS ESI (m/z): 313.4 [(M+H)+].

1H NMR (CDCl3, 300 MHz) δ=8.93 (br s, 1H), 8.41 (d, J=1.8 Hz, 1H), 8.11 (s, 1H), 8.02 (s, 1H), 7.07 (d, J=2.0 Hz, 1H), 2.71 (tt, J=3.7, 7.1 Hz, 1H), 1.40 (s, 6H), 1.18-1.11 (m, 2H), 0.95-0.90 (m, 2H).

Example 86

N-(1-Cyclopropyl-3,3-dimethyl-2-oxo-2,3-dihydro-1H-pyrrolo[3,2-c]pyridin-6-yl)-1-methyl-1H-pyrazole-5-carboxamide

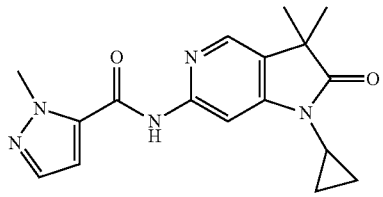 [SMILES: Cn1nccc1C(=O)Nc1cc2c(cn1)C(C)(C)C(=O)N2C1CC1]

Prepared in analogy to example 26 from 1-methyl-1H-pyrazole-5-carboxylic acid and 6-amino-1-cyclopropyl-3,3-dimethyl-1H-pyrrolo[3,2-c]pyridin-2(3H)-one (example 79c). The title compound was obtained as white foam.

MS ESI (m/z): 326.5 [(M+H)+].

1H NMR (CDCl3, 300 MHz) δ=8.36 (br s, 1H), 8.09 (d, J=0.6 Hz, 1H), 7.97 (d, J=0.8 Hz, 1H), 7.52 (d, J=2.0 Hz, 1H), 6.73 (d, J=2.2 Hz, 1H), 4.26 (s, 3H), 2.72 (tt, J=3.6, 7.1 Hz, 1H), 1.39 (s, 6H), 1.19-1.13 (m, 2H), 0.96-0.92 (m, 2H).

Example 87

N-(1-Cyclopropyl-3,3-dimethyl-2-oxo-2,3-dihydro-1H-pyrrolo[3,2-c]pyridin-6-yl)-1-methyl-1H-pyrazole-3-carboxamide

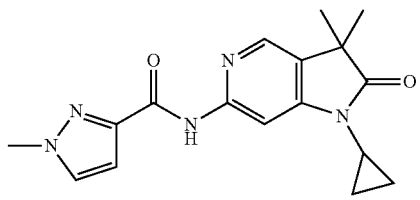 [SMILES: Cn1ccc(C(=O)Nc2cc3c(cn2)C(C)(C)C(=O)N3C2CC2)n1]

Prepared in analogy to example 26 from 1-methyl-1H-pyrazole-3-carboxylic acid and 6-amino-1-cyclopropyl-3,3-dimethyl-1H-pyrrolo[3,2-c]pyridin-2(3H)-one (example 79c). The title compound was obtained as white crystals.

MS ESI (m/z): 326.5 [(M+H)+].

1H NMR (CDCl3, 300 MHz) δ=9.36 (s, 1H), 8.22 (d, J=0.8 Hz, 1H), 7.98 (d, J=0.6 Hz, 1H), 7.42 (d, J=2.2 Hz, 1H), 6.89 (d, J=2.4 Hz, 1H), 3.97 (s, 3H), 2.70 (tt, J=3.6, 7.1 Hz, 1H), 1.38 (s, 6H), 1.17-1.10 (m, 2H), 0.95-0.90 (m, 2H).

Example 88

N-(1-Cyclopropyl-3,3-dimethyl-2-oxo-2,3-dihydro-1H-pyrrolo[3,2-c]pyridin-6-yl)-2-methoxypyrimidine-5-carboxamide

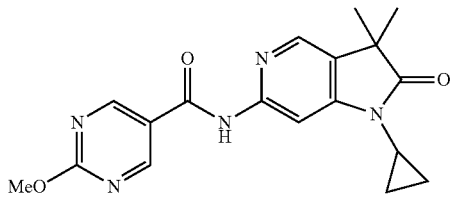 [SMILES: COc1ncc(C(=O)Nc2cc3c(cn2)C(C)(C)C(=O)N3C2CC2)cn1]

A solution of 2-methoxypyrimidine-5-carboxylic acid (70.9 mg, 460 μmol) and CDI (82.1 mg, 506 μmol) in DMF (2 ml) was heated to 60° C. for 30 minutes and then cooled to room temperature. 6-Amino-1-cyclopropyl-3,3-dimethyl-1H-pyrrolo[3,2-c]pyridin-2(3H)-one (example 79c, 100 mg, 460 μmol) was added and the mixture was heated to 60° C. for 18 hours. Further 2-methoxypyrimidine-5-carboxylic acid (70.9 mg, 460 μmol) and CDI (82.1 mg, 506 mol) were added to the reaction. After 2 hours at 60° C. citric acid (460 μl, 460 μmol) was added to the reaction mixture and stirred for 30 minutes at room temperature.

Water (25 ml) was added and the aqueous phase was extracted with dichloromethane. The combined organic layers were dried on Na2SO4 and the solvent was evaporated. The crude product was purified by flash chromatography on silica gel using heptane/EtOAc as eluent followed by purification on preparative HPLC, followed by purification by flash chromatography on silica gel using EtOAc/DCM as eluent. The title compound was obtained as white solid (27 mg).

MS ESI (m/z): 354.2 [(M+H)+].

1H NMR (CDCl3, 300 MHz) δ=9.08 (s, 2H), 8.61 (br s, 1H), 8.14 (s, 1H), 7.95 (s, 1H), 4.12 (s, 3H), 2.72 (tt, J=3.6, 7.1 Hz, 1H), 1.39 (s, 6H), 1.19-1.12 (m, 2H), 0.96-0.90 (m, 2H).

Example 89

N-(1-Cyclopropyl-3,3-dimethyl-2-oxo-2,3-dihydro-1H-pyrrolo[3,2-c]pyridin-6-yl)-3-methylisoxazole-4-carboxamide

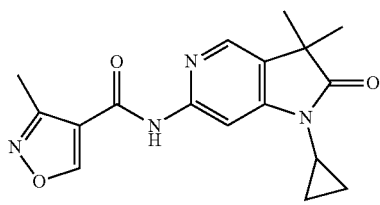 [SMILES: Cc1nocc1C(=O)Nc1cc2c(cn1)C(C)(C)C(=O)N2C1CC1]

Prepared in analogy to example 26 from 3-methylisoxazole-4-carboxylic acid and 6-amino-1-cyclopropyl-3,3-dimethyl-1H-pyrrolo[3,2-c]pyridin-2(3H)-one (example 79c). The title compound was obtained as light brown viscous oil.

MS ESI (m/z): 327.6 [(M+H)$^+$].

$^1$H NMR (CDCl$_3$, 300 MHz) δ=8.84 (s, 1H), 8.22 (br s, 1H), 8.05 (s, 1H), 7.94 (s, 1H), 2.70 (tt, J=3.7, 7.1 Hz, 1H), 2.61 (s, 3H), 1.38 (s, 6H), 1.18-1.12 (m, 2H), 0.95-0.89 (m, 2H).

Example 90

N-(1-Cyclopropyl-3,3-dimethyl-2-oxo-2,3-dihydro-1H-pyrrolo[3,2-c]pyridin-6-yl)-2-(trifluoromethyl)pyrimidine-5-carboxamide

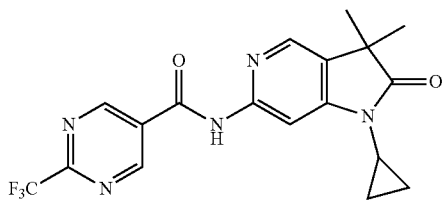 [SMILES: CC1(C)C(=O)N(C2CC2)c2cc(NC(=O)c3cnc(C(F)(F)F)nc3)ncc21]

Prepared in analogy to example 26 from 2-(trifluoromethyl)pyrimidine-5-carboxylic acid and 6-amino-1-cyclopropyl-3,3-dimethyl-1H-pyrrolo[3,2-c]pyridin-2(3H)-one (example 79c). The title compound was obtained as off-white solid.

MS ESI (m/z): 392.1 [(M+H)$^+$].

$^1$H NMR (DMSO-D$_6$, 600 MHz) δ=11.49 (s, 1H), 9.53 (s, 2H), 8.25 (s, 1H), 8.08 (s, 1H), 2.77 (tt, J=3.7, 7.1 Hz, 1H), 1.31 (s, 6H), 1.05-1.01 (m, 2H), 0.82-0.79 (m, 2H).

Biological Assays and Data

Now it has been found that the compounds of formula I and I-1 may be used for the treatment of CNS diseases.

The described compounds of formula I and I-1 reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digiscan Analyzer linked to a computer that constantly collected the beam status information. Records of photocell beam interruptions for individual animals were taken every 5 min over the duration of the experimental session and the sum of the first 6 periods was used as the final parameter. Compounds were administered either p.o. 15 min before a s.c. injection of 50 mg/kg of L-687,414, or i.p. at the same time as a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

$$((Veh+L\text{-}687{,}414 \text{ horizontal activity} - drug+L\text{-}687{,}414 \text{ horizontal activity})/Veh+L\text{-}687{,}414 \text{ horizontal activity})\times 100$$

ID$_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney U test (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

TABLE 1

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 1 known compound | 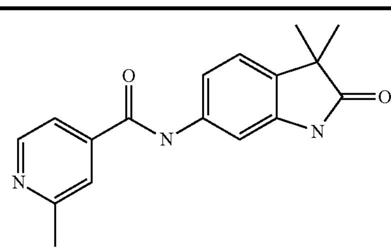 | | | | 30 | 81.6 | 0.00056 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 2 | 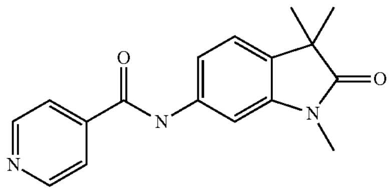 [SMILES: CN1C(=O)C(C)(C)c2ccc(NC(=O)c3ccncc3)cc21] | 1-3-10-30 | 2.06 | 0.023 | | | |
| 3 | 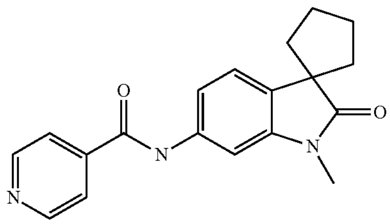 [SMILES: CN1C(=O)C2(CCCC2)c2ccc(NC(=O)c3ccncc3)cc21] | | | | 30 | 83.3 | 0.00056 |
| 4 | 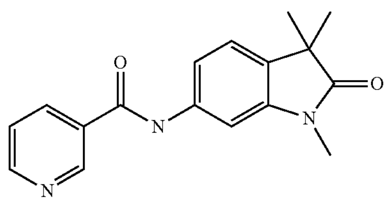 [SMILES: CN1C(=O)C(C)(C)c2ccc(NC(=O)c3cccnc3)cc21] | 1-3-10 | 1.84 | 0.0023 | | | |
| 5 | 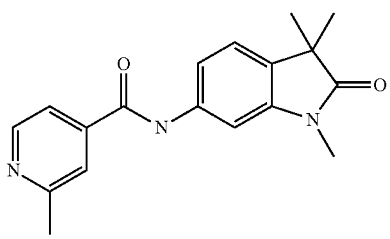 [SMILES: Cc1cc(C(=O)Nc2ccc3c(c2)N(C)C(=O)C3(C)C)ccn1] | | | | 30 | 77.2 | 0.00056 |
| 6 | 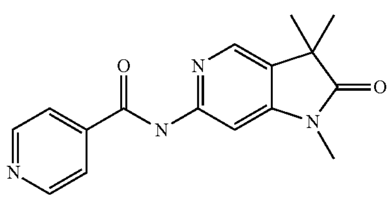 [SMILES: CN1C(=O)C(C)(C)c2cnc(NC(=O)c3ccncc3)cc21] | | | | 30 | 64.5 | 0.0012 |
| 7 | 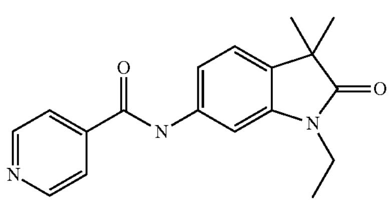 [SMILES: CCN1C(=O)C(C)(C)c2ccc(NC(=O)c3ccncc3)cc21] | | | | 30 | 90.4 | 0.00039 |
| 8 | 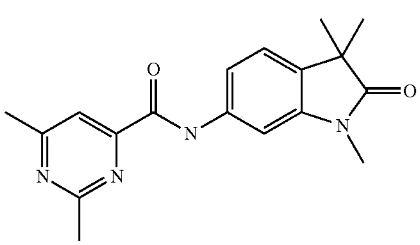 [SMILES: Cc1cc(C(=O)Nc2ccc3c(c2)N(C)C(=O)C3(C)C)nc(C)n1] | | | | 30 | 70.7 | 0.0016 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 9 | 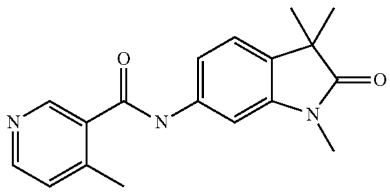 [SMILES: Cc1ccncc1C(=O)Nc1ccc2c(c1)N(C)C(=O)C2(C)C] | 1-3-10 | 6.6 | 0.0012 | | | |
| 10 | 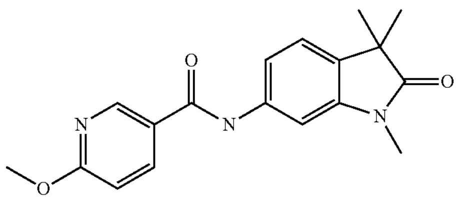 [SMILES: COc1ccc(C(=O)Nc2ccc3c(c2)N(C)C(=O)C3(C)C)cn1] | | | | 30 | 62.2 | 0.0058 |
| 12 | 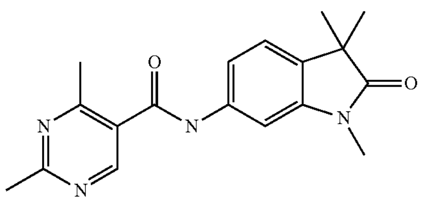 [SMILES: Cc1ncc(C(=O)Nc2ccc3c(c2)N(C)C(=O)C3(C)C)c(C)n1] | | | | 30 | 69.2 | 0.0074 |
| 14 | 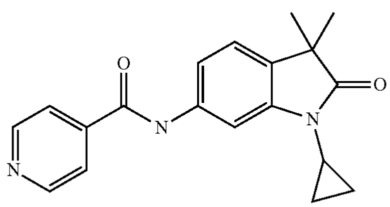 [SMILES: CC1(C)C(=O)N(C2CC2)c2cc(NC(=O)c3ccncc3)ccc21] | | | | 30 | 66.5 | 0.019 |
| 15 | 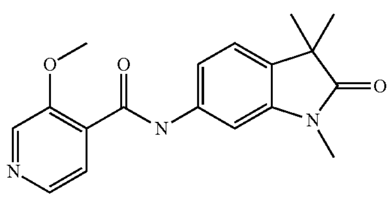 [SMILES: COc1cnccc1C(=O)Nc1ccc2c(c1)N(C)C(=O)C2(C)C] | | | | 30 | 56.3 | 0.041 |
| 17 | 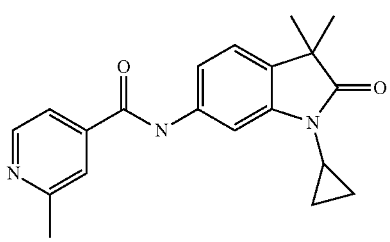 [SMILES: Cc1cc(C(=O)Nc2ccc3c(c2)N(C2CC2)C(=O)C3(C)C)ccn1] | | | | 30 | 79.3 | 0.009 |
| 18 | 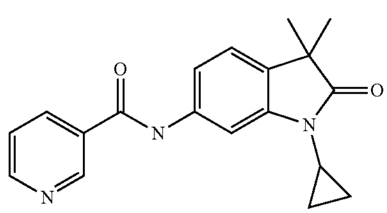 [SMILES: CC1(C)C(=O)N(C2CC2)c2cc(NC(=O)c3cccnc3)ccc21] | | | | 30 | 68.8 | 0.014 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 20 | 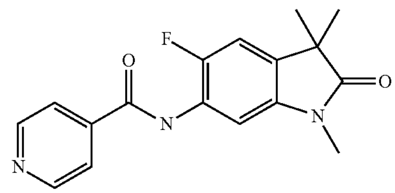 [SMILES: CN1C(=O)C(C)(C)c2cc(F)c(NC(=O)c3ccncc3)cc21] | | | | 30 | 87.3 | 0.00016 |
| 21 | 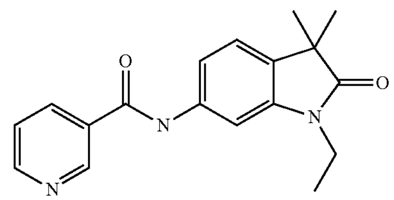 [SMILES: CCN1C(=O)C(C)(C)c2ccc(NC(=O)c3cccnc3)cc21] | | | | 30 | 76.6 | 0.0035 |
| 24 | 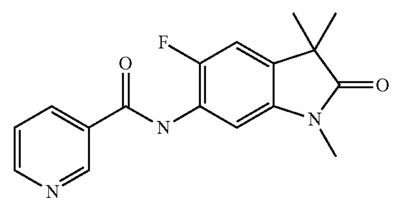 [SMILES: CN1C(=O)C(C)(C)c2cc(F)c(NC(=O)c3cccnc3)cc21] | | | | 30 | 80.0 | 0.016 |
| 27 | 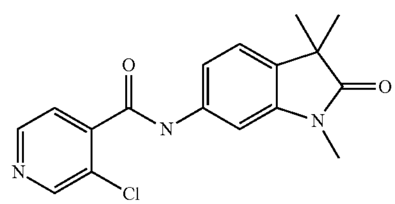 [SMILES: CN1C(=O)C(C)(C)c2ccc(NC(=O)c3ccncc3Cl)cc21] | 1-3-10 | 1.95 | 0.0054 | | | |
| 28 | 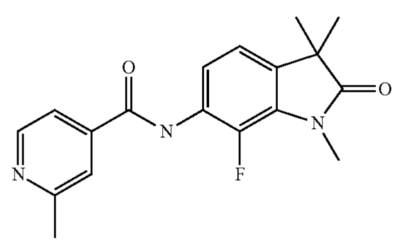 [SMILES: Cc1cc(C(=O)Nc2ccc3c(c2F)N(C)C(=O)C3(C)C)ccn1] | | | | 30 | 74.7 | 0.016 |
| 29 | 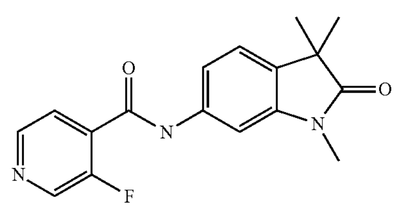 [SMILES: CN1C(=O)C(C)(C)c2ccc(NC(=O)c3ccncc3F)cc21] | 1-3-10 | 1.08 | 0.0004 | | | |
| 30 | 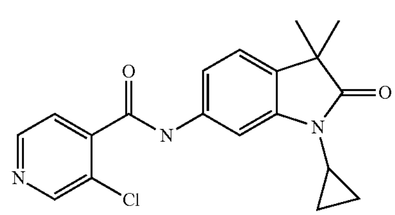 [SMILES: CC1(C)C(=O)N(C2CC2)c2cc(NC(=O)c3ccncc3Cl)ccc21] | 1-3-10 | 0.97 | 0.0074 | | | |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 31 | 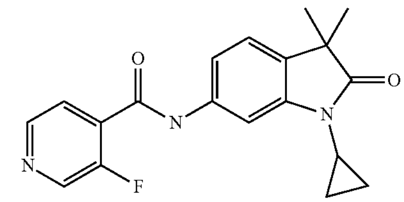 | 1-3-10 | 1.00 | 0.010 | | | |
| 33 | 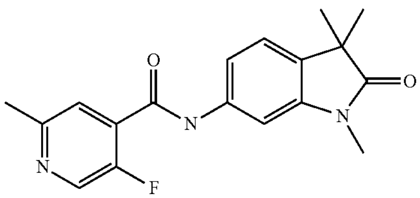 [SMILES: Cc1cc(C(=O)Nc2ccc3c(c2)N(C)C(=O)C3(C)C)c(F)cn1] | | | | 30 | 78.6 | 0.0052 |
| 35 | 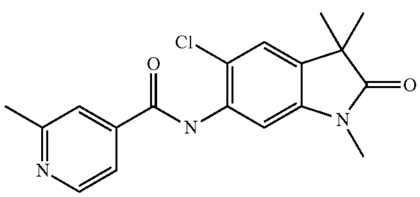 [SMILES: Cc1cc(C(=O)Nc2cc3c(cc2Cl)C(C)(C)C(=O)N3C)ccn1] | | | | 30 | 57.3 | 0.025 |
| 36 | 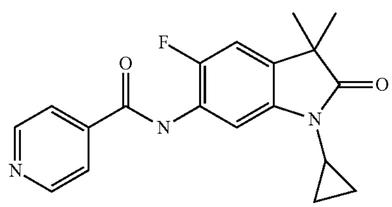 [SMILES: CC1(C)C(=O)N(C2CC2)c2cc(NC(=O)c3ccncc3)c(F)cc21] | | | | 30 | 89.0 | 0.00003 |
| 37 | 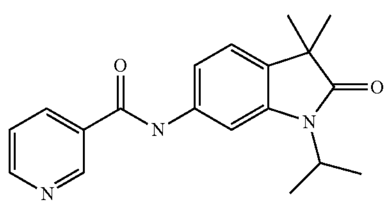 [SMILES: CC(C)N1C(=O)C(C)(C)c2ccc(NC(=O)c3cccnc3)cc21] | | | | 30 | 64.0 | 0.019 |
| 38 | 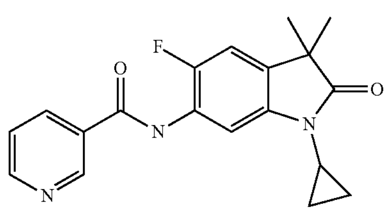 [SMILES: CC1(C)C(=O)N(C2CC2)c2cc(NC(=O)c3cccnc3)c(F)cc21] | | | | 30 | 60.8 | 0.041 |
| 39 | 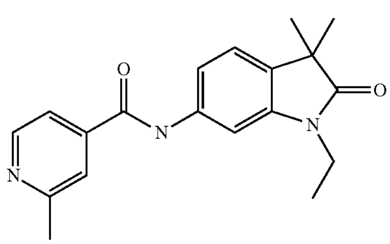 [SMILES: CCN1C(=O)C(C)(C)c2ccc(NC(=O)c3ccnc(C)c3)cc21] | | | | 30 | 58.6 | 0.041 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 40 | 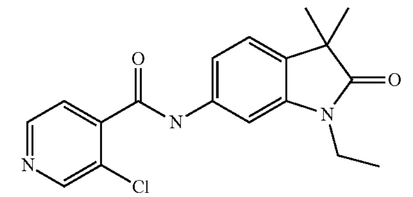 [SMILES: CCN1C(=O)C(C)(C)c2ccc(NC(=O)c3ccncc3Cl)cc21] | | | | 30 | 72.9 | 0.0035 |
| 41 | 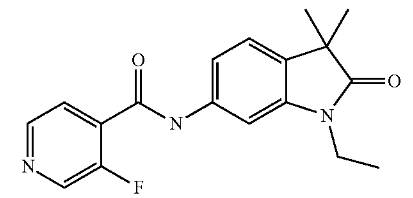 | | | | 30 | 85.2 | 0.00054 |
| 43 | 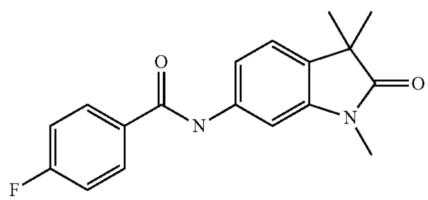 [SMILES: CN1C(=O)C(C)(C)c2ccc(NC(=O)c3ccc(F)cc3)cc21] | | | | 30 | 88.0 | 0.00008 |
| 46 | 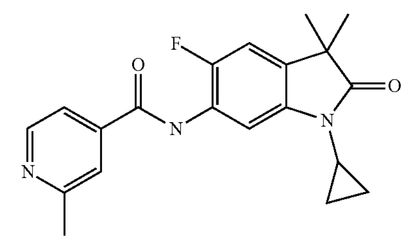 [SMILES: Cc1cc(C(=O)Nc2cc3c(cc2F)C(C)(C)C(=O)N3C2CC2)ccn1] | | | | 30 | 72.7 | 0.010 |
| 51 | 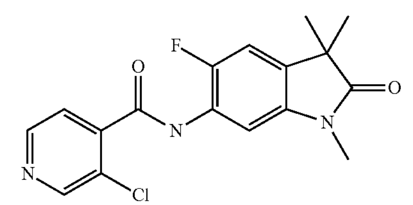 | | | | 30 | 80.1 | 0.00008 |
| 52 | 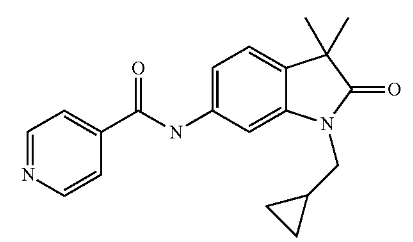 [SMILES: CC1(C)C(=O)N(CC2CC2)c2cc(NC(=O)c3ccncc3)ccc21] | | | | 30 | 78.8 | 0.00054 |
| 53 | 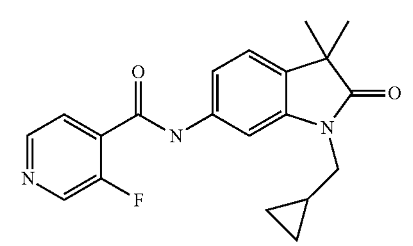 [SMILES: CC1(C)C(=O)N(CC2CC2)c2cc(NC(=O)c3ccncc3F)ccc21] | | | | 30 | 89.9 | 0.00008 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 54 | 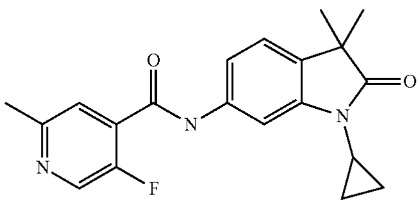 [SMILES: Cc1cc(C(=O)Nc2ccc3c(c2)N(C2CC2)C(=O)C3(C)C)c(F)cn1] | | | | 30 | 55.6 | 0.041 |
| 55 | 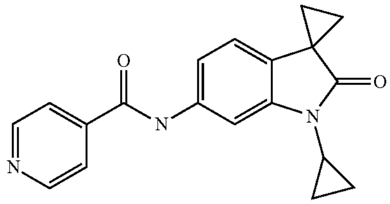 [SMILES: O=C(Nc1ccc2c(c1)N(C1CC1)C(=O)C21CC1)c1ccncc1] | | | | 30 | 61.7 | 0.014 |
| 57 | 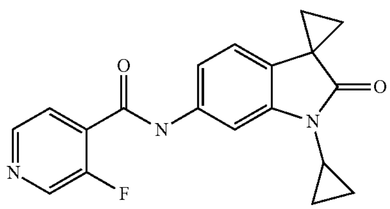 [SMILES: O=C(Nc1ccc2c(c1)N(C1CC1)C(=O)C21CC1)c1ccncc1F] | | | | 30 | 60.5 | 0.025 |
| 59 | 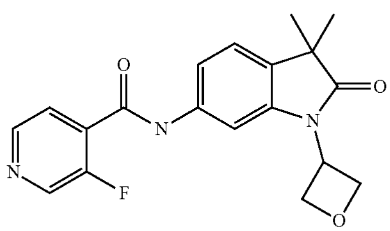 [SMILES: CC1(C)C(=O)N(C2COC2)c2cc(NC(=O)c3ccncc3F)ccc21] | | | | 30 | 88.6 | 0.00093 |
| 60 | 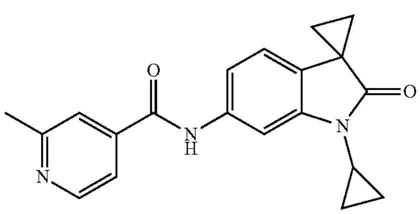 [SMILES: Cc1cc(C(=O)Nc2ccc3c(c2)N(C2CC2)C(=O)C32CC2)ccn1] | | | | 30 | 63.2 | 0.0074 |
| 62 | 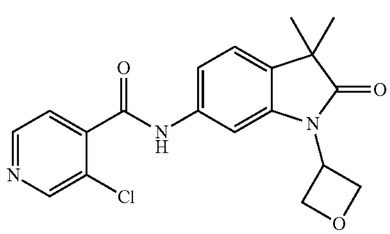 [SMILES: CC1(C)C(=O)N(C2COC2)c2cc(NC(=O)c3ccncc3Cl)ccc21] | | | | 30 | 61.7 | 0.010 |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 64 | 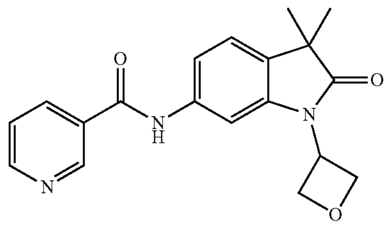 [SMILES: CC1(C)C(=O)N(C2COC2)c2cc(NC(=O)c3cccnc3)ccc21] | | | | 30 | 65.9 | 0.014 |
| 65 | 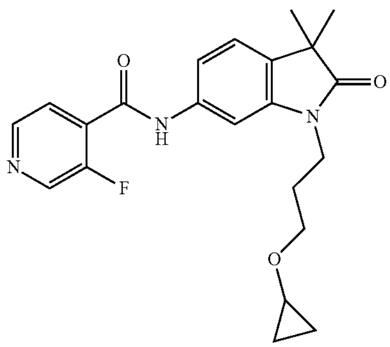 [SMILES: CC1(C)C(=O)N(CCCOC2CC2)c2cc(NC(=O)c3ccncc3F)ccc21] | | | | 30 | 91.1 | 0.00015 |
| 68 | 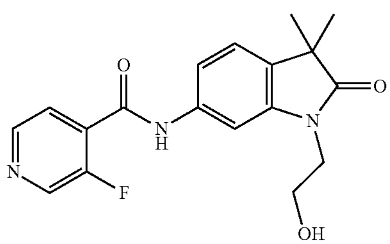 [SMILES: CC1(C)C(=O)N(CCO)c2cc(NC(=O)c3ccncc3F)ccc21] | | | | 30 | 89.1 | 0.00031 |
| 69 | 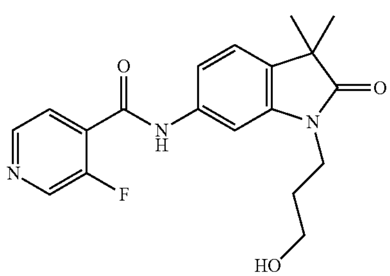 [SMILES: CC1(C)C(=O)N(CCCO)c2cc(NC(=O)c3ccncc3F)ccc21] | | | | 30 | 82.4 | 0.00031 |
| 72 | 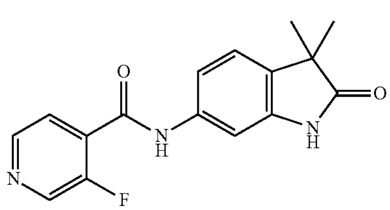 [SMILES: CC1(C)C(=O)Nc2cc(NC(=O)c3ccncc3F)ccc21] | 1-3-10 | 2.22 | 0.025 | | | |

TABLE 1-continued

Effects of compounds of formula I on L-687,414-induced hyperlocomotion

| Expl. | structure | Doses po | ID$_{50}$ po | Lowest P value | Dose ip | Inhibition, ip | P value |
|---|---|---|---|---|---|---|---|
| 73 | 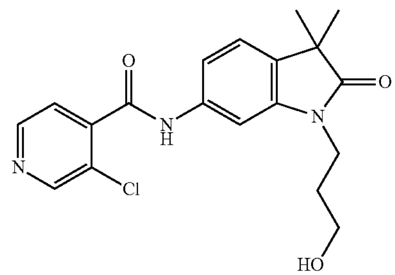 [SMILES: CC1(C)C(=O)N(CCCO)c2cc(NC(=O)c3ccncc3Cl)ccc21] | | | | 30 | 51.2 | 0.032 |
| 74 | 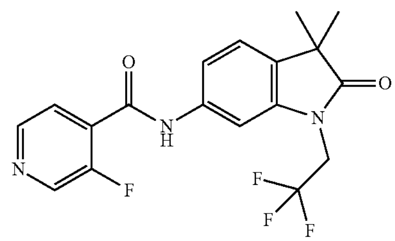 [SMILES: CC1(C)C(=O)N(CC(F)(F)F)c2cc(NC(=O)c3ccncc3F)ccc21] | | | | 30 | 76.6 | 0.0035 |
| 79 | 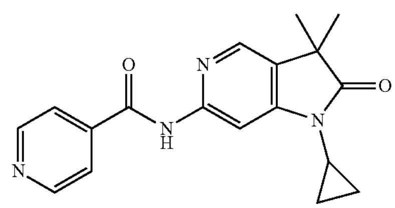 [SMILES: CC1(C)C(=O)N(C2CC2)c2cc(NC(=O)c3ccncc3)ncc21] | 1-3-10 | 0.94 | 0.0029 | | | |
| 81 | 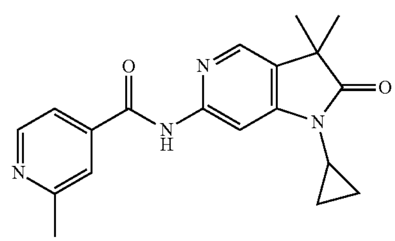 [SMILES: Cc1cc(C(=O)Nc2cc3c(cn2)C(C)(C)C(=O)N3C2CC2)ccn1] | | | | 30 | 53.1 | 0.025 |
| 83 | 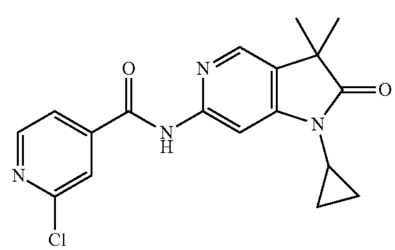 [SMILES: CC1(C)C(=O)N(C2CC2)c2cc(NC(=O)c3ccnc(Cl)c3)ncc21] | | | | 30 | 79.6 | 0.00093 |
| 85 | 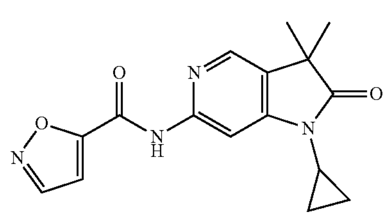 [SMILES: CC1(C)C(=O)N(C2CC2)c2cc(NC(=O)c3ccno3)ncc21] | | | | 30 | 74.9 | 0.0023 |

TABLE 1-continued

Effects of compounds of formula I on L-687,414-induced hyperlocomotion

| Expl. | structure | Doses po | $ID_{50}$ po | Lowest P value | Dose ip | Inhibition, ip | P value |
|---|---|---|---|---|---|---|---|
| 86 | 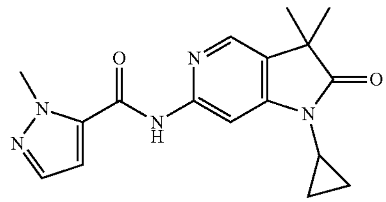 [SMILES: Cn1nccc1C(=O)Nc1cc2c(cn1)C(C)(C)C(=O)N2C1CC1] | | | | 30 | 69 | 0.0023 |
| 88 | 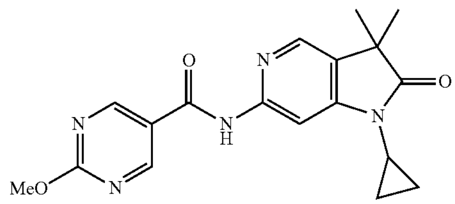 [SMILES: COc1ncc(C(=O)Nc2cc3c(cn2)C(C)(C)C(=O)N3C2CC2)cn1] | 1-3-10 | 6.11 | 0.041 | | | |

As mentioned above, some compounds have been tested in SmartCube®, an analytical system developed by PsychoGenics Inc.

SmartCube® was used to compare the behavioral signature of a test compound to a database of behavioral signatures obtained from a large set of clinically approved reference drugs, grouped per indications. In this way, the neuro-pharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each dose (mg/kg), the Y-axis indicates the relative probability that the test compound will show efficacy in the specific CNS indication.

The bar charts of example compounds 29 and 30 are shown in FIGS. 1 and 2. For comparison, the behavioral signature of the atypical antipsychotic risperidone is shown in FIG. 3 (for behavioral signatures of further atypical antipsychotic, e.g. clozapine, olanzapine, see also Roberds et al., Frontiers in Neuroscience, 2011, Vol. 5, Art. 103, 1-4). Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies at 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of ≤0.70.

TABLE 2

Data of compounds of formula I showing effects in SmartCube ®

| | Clozapine | Olanzapine | Risperidone |
|---|---|---|---|
| Example 29 | 0.63 | 0.58 | 0.56 |
| Example 30 | 0.68 | 0.67 | 0.72 |

Therefore, it can be assumed that the present compounds have similar efficacies as known atypical antipsychotics in human patients.

FIG. 1: SmartCube® signature of compound 29 showing a profile similar to that of atypical antipsychotics.

FIG. 2: SmartCube® signature of compound 30 showing a profile similar to that of atypical antipsychotics.

FIG. 3: SmartCube® signature of atypical antipsychotic risperidone.

The compounds of formula (I) and (I-1) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and (I-1) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or (I-1) or pharmaceutically acceptable salts thereof and a therapeutically inert excipient are also an object of the present invention, as is a process for the production of such medicaments which comprises bringing one or more compounds of formula I or I-1 or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) and (I-1) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention Example A Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

The invention claimed is:
1. A compound of formula

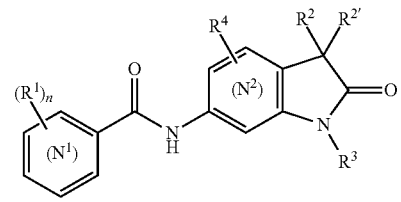

wherein

is phenyl or a heteroaryl group, selected from pyridinyl, pyrimidinyl, imidazolyl, isoxazolyl or pyrazolyl;

is phenyl or pyridinyl, wherein the N atom in the pyridinyl group may be on all free positions;
 $R^1$ is hydrogen, lower alkyl, lower alkyl substituted by halogen, lower alkoxy or halogen;
  n is 1 or 2; if n is 2, $R^1$ may be the same or not;
 $R^2/R^{2'}$ are independently from each other lower alkyl, or form together with the carbon atom to which they are attached a $C_{3-6}$-cycloalkyl ring;
 $R^3$ is lower alkyl, $C_{3-6}$-cycloalkyl, $CH_2$—$C_{3-6}$-cycloalkyl, $C_{3-6}$-cycloalkyl wherein one ring-carbon atom is replaced by —O—, $(CH_2)_3$—O—$C_{3-6}$-cycloalkyl, lower alkyl substituted by hydroxy, lower alkyl substituted by halogen, $(CH_2)_3$—$S(O)_2$—$C_{3-6}$-cycloalkyl or $(CH_2)_2$—$S(O)_2$-lower alkyl;
 $R^4$ is hydrogen, halogen or lower alkyl;
  m is 1 or 2; if m is 2, $R^4$ may be the same or not;
as well as with a pharmaceutically acceptable salts thereof, with a racemic mixture, or with its corresponding enantiomer and/or optical isomer and/or stereoisomer thereof.

2. A compound of formula I according to claim 1, wherein

is pyridinyl and

is phenyl.

3. A compound of claim 1, wherein the compound is
N-(3,3-dimethyl-2-oxo-2,3-dihydro-1H-indol-6-yl)-2-methyl-isonicotinamide (known)
N-(1,3,3-trimethyl-2-oxo-2,3-dihydro-1H-indol-6-yl)-isonicotinamide
N-(1'-methyl-2'-oxospiro[cyclopentane-1,3'-indoline]-6'-yl)isonicotinamide
N-(1,3,3-trimethyl-2-oxoindolin-6-yl)nicotinamide
2-methyl-N-(1,3,3-trimethyl-2-oxoindolin-6-yl)isonicotinamide
N-(1-ethyl-3,3-dimethyl-2-oxoindolin-6-yl)isonicotinamide
4-methyl-N-(1,3,3-trimethyl-2-oxoindolin-6-yl)nicotinamide
6-methoxy-N-(1,3,3-trimethyl-2-oxoindolin-6-yl)nicotinamide
N-(7-fluoro-1,3,3-trimethyl-2-oxoindolin-6-yl)isonicotinamide
N-(1-cyclopropyl-3,3-dimethyl-2-oxoindolin-6-yl)isonicotinamide
3-methoxy-N-(1,3,3-trimethyl-2-oxoindolin-6-yl)isonicotinamide
N-(1-cyclopropyl-3,3-dimethyl-2-oxoindolin-6-yl)-2-methylisonicotinamide
N-(1-cyclopropyl-3,3-dimethyl-2-oxoindolin-6-yl)nicotinamide
4-chloro-N-(1,3,3-trimethyl-2-oxoindolin-6-yl)nicotinamide
N-(5-fluoro-1,3,3-trimethyl-2-oxoindolin-6-yl)isonicotinamide
N-(1-ethyl-3,3-dimethyl-2-oxoindolin-6-yl)nicotinamide
N-(5-fluoro-1,3,3-trimethyl-2-oxoindolin-6-yl)-2-methylisonicotinamide
N-(7-fluoro-1,3,3-trimethyl-2-oxoindolin-6-yl)nicotinamide
N-(5-fluoro-1,3,3-trimethyl-2-oxoindolin-6-yl)nicotinamide
2-chloro-N-(1,3,3,7-tetramethyl-2-oxoindolin-6-yl)isonicotinamide
2-chloro-6-methyl-N-(1,3,3-trimethyl-2-oxoindolin-6-yl)nicotinamide
3-chloro-N-(1,3,3-trimethyl-2-oxoindolin-6-yl)isonicotinamide
N-(7-fluoro-1,3,3-trimethyl-2-oxoindolin-6-yl)-2-methylisonicotinamide
3-fluoro-N-(1,3,3-trimethyl-2-oxoindolin-6-yl)isonicotinamide
3-chloro-N-(1-cyclopropyl-3,3-dimethyl-2-oxoindolin-6-yl)isonicotinamide
N-(1-cyclopropyl-3,3-dimethyl-2-oxoindolin-6-yl)-3-fluoroisonicotinamide
N-(7-fluoro-1,3,3-trimethyl-2-oxoindolin-6-yl)-6-methylnicotinamide
5-fluoro-2-methyl-N-(1,3,3-trimethyl-2-oxoindolin-6-yl)isonicotinamide
N-(5-chloro-1,3,3-trimethyl-2-oxoindolin-6-yl)isonicotinamide
N-(5-chloro-1,3,3-trimethyl-2-oxoindolin-6-yl)-2-methylisonicotinamide
N-(1-cyclopropyl-5-fluoro-3,3-dimethyl-2-oxoindolin-6-yl)isonicotinamide
N-(1-isopropyl-3,3-dimethyl-2-oxoindolin-6-yl)nicotinamide
N-(1-cyclopropyl-5-fluoro-3,3-dimethyl-2-oxoindolin-6-yl)nicotinamide
N-(1-ethyl-3,3-dimethyl-2-oxoindolin-6-yl)-2-methyl-isonicotinamide
3-chloro-N-(1-ethyl-3,3-dimethyl-2-oxoindolin-6-yl)isonicotinamide
N-(1-ethyl-3,3-dimethyl-2-oxoindolin-6-yl)-3-fluoroisonicotinamide
N-(1-isopropyl-3,3-dimethyl-2-oxo-2,3-dihydro-1H-indol-6-yl)-2-methyl-isonicotinamide
4-fluoro-N-(1,3,3-trimethyl-2-oxoindolin-6-yl)benzamide
3-chloro-N-(1,3,3-trimethyl-2-oxoindolin-6-yl)picolinamide
N-(1-cyclopentyl-3,3-dimethyl-2-oxoindolin-6-yl)-3-fluoroisonicotinamide
N-(1-cyclopropyl-5-fluoro-3,3-dimethyl-2-oxoindolin-6-yl)-2-methylisonicotinamide
N-(5,7-difluoro-1,3,3-trimethyl-2-oxo-2,3-dihydro-1H-indol-6-yl)-isonicotinamide
3-fluoro-N-(5-fluoro-1,3,3-trimethyl-2-oxoindolin-6-yl)isonicotinamide
N-(5,7-difluoro-1,3,3-trimethyl-2-oxo-2,3-dihydro-1H-indol-6-yl)-2-methyl-isonicotinamide
N-(5,7-difluoro-1,3,3-trimethyl-2-oxo-2,3-dihydro-1H-indol-6-yl)-2-methyl-isonicotinamide
3-chloro-N-(5-fluoro-1,3,3-trimethyl-2-oxoindolin-6-yl)isonicotinamide
N-(1-(cyclopropylmethyl)-3,3-dimethyl-2-oxoindolin-6-yl)isonicotinamide
N-(1-(cyclopropylmethyl)-3,3-dimethyl-2-oxoindolin-6-yl)-3-fluoroisonicotinamide
N-(1-cyclopropyl-3,3-dimethyl-2-oxoindolin-6-yl)-5-fluoro-2-methylisonicotinamide
N-(1'-cyclopropyl-2'-oxospiro[cyclopropane-1,3'-indoline]-6'-yl)isonicotinamide
3-chloro-N-(1'-cyclopropyl-2'-oxospiro[cyclopropane-1,3'-indoline]-6'-yl)isonicotinamide
N-(1'-cyclopropyl-2'-oxospiro[cyclopropane-1,3'-indoline]-6'-yl)-3-fluoroisonicotinamide
N-(3,3-dimethyl-1-(oxetan-3-yl)-2-oxoindolin-6-yl)isonicotinamide
N-(3,3-dimethyl-1-(oxetan-3-yl)-2-oxoindolin-6-yl)isonicotinamide
N-(1'-Cyclopropyl-2'-oxospiro[cyclopropane-1,3'-indoline]-6'-yl)-2-methylisonicotinamide
3-Chloro-N-(7-fluoro-1,3,3-trimethyl-2-oxoindolin-6-yl)isonicotinamide
3-Chloro-N-(3,3-dimethyl-1-(oxetan-3-yl)-2-oxoindolin-6-yl)isonicotinamide
N-(3,3-Dimethyl-1-(oxetan-3-yl)-2-oxoindolin-6-yl)-2-methylisonicotinamide
N-(3,3-Dimethyl-1-(oxetan-3-yl)-2-oxoindolin-6-yl)nicotinamide
N-(1-(3-Cyclopropoxypropyl)-3,3-dimethyl-2-oxoindolin-6-yl)-3-fluoroisonicotinamide
N-(1-(3-Cyclopropoxypropyl)-3,3-dimethyl-2-oxoindolin-6-yl)isonicotinamide
3-Fluoro-N-(1-(hydroxymethyl)-3,3-dimethyl-2-oxoindolin-6-yl)isonicotinamide
3-Fluoro-N-(1-(2-hydroxyethyl)-3,3-dimethyl-2-oxoindolin-6-yl)isonicotinamide
3-Fluoro-N-(1-(3-hydroxypropyl)-3,3-dimethyl-2-oxoindolin-6-yl)isonicotinamide
N-(1-(3-(Cyclopropylsulfonyl)propyl)-3,3-dimethyl-2-oxoindolin-6-yl)isonicotinamide
N-(1-(3-(Cyclopropylsulfonyl)propyl)-3,3-dimethyl-2-oxoindolin-6-yl)isonicotinamide
N-(3,3-Dimethyl-2-oxoindolin-6-yl)-3-fluoroisonicotinamide
3-Chloro-N-(1-(3-hydroxypropyl)-3,3-dimethyl-2-oxoindolin-6-yl)isonicotinamide
N-(3,3-Dimethyl-2-oxo-1-(2,2,2-trifluoroethyl)indolin-6-yl)-3-fluoroisonicotinamide or
N-(3,3-Dimethyl-1-(2-(methylsulfonyl)ethyl)-2-oxoindolin-6-yl)-3-fluoroisonicotinamide.

4. A compound of formula I according to claim 1, wherein

is pyrimidinyl or imidazolyl, and

is phenyl.

5. A compound of claim 1, wherein the compound is
2,6-dimethyl-N-(1,3,3-trimethyl-2-oxoindolin-6-yl)pyrimidine-4-carboxamide
1-methyl-N-(1,3,3-trimethyl-2-oxoindolin-6-yl)-1H-imidazole-2-carboxamide
2,4-dimethyl-N-(1,3,3-trimethyl-2-oxoindolin-6-yl)pyrimidine-5-carboxamide or
2-methyl-N-(1,3,3-trimethyl-2-oxoindolin-6-yl)pyrimidine-5-carboxamide.

6. A compound of formula I according to claim 1, wherein

is pyrimidinyl, isoxazolyl or pyrazolyl, and

is pyridinyl.

7. A compound of claim 1, wherein the compound is
N-(1-Cyclopropyl-3,3-dimethyl-2-oxo-2,3-dihydro-1H-pyrrolo[3,2-c]pyridin-6-yl)-2-methylpyrimidine-5-carboxamide
N-(1-Cyclopropyl-3,3-dimethyl-2-oxo-2,3-dihydro-1H-pyrrolo[3,2-c]pyridin-6-yl)isoxazole-5-carboxamide
N-(1-Cyclopropyl-3,3-dimethyl-2-oxo-2,3-dihydro-1H-pyrrolo[3,2-c]pyridin-6-yl)-1-methyl-1H-pyrazole-5-carboxamide
N-(1-Cyclopropyl-3,3-dimethyl-2-oxo-2,3-dihydro-1H-pyrrolo[3,2-c]pyridin-6-yl)-1-methyl-1H-pyrazole-3-carboxamide
N-(1-Cyclopropyl-3,3-dimethyl-2-oxo-2,3-dihydro-1H-pyrrolo[3,2-c]pyridin-6-yl)-2-methoxypyrimidine-5-carboxamide
N-(1-Cyclopropyl-3,3-dimethyl-2-oxo-2,3-dihydro-1H-pyrrolo[3,2-c]pyridin-6-yl)-3-methylisoxazole-4-carboxamide or
N-(1-Cyclopropyl-3,3-dimethyl-2-oxo-2,3-dihydro-1H-pyrrolo[3,2-c]pyridin-6-yl)-2-(trifluoromethyl)pyrimidine-5-carboxamide.

8. A compound of formula I according to claim 1, wherein

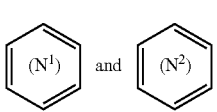

are both pyridinyl.

9. A compound of claim 1, wherein the compound is
N-(1,3,3-trimethyl-2-oxo-2,3-dihydro-1H-pyrrolo[3,2-c]pyridin-6-yl)isonicotinamide
N-(1,3,3-Trimethyl-2-oxo-2,3-dihydro-1H-pyrrolo[2,3-b]pyridin-6-yl)isonicotinamide
N-(1,3,3-Trimethyl-2-oxo-2,3-dihydro-1H-pyrrolo[2,3-b]pyridin-6-yl)nicotinamide
2-Methyl-N-(1,3,3-trimethyl-2-oxo-2,3-dihydro-1H-pyrrolo[2,3-b]pyridin-6-yl)isonicotinamide
N-(1-Cyclopropyl-3,3-dimethyl-2-oxo-2,3-dihydro-1H-pyrrolo[3,2-c]pyridin-6-yl)isonicotinamide
N-(1-Cyclopropyl-3,3-dimethyl-2-oxo-2,3-dihydro-1H-pyrrolo[3,2-c]pyridin-6-yl)nicotinamide
N-(1-Cyclopropyl-3,3-dimethyl-2-oxo-2,3-dihydro-1H-pyrrolo[3,2-c]pyridin-6-yl)-2-methylisonicotinamide
N-(1-Cyclopropyl-3,3-dimethyl-2-oxo-2,3-dihydro-1H-pyrrolo[2,3-b]pyridin-6-yl)isonicotinamide or
2-Chloro-N-(1-cyclopropyl-3,3-dimethyl-2-oxo-2,3-dihydro-1H-pyrrolo[3,2-c]pyridin-6-yl)isonicotinamide.

10. A combination of a compound of formula I or of N-(3,3-dimethyl-2-oxo-2,3-dihydro-1H-indol-6-yl)-2-methylisonicotinamide according to claim 1 together with a known marketed antipsychotic, antidepressant, anxiolytic or mood stabilizer.

11. A combination according to claim 8, wherein the marketed antipsychotic drug is olanzapine (Zyprexa®), clozapine (Clozaril®), risperidone (Risperdal®), aripiprazole (Abilify®) or ziprasidone.

12. A combination according to claim 10, wherein the marketed anti-depressive drug is citalopram (Celexa®), escitalopram (Lexapro®, Cipralex®), paroxetine (Paxil®, Seroxat), fluoxetine (Prozac®), sertraline (Zoloft®, Lustral™) duloxetine (Cymbalta®), milnacipran (Ixel®, Savella®), venlafaxine (Effexor®), or mirtazapine (Remeron®).

13. A combination according to claim 10, wherein the marketed anxiolytic drug is alprazolam (Helex®, Xanax®, Xanor™, Onax™, Alprox™, Restyl™, Tafil™, Paxal™), chlordiazepoxide (Librium™, Risolid™, Elenium™), clonazepam (Rivotril™, Klonopin®, Iktorivil™, Paxam™), diazepam (Antenex™, Apaurin™, Apzepam™, Apozepam™, Helaxid™, Pax™, Stesolid™, Stedib™, Valium®, Vival™, Valaxona™), Estazolam (ProSom™), eszopiclone (Lunesta®), zaleplon (Sonata®, Starnoc™), zolpidem (Ambien®, Nytamel™, Stilnoct™, Stilnox, Zoldem™, Zolnod™), pregabalin (Lyrica®) or gabapentin (Fanatrex™, Gabarone™, Gralise®, Neurontin®, Nupentin™).

14. A combination according to claim 10, wherein the marketed mood stabilizer is Carbamazepine (Tegretol®), Lamotrigine (Lamictal®), Lithium (Eskalith®, Lithane™, Lithobid®), and Valproic Acid (Depakote®).

15. A process for preparation of a compound of formula I as described in claim 1, comprising
reacting a compound of formula

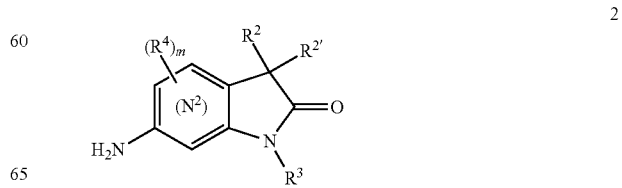

with a compound of formula

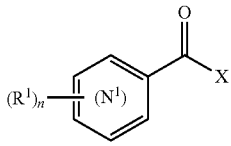

to a compound of formula

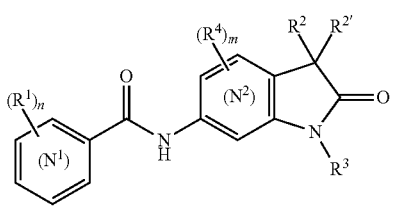

wherein X is hydroxy or chlorine and the further groups have the meaning as described in claim 1, and, if desired, converting the compounds obtained into pharmaceutically acceptable acid addition salts.

16. A compound of claim 1, whenever prepared by a process as claimed in claim 15.

17. A pharmaceutical composition comprising a compound of claim 1 and a therapeutically active carrier for the treatment of certain central nervous system disorders.

18. A method for the treatment of central nervous system disorders which are positive and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems, which method comprises administering an effective amount of a compound of claim 1 and of the compound N-(3,3-dimethyl-2-oxo-2,3-dihydro-1H-indol-6-yl)-2-methyl-isonicotinamide.

* * * * *